(12) United States Patent
Gamolski

(10) Patent No.: US 12,246,073 B2
(45) Date of Patent: Mar. 11, 2025

(54) DNA VECTOR FOR TARGETED GENE THERAPY

(71) Applicants: GENETIC DIAGNOSTICS AND THERAPY 21 LTD, London (GB); Obschestvo s ogranichennoi otvetstvennostju «REKOMBITEKH», Moscow (RU)

(72) Inventor: Anton Gamolski, London (GB)

(73) Assignees: GENETIC DIAGNOSTICS AND THERAPY 21 LTD, London (GB); Obschestvo s ogranchennoi otvetsvennostju «REKOMBITEKH», Moscow (RU)

( * ) Notice: Subject to any disclaimer, the term of this patent is extended or adjusted under 35 U.S.C. 154(b) by 451 days.

(21) Appl. No.: 17/290,418

(22) PCT Filed: Nov. 5, 2019

(86) PCT No.: PCT/RU2019/000786
§ 371 (c)(1),
(2) Date: Apr. 30, 2021

(87) PCT Pub. No.: WO2020/096492
PCT Pub. Date: May 14, 2020

(65) Prior Publication Data
US 2022/0008556 A1 Jan. 13, 2022

(30) Foreign Application Priority Data
Nov. 8, 2018 (RU) .......................... RU2018139383

(51) Int. Cl.
*A61K 48/00* (2006.01)
*C12N 15/70* (2006.01)
*C12N 15/85* (2006.01)

(52) U.S. Cl.
CPC .......... *A61K 48/0058* (2013.01); *C12N 15/70* (2013.01); *C12N 15/85* (2013.01); *C12N 2800/90* (2013.01); *C12N 2830/008* (2013.01)

(58) Field of Classification Search
None
See application file for complete search history.

(56) References Cited

PUBLICATIONS

GenBank Accession No. AF239249 "Eukaryotic expression vector pCMV5, complete sequence", 2000 (Year: 2000).*

* cited by examiner

*Primary Examiner* — Kevin K Hill
*Assistant Examiner* — Alexandra F Connors
(74) *Attorney, Agent, or Firm* — Nadya Reingand

(57) ABSTRACT

The invention relates to biotechnology, to gene therapy DNA vectors, a *Escherichia coli* strain JM110-NAS, a method of its production and selection of gene therapy DNA vector for targeted gene therapy. The method of a gene therapy DNA vector for targeted gene therapy includes construction of a 2408 bp vector containing a 688 bp replication origin, a 467 bp transcription terminator hGH-TA, a 137 bp regulatory region RNA-out of transposon TnlO, a 1018 bp kanamycin resistance gene, and a 68 bp poly linker. Vector cleaving by XhoI and BamHI restriction endonucleases and ligation with promoter and regulatory region, while a site containing the promoter region of a human is used for the production of the gene therapy DNA vector of interest. The kanamycin resistance gene is cleaved by SpeI restriction sites. The remaining fragment was ligated to itself. The invention allows high effective targeted gene therapy.

Figure 1:
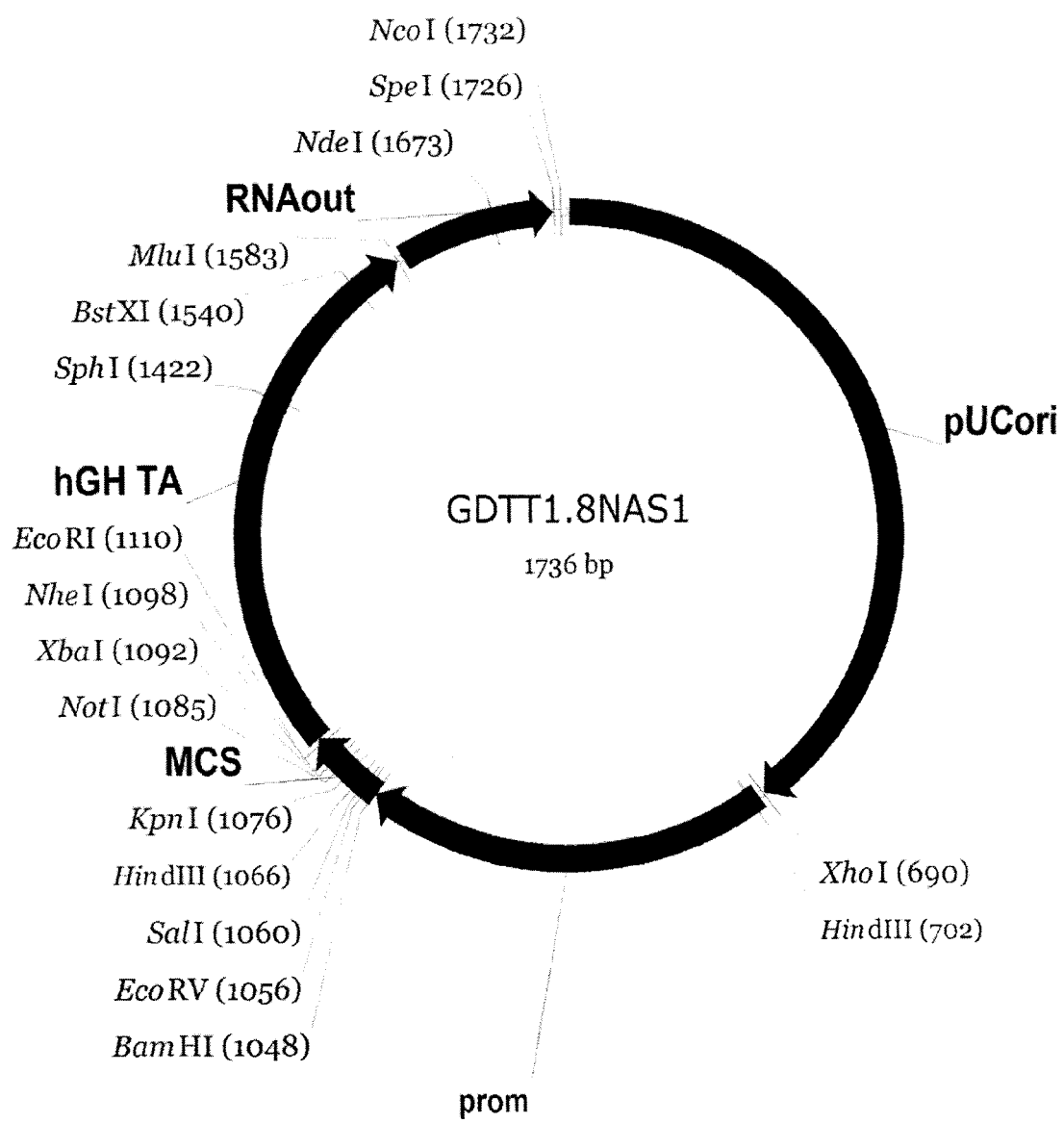

1 Claim, 38 Drawing Sheets
Specification includes a Sequence Listing.

DNA VECTOR FOR TARGETED GENE THERAPY

FIELD OF THE INVENTION

The invention refers to genetic engineering and can be used in biotechnology, medicine, and agriculture for the manufacture of gene therapy products.

REFERENCE TO A SEQUENCE LISTING

SEQ ID NO: 1 through SEQ ID NO: 106, incorporated fully by reference herein, are provided in ASCII format together in one separately enclosed .TXT file, submitted via EFS-Web—File name: 000786-seq-listing-ANSI-8-16-2021.txt; Date of Creation: Aug. 17, 2021; File size: 46.7 KB.

BACKGROUND OF THE INVENTION

Gene therapy is an innovative approach in medicine aimed at treating inherited and acquired diseases by means of delivery of new genetic material into a patient's cells to compensate for or suppress the function of a mutant gene and/or treat a genetic disorder.

Transporters of genetic material (gene therapy vectors) are divided into viral and nonviral vectors. The most efficient viral vectors include retroviruses, lentiviruses, adeno-associated viruses (AAV), herpesviruses, poxviruses, and adenoviruses (Lukashev A N, Zamyatnin A A Jr. Viral Vectors for Gene Therapy: Current State and Clinical Perspectives. Biochemistry (Mosc). 2016. 81:700-708). Nonviral delivery of genetic material predominantly involves plasmids bearing a therapeutic gene and combined with various carriers such as lipids, cationic polymers, dendrimers, polypeptides, and nanoparticles (Mintzer M A, Simanek E E. Nonviral vectors for gene delivery. Chem Rev. 2009. 109:259-302).

Despite a virus being naturally almost an ideal agent for the delivery of recombinant DNA into the cell, in terms of both speed and efficiency, there are some practical limitations to the use of viral delivery systems. These include manufacturing challenges, lack of selectivity, immune response, potential carcinogenic risks, as well as inflammation following transduction. Some of these problems are yet to be solved. This is why lately gene therapy has paid increasingly more attention to the development of nonviral gene delivery systems.

Plasmid is an autonomously replicating extrachromosomal circular DNA. Plasmids may contain genes of resistance to antibiotics, heavy metal ions, and genes controlling catabolism of some organic compounds (Lipps G. (editor). (2008). Plasmids: Current Research and Future Trends. Caister Academic Press. ISBN 978-1-904455-35-6). As mobile genetic elements, plasmids are capable of being transmitted from one bacterial cell to another by conjugation, thus facilitating horizontal gene transfer.

Plasmids are free of limitations inherent in viral vectors. In the target cell, they exist as an episome without being integrated into the genome, while producing them is quite cheap, and there is no immune response or side effects caused by the administration of plasmids, which makes them a convenient tool for gene therapy (transfer of therapeutic genes) and prevention of the genetic diseases (DNA vaccination) (Li L, Petrovsky N. Molecular mechanisms for enhanced DNA vaccine immunogenicity. Expert Rev Vaccines. 2016; 15(3):313-29).

Other than being quite a promising means of delivery in gene therapy, plasmids have long been instrumental in laboratories specializing in molecular biology and other biotechnology, and have been applied successfully in molecular cloning and the development of recombinant proteins (Russell, David W.; Sambrook, Joseph (2001), Molecular cloning: a laboratory manual. Cold Spring Harbor, N.Y; Cold Spring Harbor Laboratory)

Despite the obvious prospects for gene therapy, a critical limitation to the use of plasmids as therapeutic agents is that they contain: i) genes of resistance to antibiotics for the production of constructs in carrying strains, ii) various regulatory elements represented by sequences of viral genomes. Another limitation is the size of therapeutic plasmids which determines the efficiency of vector delivery to the target cell.

It is commonly known that over the past years the entire world has been witnessing increasingly growing resistance of infectious agents to antimicrobial drugs. The development of antimicrobial resistance is a natural biological response to antibiotics which cause selective pressure facilitating the selection, survival and growth of resistant strains of microorganisms. Resistance to antibiotics is of great social and economic importance and is considered to be a threat to national security (MacPherson D. W., Gushulak B. D., Baine W. B., Bala S., Gubbins P. O., Holtom P., Segarra-Newnham M. 2009. Population mobility, globalization, and antimicrobial drug resistance. Emerg Infect Dis 15:1727-1732). It is plasmids that ensure horizontal transfer of genes, including antibiotic resistance genes, inside a micropopulation, which gives them a selective advantage. Therefore, the growth of human infectious agents resistant to present-day antibiotics is attributed to horizontal gene transfer (Ramirez M S, Traglia G M, Lin D L, Tran T, Tolmasky M E. Plasmid-Mediated Antibiotic Resistance and Virulence in Gram-Negatives: the *Klebsiella pneumoniae* Paradigm. Microbiol Spectr. 2014 (5).

For this reason, the European Medicines Agency deems it necessary to refrain from adding antibiotic resistance marker genes to newly engineered plasmids for gene therapy (Reflection paper on design modifications of gene therapy medicinal products during development/14 Dec. 2011 EMA/CAT/GTWP/44236/2009 Committee for advanced therapies).

One more significant limitation to the use of therapeutic plasmid vectors is that they contain regulatory elements to increase the expression of target genes (promoters, enhancers, post-translational regulatory elements), which are mainly represented by nucleotide sequences of genomes of various viruses (Draft Guideline on the quality, non-clinical and clinical aspects of gene therapy medicinal products, http://www.ema.europa.eu/docs/en_GB/document_library/Scientific_guideline/2015/05/WC500187020.pdf).

Another disadvantage of existing plasmid vectors for gene therapy is their size (length). It is known that the greater the length of plasmid, the less efficiently it penetrates the target cell. Existing plasmids often have unnecessary, non-functional sites that increase their length substantially (Mairhofer J, Grabherr R. Rational vector design for efficient non-viral gene delivery: challenges facing the use of plasmid DNA. Mol Biotechnol. 2008.39(2):97-104).

Another important limitation of the use of therapy plasmid vectors is the lack of tissue-specific expression of target genes.

A therapy that involves plasmid vectors without the function of tissue-specific expression of target genes in target cells (target tissue, organ) in some cases can lead to side effects, such as product toxicity due to overexpression, feedback inhibition of other gene expressions, which risk may exceed the benefit. It is known that gene expression is provided by regulatory elements in the genome, such as promoters, enhancers and silencers of various structures. These regulatory elements contain sequences for binding regulatory proteins, including transcription factors. This is what provides the control of gene expression at the transcription level. Certain genes can be transcribed in all tissues of the body, others in several tissues, often genes are expressed in cells of only one tissue. Such regulatory regions of genes that characterized by tissue-specific transcription can be used to create gene therapy vectors for the specific expression of target genes in a strictly defined tissue (or group of tissues) of the body, which in turn increases the efficiency and safety of these gene therapy vectors (Gill D R, Pringle I A, Hyde S C. Progress and prospects: the design and production of plasmid vectors. Gene Ther. 2009. 16:165-171) and is the targeted gene therapy approach. In addition, by introducing various nucleases, for example, Cas9 into these vectors, the therapeutic genomic editing approach can be implemented, which is also the targeted gene therapy.

We are aware of a method for accumulating plasmids in *Escherichia coli* strains without using antibiotics (Cranenburgh R M, Hanak J A, Williams S G, Sherratt D J. *Escherichia coli* strains that allow antibiotic-free plasmid selection and maintenance by repressor titration. Nucleic Acids Res. 2001. 29(5):E26). DH1lacdapD and DH1lacP2dapD strains of *Escherichia coli* were constructed, where gene dapD encoding 2,3,4,5-tetrahydropyridine-2,6-dicarboxylate-N-succinyltransferase enzyme involved in the biosynthesis of L-lysine is controlled by the lac promoter. In the absence of the inducer IPTG (Isopropyl-β-D-1-thiogalactopyranoside), these strains are subject to lysis. The administration of the pORT multicopy plasmid vector containing the lac operon induces expression of gene dapD, and, therefore, transformed clones may be selected and reproduced. These strains, however, feature low levels and instability of transformation.

We are also aware of a method for constructing *Escherichia coli* strains for the production of plasmids in an antibiotic-free plasmid selection system (Mairhofer J, Pfaffenzeller I, Merz D, Grabherr R. A novel antibiotic free plasmid selection system: advances in safe and efficient DNA therapy. Biotechnol J. 2008. 3(1):83-89). The selected bacterial strains (e.g., DG5α, JM109, MG1655) were modified in such a way that plasmid replication inhibitor RNA I could suppress the translation of genes essential for bacterial activity (for example, murA encoding the enzyme UDP-N-acetylglucosamine 1-carboxyvinyl-transferase involved in the biosynthesis of bacterial cell wall peptidoglycan) by forming a duplex of RNA/antisense RNA. Gene murA was controlled by repressor protein tetR and could only be expressed in the presence of the constructed RNA I-carrying plasmid. However, it was discovered that adding IPTG would result in the production of *Escherichia coli* colonies free of the target plasmid vector. The mechanism of selection inhibition remains unknown.

We are also aware of a method for constructing vectors of the smallest length. A small supercoiled DNA molecule was engineered which is devoid of all prokaryotic nucleotide sequences and contains only origins of replication and the antibiotic resistance gene (the so-called "minicircle"). The vector was produced by integrase-mediated intramolecular integration using phage φC31 (Chen Z Y, He C Y, Ehrhardt A, Kay M A. Minicircle DNA vectors devoid of bacterial DNA result in persistent and high-level transgene expression in vivo. Mol Ther. 2003. 8(3):495-500). The disadvantages of such plasmid vectors include the difficulty of their production and the impossibility to produce them on an industrial scale.

We are aware of the invention described in Patent Application No. US 2011152377/10 for the preparation of an expression construct without the resistance to antibiotics which contains a polynucleotide encoding the repressor protein. The expression of the said repressor protein regulates the expression of the toxic gene product integrated into the region of the *E. coli* genome. However, like any other method of selection based on the use of repressor proteins, this method is characterized by unstable and inefficient transformation.

We are aware of U.S. Pat. No. 9,644,211 that describes a method for producing a vector of the smallest length ("minicircle"). This vector does not contain prokaryotes sequences and is produced by parA-mediated recombination in a cultured *E. coli* strain. The disadvantage of this method of producing the shortest vector is the impossibility to use it on an industrial scale.

U.S. Pat. No. 7,341,847 describes the use of the platelet-derived growth factor PDGF B chain promoter in combination with an enhancer of the immediate early human cytomegalovirus genes in a vector based on a plasmid or virus for expression of transgenes in neuronal tissue. However, the presence of viral genome elements in the plasmid vector limits its use for human gene therapy.

The prototype of this invention in terms of the use of recombinant DNA vectors for gene therapy is the method of producing a recombinant vector for genetic immunisation (U.S. Pat. No. 9,550,998). The plasmid vector is a super-coiled plasmid DNA vector that is used for the expression of cloned genes in human and animal cells. The vector contains an origin of replication, regulatory elements comprising human cytomegalovirus promoter and enhancer, and regulatory sequences from the human T-cell lymphotropic virus.

The vector is accumulated in a dedicated *E. coli* strain without using antibiotics through antisense complementation of sacB gene administered into the strain by means of bacteriophage. The use of this DNA vector in gene therapy is limited by the presence of regulatory sequences of viral genomes.

DISCLOSURE OF THE INVENTION

The purpose of this invention is to construct the group of gene therapy DNA vectors for targeted gene therapy, which combine the following:
I) possibility of safe use in the gene therapy of human beings and animals due to the absence of antibiotic resistance genes in the gene therapy DNA vectors;
II) length that ensures efficient gene delivery to the target cell;
III) presence of regulatory elements that ensure efficient expression of the therapeutic genes while not being represented by nucleotide sequences of viral genomes;
IV) possibility of choosing the gene therapy DNA vector for targeted gene therapy from a group of gene therapy DNA vectors carrying different promoter and regulatory regions to construct a gene therapy NA vector containing a target gene based on criteria of its tissue-specific expression and maximum efficiency in the target cell line, target tissue or organ of the human body.

V) constructability and producibility on an industrial scale.

Item I and III are critical and are provided herein in compliance with the requirements of the state regulators for gene therapy medicines and, specifically, the requirement of the European Medicines Agency to refrain from adding antibiotic resistance marker genes to newly engineered plasmid vectors for gene therapy (Reflection paper on design modifications of gene therapy medicinal products during development/14 Dec. 2011 EMA/CAT/GTWP/44236/2009 Committee for advanced therapies) and refrain from adding viral genomes to newly engineered plasmid vectors for gene therapy (Guideline on the quality, non-clinical and clinical aspects of gene therapy medicinal products/23 Mar. 2015, EMA/CAT/80183/2014, Committee for Advanced Therapies).

The purpose of the invention also includes the construction of strains carrying these gene therapy DNA vectors for the production of these gene therapy DNA vectors on an industrial scale.

The specified purpose is achieved by constructing gene therapy DNA vector for targeted gene therapy aimed at increasing the expression level of the therapeutic gene in target tissue cells, characterized by selectivity, ensuring the expression of the therapeutic gene in cells of this particular target tissue due to the presence of a gene therapy DNA vector of the promoter and regulatory region that is tissue-specific for cells of this target tissue, while a 1736 bp gene therapy DNA vector GDTT1.8NAS1 with the nucleotide sequence SEQ ID No. 1 contains the promoter and regulatory region of the human myoglobin gene that is tissue-specific for muscle tissue cells, a 1654 bp gene therapy DNA vector GDTT1.8NAS2 with the nucleotide sequence SEQ ID No. 2 contains the promoter and regulatory region of the human elastase gene that is tissue-specific for skin cells, a 1783 bp gene therapy DNA vector GDTT1.8NAS3 with the nucleotide sequence SEQ ID No. 3 contains the promoter and regulatory region of the human intercellular adhesion molecule gene 2 that is tissue-specific for vascular endothelial cells, a 1953 bp gene therapy DNA vector GDTT1.8NAS4 with the nucleotide sequence SEQ ID No. 4 contains the promoter and regulatory region of the human osteocalcin gene 2 that is tissue-specific for bone tissue cells, namely osteoblasts and odontoblasts, a 2019 bp gene therapy DNA vector GDTT1.8NAS5 with the nucleotide sequence SEQ ID No. 5 contains the promoter and regulatory region of the human surfactant protein B gene that is tissue-specific for epithelial cells of the bronchial and alveolar epithelial cells, a 1940 bp gene therapy DNA vector GDTT1.8NAS6 with the nucleotide sequence SEQ ID No. 6 contains the promoter and regulatory region of the human synapsin I gene that is tissue-specific for nervous tissue cells, namely neurons, a 2620 bp gene therapy DNA vector GDTT1.8NAS7 with the nucleotide sequence SEQ ID No. 7 contains the promoter and regulatory region of the human nephrine gene that is tissue-specific for kidney cells, namely podocytes, a 2240 bp gene therapy DNA vector GDTT1.8NAS8 with the nucleotide sequence SEQ ID No. 8 contains the promoter and regulatory region of the human common leukocyte antigen CD45 gene that is tissue-specific for blood cells, namely hematopoietic blood cells, a 2604 bp gene therapy DNA vector GDTT1.8NAS9 with the nucleotide sequence SEQ ID No. 9 contains the promoter and regulatory region of the human B29 protein gene tissue-specific for blood cells, namely lymphocytes, a 2048 bp gene therapy DNA vector GDTT1.8NAS10 with the nucleotide sequence SEQ ID No. 10 contains the promoter and regulatory region of the human CD68 protein gene that is tissue-specific for blood cells, namely macrophages, a 1978 bp gene therapy DNA vector GDTT1.8NAS11 with the nucleotide sequence SEQ ID No. 11 contains the promoter and regulatory region of the human insulin gene that is tissue-specific for cells of pancreas, namely beta cells of pancreas.

At the same time, the method of production of gene therapy DNA vector for targeted gene therapy involves initial construction of a 2408 bp vector containing a 688 bp replication origin, a 467 bp transcription terminator hGH-TA, a 137 bp regulatory region RNA-out of transposon Tn10, a 1018 bp kanamycin resistance gene, and a 68 bp polylinker, followed by vector cleaving by SalI and BamHI restriction endonucleases and ligation with promoter and regulatory region: a site containing the promoter region of a 352 bp human myoglobin gene is used for the production of the gene therapy DNA vector GDTT1.8NAS1 for targeted gene therapy, a site containing the promoter region of a 270 bp human elastase gene is used for the production of the gene therapy DNA vector GDTT1.8NAS2 for targeted gene therapy, a site containing the promoter region of a 399 bp human intercellular adhesion molecule gene 2 is used for the production of the gene therapy DNA vector GDTT1.8NAS3 for targeted gene therapy, a site containing the promoter region of a 569 bp human osteocalcin 2 gene is used for the production of the gene therapy DNA vector GDTT1.8NAS4 for targeted gene therapy, a site containing the promoter region of a 635 bp human surfactant protein B gene is used for the production of the gene therapy DNA vector GDTT1.8NAS5 for targeted gene therapy, a site containing the promoter region of a 556 bp human synapsin I protein gene is used for the production of the gene therapy DNA vector GDTT1.8NAS6 for targeted gene therapy, a site containing the promoter region of a 1236 bp human nephrine gene is used for the production of the gene therapy DNA vector GDTT1.8NAS7 for targeted gene therapy, a site containing the promoter region of a 856 bp human common leukocyte antigen CD45 gene is used for the production of the gene therapy DNA vector GDTT1.8NAS8 for targeted gene therapy, a site containing the promoter region of a 1220 bp human B29 protein gene is used for the production of the gene therapy DNA vector GDTT1.8NAS9 for targeted gene therapy, a site containing the promoter region of a 658 bp human CD68 protein gene is used for the production of the gene therapy DNA vector GDTT1.8NAS10 for targeted gene therapy, a site containing the promoter region of a 594 bp human insulin gene is used for the production of the gene therapy DNA vector GDTT1.8NAS11 for targeted gene therapy, and then cleaving of the kanamycin resistance gene by SpeI restriction sites.

A method of production of *Escherichia coli* strain JM110-NAS has been developed for the production of the gene therapy DNA vector selected from: GDTT1.8NAS1, or GDTT1.8NAS2, or GDTT1.8NAS3, or GDTT1.8NAS4, or GDTT1.8NAS5, or GDTT1.8NAS6, or GDTT1.8NAS7, or GDTT1.8NAS8, or GDTT1.8NAS9, or GDTT1.8NAS10, or GDTT1.8NAS11 that involves constructing a linear DNA fragment containing a regulatory element RNA-in of Tn10 transposon allowing for antibiotic-free positive selection (64 bp), levansucrase gene sacB, the product of which ensures selection within a sucrose-containing medium (1422 bp), chloramphenicol resistance gene catR, required to pick strain clones where homologous recombination occurred (763 bp), and two homologous sequences (329 bp and 233 bp) ensuring homologous recombination in the region of gene recA concurrent with gene inactivation, where the said homologous sequences are obtained by PCR amplification of gene recA fragment using genome DNA of *Escherichia coli* JM110-NAS as a matrix, and a pair of LHA-F (5'-GCTGACGCTGCAGGTGATC) and LHA-R (5'-GACAA-GATGTGTGTCTACCGCTTCAGGTTACCCGCCAG) primers, and a pair of RHA-F (5'-TGGCAGGGCGGGGCGTAAC-TACGCCTCTGTTCGTCTCGA) and RHA-R (5'-CTCAGCAGCAACTCACGTAC) primers, and then the *Escherichia coli* cells are transformed by electroporation, and clones surviving in a medium containing 10 μg/ml of chloramphenicol are selected.

*Escherichia coli* strain JM110-NAS was produced for the production of the gene therapy DNA vector selected from GDTT1.8NAS1, or GDTT1.8NAS2, or GDTT1.8NAS3, or GDTT1.8NAS4, or GDTT1.8NAS5, or GDTT1.8NAS6, or GDTT1.8NAS7, or GDTT1.8NAS8, or GDTT1.8NAS9, or GDTT1.8NAS10, or GDTT1.8NAS11 that allows for antibiotic-free positive selection and containing a linear fragment consisting of regulator element RNA-in of transposon Tn10, levansucrose gene sacB and chloramphenicol resistance gene catR in the chromosome in recA gene region.

A method of obtaining strain carrying a gene therapy DNA vector selected from GDTT1.8NAS1, or GDTT1.8NAS2, or GDTT1.8NAS3, or GDTT1.8NAS4, or GDTT1.8NAS5, or GDTT1.8NAS6, or GDTT1.8NAS7, or GDTT1.8NAS8, or GDTT1.8NAS9, or GDTT1.8NAS10, or GDTT1.8NAS11, namely: *Escherichia coli* JM-110-NAS-GDTT1.8NAS1, or *Escherichia coli* JM-110-NAS-GDTT1.8NAS2, or *Escherichia coli* JM-110-NAS-GDTT1.8NAS3, or *Escherichia coli* JM-110-NAS-GDTT1.8NAS4, or *Escherichia coli* JM-110-NAS-GDTT1.8NAS5, or *Escherichia coli* JM-110-NAS-GDTT1.8NAS6, or *Escherichia coli* JM-110-NAS-GDTT1.8NAS7, or *Escherichia coli* JM-110-NAS-GDTT1.8NAS8, or *Escherichia coli* JM-110-NAS-GDTT1.8NAS9, or *Escherichia coli* JM-110-NAS-GDTT1.8NAS10, or *Escherichia coli* JM-110-NAS-GDTT1.8NAS11 has been developed that involves making electrocompetent cells of *Escherichia coli* strain JM110-NAS and subjecting these cells to electroporation with gene therapy DNA vector GDTT1.8NAS1, or GDTT1.8NAS2, or GDTT1.8NAS3, or GDTT1.8NAS4, or GDTT1.8NAS5, or GDTT1.8NAS6, or GDTT1.8NAS7, or GDTT1.8NAS8, or GDTT1.8NAS9, or GDTT1.8NAS10, or GDTT1.8NAS11. After that, the cells are poured into agar plates (Petri dishes) with a selective medium containing yeastrel, peptone, 6% sucrose, and 10 μg/ml of chloramphenicol for the selection of stable strain clones.

*Escherichia coli* strain JM-110-NAS-GDTT1.8NAS1 carrying the gene therapy DNA vector GDTT1.8NAS1 for the gene therapy DNA vector GDTT1.8NAS1 production allowing for antibiotic-free selection, *Escherichia coli* strain JM-110-NAS-GDTT1.8NAS2 carrying the gene therapy DNA vector GDTT1.8NAS2 for the gene therapy DNA vector GDTT1.8NAS2 production allowing for antibiotic-free selection, *Escherichia coli* strain JM-110-NAS-GDTT1.8NAS3 carrying the gene therapy DNA vector GDTT1.8NAS3 for the gene therapy DNA vector GDTT1.8NAS3 production allowing for antibiotic-free selection, *Escherichia coli* strain JM-110-NAS-GDTT1.8NAS4 carrying the gene therapy DNA vector GDTT1.8NAS4 for the gene therapy DNA vector GDTT1.8NAS4 production allowing for antibiotic-free selection, *Escherichia coli* strain JM-110-NAS-GDTT1.8NAS5 carrying the gene therapy DNA vector GDTT1.8NAS5 for the gene therapy DNA vector GDTT1.8NAS5 production allowing for antibiotic-free selection, *Escherichia coli* strain JM-110-NAS-GDTT1.8NAS6 carrying the gene therapy DNA vector GDTT1.8NAS6 for the gene therapy DNA vector GDTT1.8NAS6 production allowing for antibiotic-free selection, *Escherichia coli* strain JM-110-NAS-GDTT1.8NAS7 carrying the gene therapy DNA vector GDTT1.8NAS7 for the gene therapy DNA vector GDTT1.8NAS7 production allowing for antibiotic-free selection, *Escherichia coli* strain JM-110-NAS-GDTT1.8NAS8 carrying the gene therapy DNA vector GDTT1.8NAS8 for the gene therapy DNA vector GDTT1.8NAS8 production allowing for antibiotic-free selection, *Escherichia coli* strain JM-110-NAS-GDTT1.8NAS9 carrying the gene therapy DNA vector GDTT1.8NAS9 for the gene therapy DNA vector GDTT1.8NAS9 production allowing for antibiotic-free selection, *Escherichia coli* strain JM-110-NAS-GDTT1.8NAS10 carrying the gene therapy DNA vector GDTT1.8NAS10 for the gene therapy DNA vector GDTT1.8NAS10 production allowing for antibiotic-free selection, *Escherichia coli* strain JM-110-NAS-GDTT1.8NAS11 carrying the gene therapy DNA vector GDTT1.8NAS11 for the gene therapy DNA vector GDTT1.8NAS11 production allowing for antibiotic-free selection were produced.

A method of gene therapy DNA vector production on an industrial scale has been developed that involves scaling-up the bacterial culture to the quantities necessary for increasing the bacterial biomass in an industrial fermenter, after which the biomass is used to extract a fraction containing the therapeutic DNA product, i.e. the gene therapy DNA vector GDTT1.8NAS1, or GDTT1.8NAS2, or GDTT1.8NAS3, or GDTT1.8NAS4, or GDTT1.8NAS5, or GDTT1.8NAS6, or GDTT1.8NAS7, or GDTT1.8NAS8, or GDTT1.8NAS9, or GDTT1.8NAS10, or GDTT1.8NAS11, and then multi-stage filtered, and purified by chromatographic methods.

A method of selection of gene therapy DNA vector GDTT1.8NAS1, or GDTT1.8NAS2, or GDTT1.8NAS3, or GDTT1.8NAS4, or GDTT1.8NAS5, or GDTT1.8NAS6, or GDTT1.8NAS7, or GDTT1.8NAS8, or GDTT1.8NAS9, or GDTT1.8NAS10, or GDTT1.8NAS11 for targeted gene therapy has been developed, while each of said vectors contains different tissue-specific promoter and regulatory regions of the human gene in order to construct the appropriate tissue-specific gene therapy DNA vector containing the therapeutic gene, ensure effective expression of this therapeutic gene exclusively in the target cell line, human target tissue due to the presence of a promoter and regulatory region that is tissue specific for only this target cell line, the human target tissue in the gene therapy DNA vector. Said method involves selection of gene therapy DNA vector GDTT1.8NAS1 for the construction of gene therapy DNA vector containing a therapeutic gene for targeted gene therapy aimed at increasing the expression level of this therapeutic gene in the muscle tissue cells, selection of gene therapy DNA vector GDTT1.8NAS2 for the construction of gene therapy DNA vector containing a therapeutic gene for targeted gene therapy aimed at increasing the expression level of this therapeutic gene in the skin cells, selection of gene therapy DNA vector GDTT1.8NAS3 for the construction of gene therapy DNA vector containing a therapeutic gene for targeted gene therapy aimed at increasing the expression level of this therapeutic gene in the vascular endothelial cells, selection of gene therapy DNA vector GDTT1.8NAS4 for the construction of gene therapy DNA vector containing a therapeutic gene for targeted gene therapy aimed at increasing the expression level of this therapeutic gene the bone cells, namely in osteoblasts and odontoblasts, selection of gene therapy DNA vector GDTT1.8NAS5 for the construction of gene therapy DNA vector containing a therapeutic gene for targeted gene therapy aimed at increasing the expression level of this therapeutic gene in bronchi and alveoli epithelial cells, selection of gene therapy DNA vector GDTT1.8NAS6 for the construction of gene therapy DNA vector containing a therapeutic gene for targeted gene therapy aimed at increasing the expression level of this therapeutic gene in the cells of nervous tissue, namely in neurons, selection of gene therapy DNA vector GDTT1.8NAS7 for the construction of gene therapy DNA vector containing a therapeutic gene for targeted gene therapy aimed at increasing the expression level of this therapeutic gene in the kidney cells, namely in podocytes, selection of gene therapy DNA vector GDTT1.8NAS8 for the construction of gene therapy DNA vector containing a therapeutic gene for targeted gene therapy aimed at increasing the expression level of this therapeutic gene in the blood cells, namely in hematopoietic blood cells, selection of gene therapy DNA vector GDTT1.8NAS9 for the construction of gene therapy DNA vector containing a therapeutic gene for targeted gene therapy aimed at increasing the expression level of this therapeutic gene in the blood cells, namely in lymphocytes, selection of gene therapy DNA vector GDTT1.8NAS10 for the construction of gene therapy DNA vector containing a therapeutic gene for targeted gene therapy aimed at increasing the expression level of this therapeutic gene in the blood cells, namely in macrophages, selection of gene therapy DNA vector GDTT1.8NAS11 for the construction of gene therapy DNA vector containing a therapeutic gene for targeted gene therapy aimed at increasing the expression level of this therapeutic gene in cells of pancreas, namely in beta cells of pancreas.

The essence of the invention is explained in the drawings, where

FIG. 1 shows the structure of gene therapy DNA vector GDTT1.8NAS1 that is a 1736 bp circular double-strand DNA molecule capable of autonomous replication in *Escherichia coli* cells without selective antibiotic in the culture medium.

FIG. 1 marks the following structural elements of the vector:
(1) pUCori (1 to 688 bp) is an origin of replication with a single nucleotide substitution to increase plasmid production, which serves for autonomous replication in *Escherichia coli* cells.
(2) prom (695 to 1046 bp) is the promoter region of human myoglobin gene. It serves to provide a high specific level of therapeutic gene transcription in muscle cells of different organs of the human body.
(3) MCS (1047 to 1114 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1115 to 1581 bp) is the transcription terminator and the polyadenylation sequence of the human growth factor gene;
(5) RNA-out (1588 to 1724 bp) is a regulatory element RNA-out of transposon Tn10 allowing for antibiotic-free positive selection in case of the use of *Escherichia coli* strain JM110-NAS.

Figure 2:
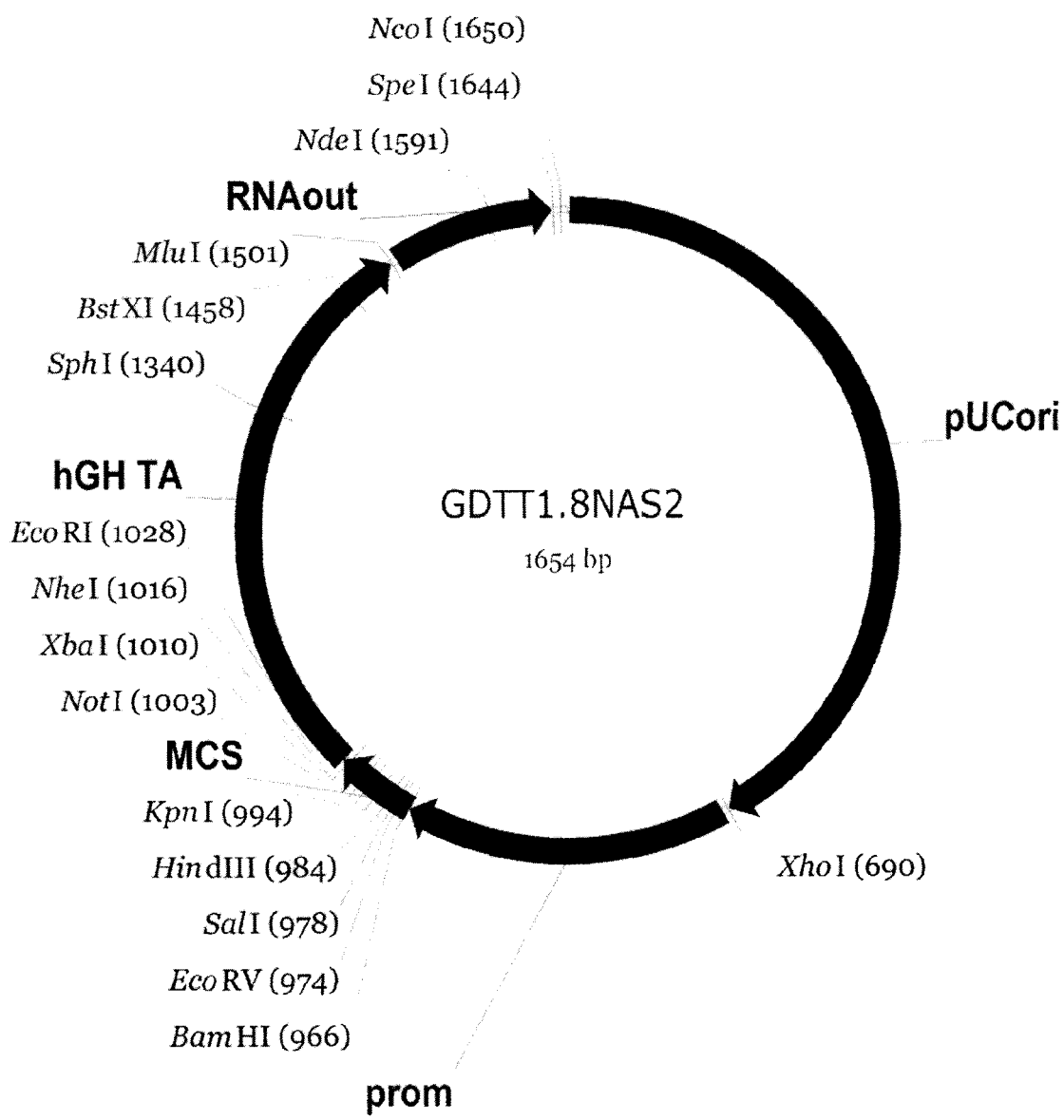

FIG. 2 shows the structure of gene therapy DNA vector GDTT1.8NAS2 that is a 1654 bp circular double-strand DNA molecule capable of autonomous replication in *Escherichia coli* cells without selective antibiotic in the culture medium.

FIG. 2 marks the following structural elements of the vector:
(1) pUCori (1 to 688 bp) is an origin of replication with a single nucleotide substitution to increase plasmid production, which serves for autonomous replication in *Escherichia coli* cells.
(2) prom (695 to 964 bp) is the promoter region of human elastase gene. It serves to provide a high specific level of therapeutic gene transcription in the human skin cells.
(3) MCS (965 to 1032 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1033 to 1499 bp) is the transcription terminator and the polyadenylation sequence of the human growth factor gene;
(5) RNA-out (1506 to 1642 bp) is a regulatory element RNA-out of transposon Tn10 allowing for antibiotic-free positive selection in case of the use of *Escherichia coli* strain JM110-NAS.

Figure 3:
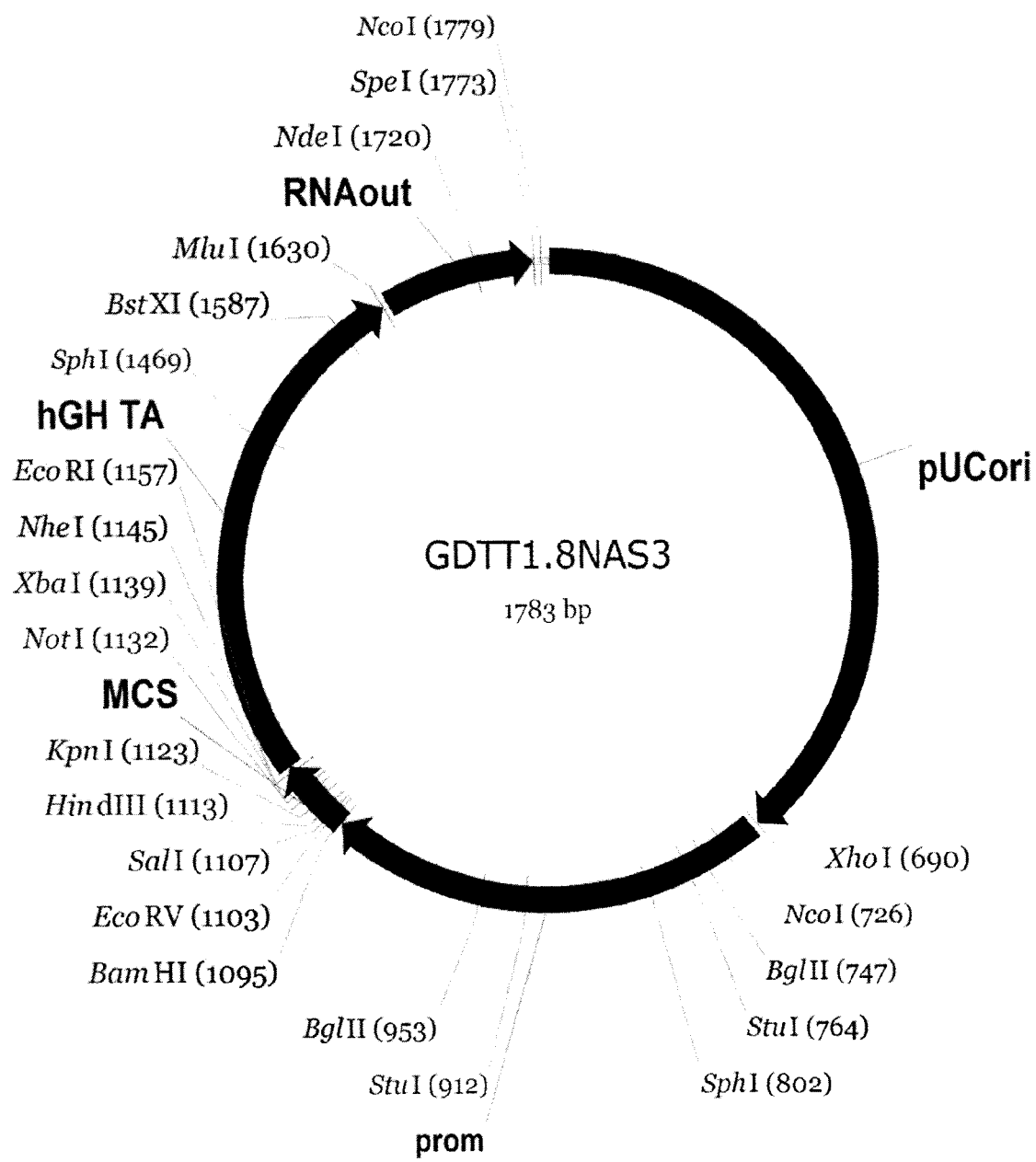

FIG. 3 shows the structure of gene therapy DNA vector GDTT1.8NAS3 that is a 1783 bp circular double-strand DNA molecule capable of autonomous replication in *Escherichia coli* cells without selective antibiotic in the culture medium.

FIG. 3 marks the following structural elements of the vector:
(1) pUCori (1 to 688 bp) is an origin of replication with a single nucleotide substitution to increase plasmid production, which serves for autonomous replication in *Escherichia coli* cells.
(2) prom (695 to 1093 bp) is the promoter region of the human intercellular adhesion molecule gene 2. It serves to provide a high specific level of therapeutic gene transcription in the vascular endothelial cells.
(3) MCS (1094 to 1161 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1162 to 1628 bp) is the transcription terminator and the polyadenylation sequence of the human growth factor gene;
(5) RNA-out (1635 to 1771 bp) is a regulatory element RNA-out of transposon Tn10 allowing for antibiotic-free positive selection in case of the use of *Escherichia coli* strain JM110-NAS.

Figure 4:
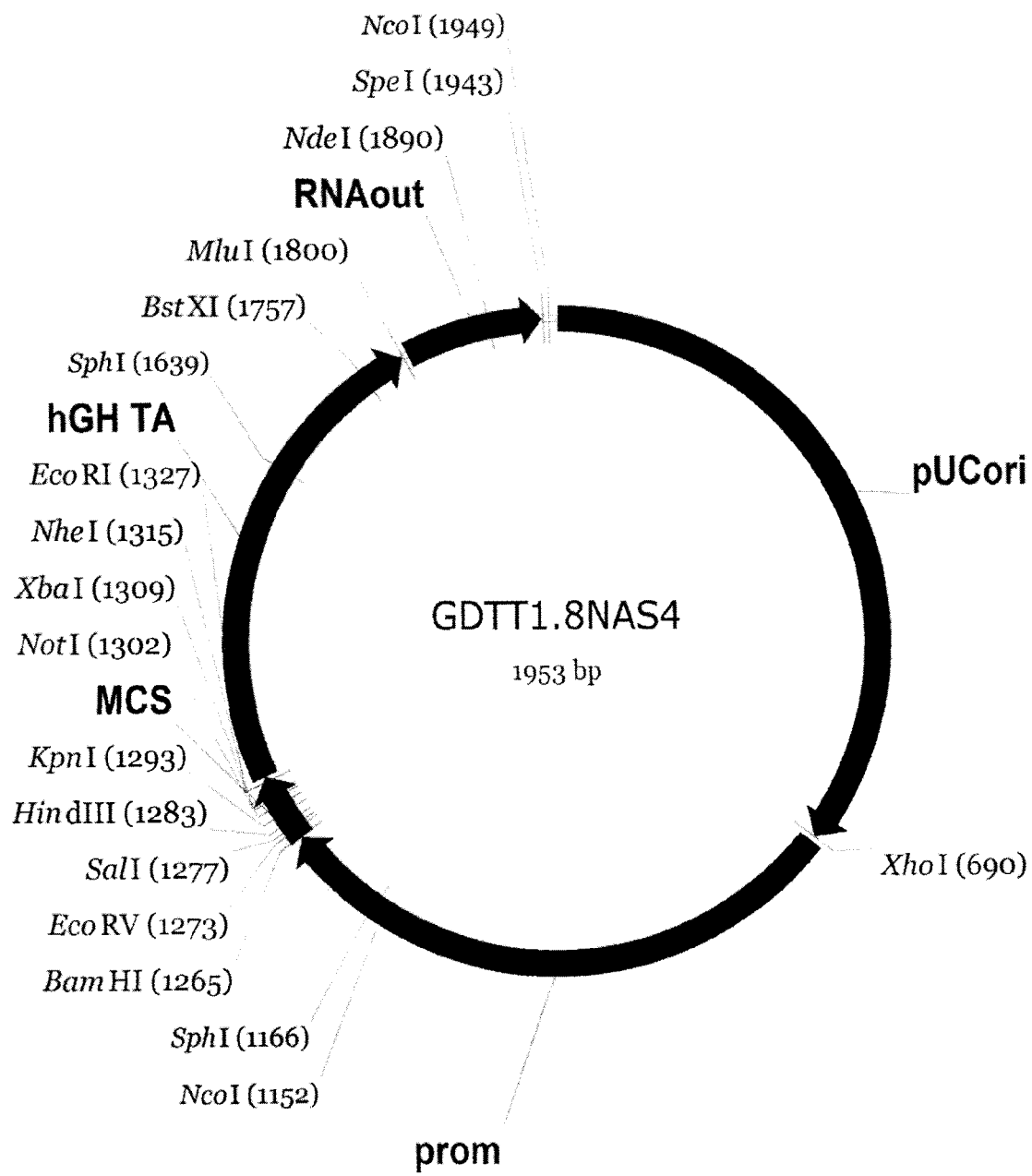

FIG. 4 shows the structure of gene therapy DNA vector GDTT1.8NAS4 that is a 1953 bp circular double-strand DNA molecule capable of autonomous replication in *Escherichia coli* cells without selective antibiotic in the culture medium.

FIG. 4 marks the following structural elements of the vector:
(1) pUCori (1 to 688 bp) is an origin of replication with a single nucleotide substitution to increase plasmid production, which serves for autonomous replication in *Escherichia coli* cells.
(2) prom (695 to 1263 bp) is the promoter region of human osteocalcin gene 2. It serves to provide a high specific level of therapeutic gene transcription in osteoblasts and odontoblasts.

(3) MCS (1264 to 1331 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1332 to 1798 bp) is the transcription terminator and the polyadenylation sequence of the human growth factor gene;
(5) RNA-out (1805 to 1941 bp) is a regulatory element RNA-out of transposon Tn10 allowing for antibiotic-free positive selection in case of the use of Escherichia coli strain JM110-NAS.

Figure 5:
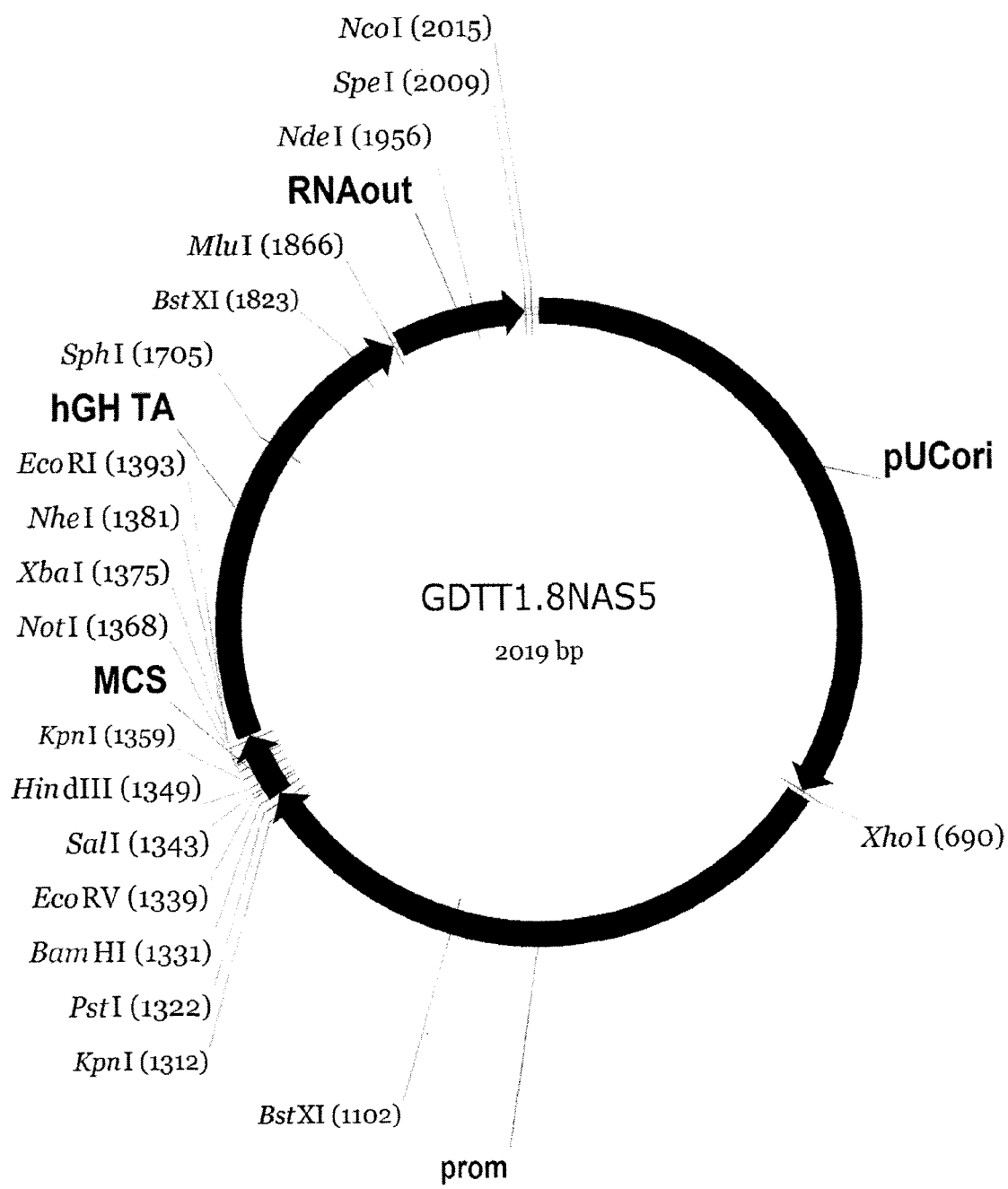

FIG. 5 shows the structure of gene therapy DNA vector GDTT1.8NAS5 that is a 2019 bp circular double-strand DNA molecule capable of autonomous replication in Escherichia coli cells without selective antibiotic in the culture medium.

FIG. 5 marks the following structural elements of the vector:
(1) pUCori (1 to 688 bp) is an origin of replication with a single nucleotide substitution to increase plasmid production, which serves for autonomous replication in Escherichia coli cells.
(2) prom (695 to 1329 bp) is the promoter region of surfactant protein B gene. It serves to provide a high specific level of therapeutic gene transcription in bronchi and alveoli epithelial cells.
(3) MCS (1330 to 1397 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1398 to 1864 bp) is the transcription terminator and the polyadenylation sequence of the human growth factor gene;
(5) RNA-out (1871 to 2007 bp) is a regulatory element RNA-out of transposon Tn10 allowing for antibiotic-free positive selection in case of the use of Escherichia coli strain JM110-NAS.

Figure 6:
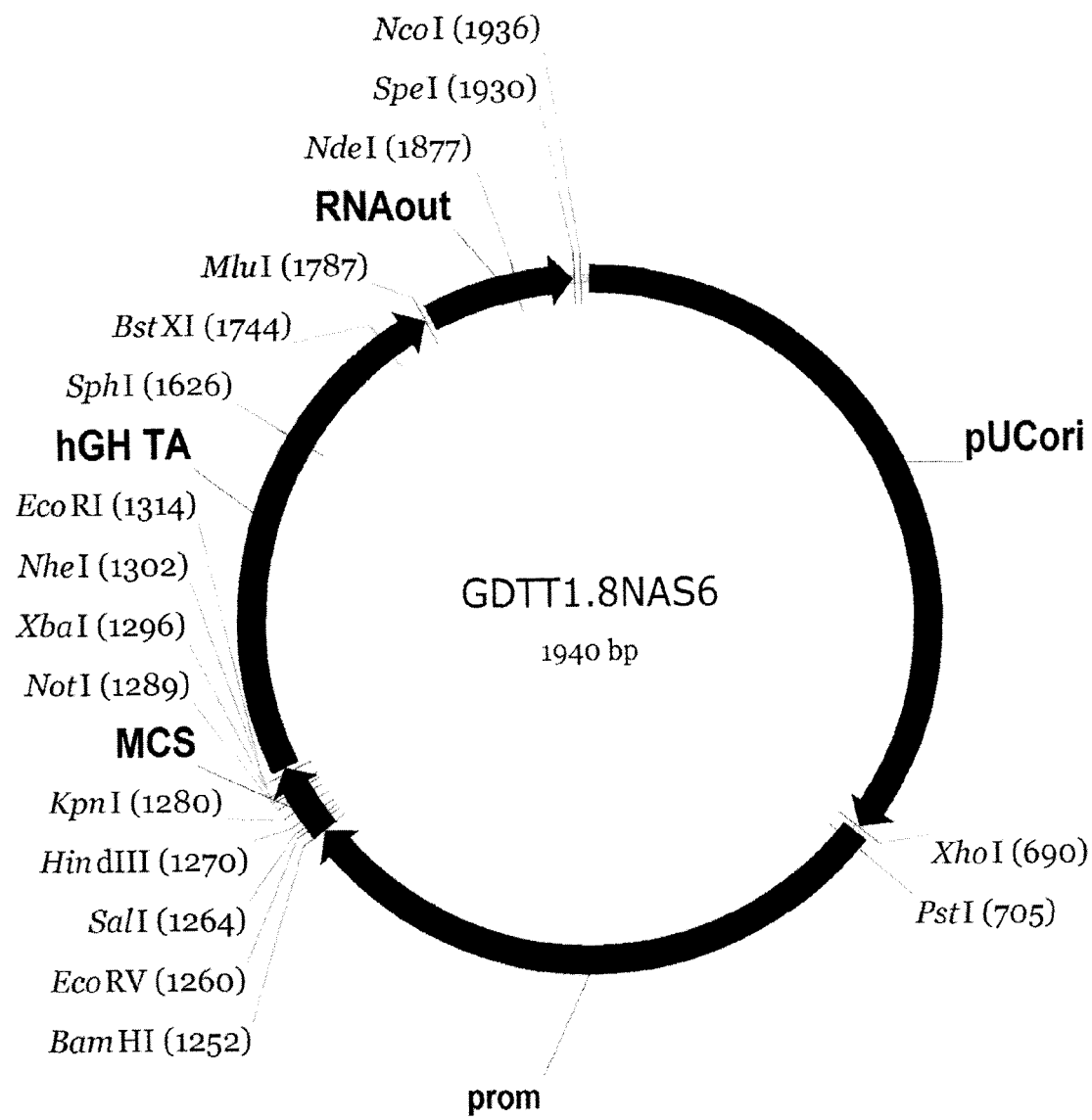

FIG. 6 shows the structure of gene therapy DNA vector GDTT1.8NAS6 that is a 1940 bp circular double-strand DNA molecule capable of autonomous replication in Escherichia coli cells without selective antibiotic in the culture medium.

FIG. 6 marks the following structural elements of the vector:
(1) pUCori (1 to 688 bp) is an origin of replication with a single nucleotide substitution to increase plasmid production, which serves for autonomous replication in Escherichia coli cells.
(2) prom (695 to 1250 bp) is the promoter region of human synapsin I gene. It serves to provide a high specific level of therapeutic gene transcription in neurons.
(3) MCS (1251 to 1318 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1319 to 1785 bp) is the transcription terminator and the polyadenylation sequence of the human growth factor gene;
(5) RNA-out (1792 to 1928 bp) is a regulatory element RNA-out of transposon Tn10 allowing for antibiotic-free positive selection in case of the use of Escherichia coli strain JM110-NAS.

Figure 7:
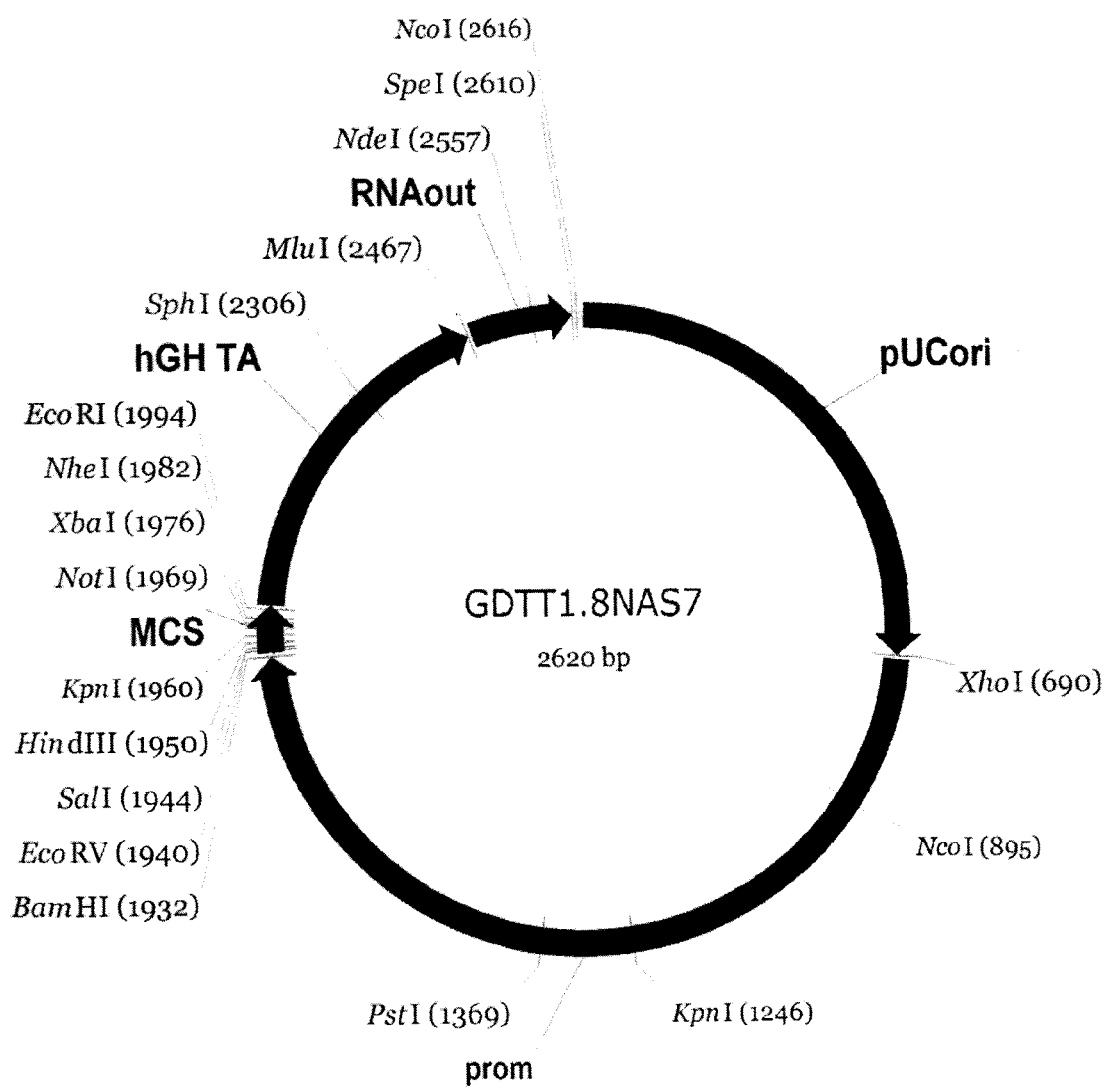

FIG. 7 shows the structure of gene therapy DNA vector GDTT1.8NAS7 that is a 2620 bp circular double-strand DNA molecule capable of autonomous replication in Escherichia coli cells without selective antibiotic in the culture medium.

FIG. 7 marks the following structural elements of the vector:
(1) pUCori (1 to 688 bp) is an origin of replication with a single nucleotide substitution to increase plasmid production, which serves for autonomous replication in Escherichia coli cells.
(2) prom (695-1930 to 1046 bp) is the promoter region of human nephrin gene. It serves to provide a high specific level of therapeutic gene transcription in renal podocytes.
(3) MCS (1937 to 1998 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1999 to 2465 bp) is the transcription terminator and the polyadenylation sequence of the human growth factor gene;
(5) RNA-out (2472 to 2608 bp) is a regulatory element RNA-out of transposon Tn10 allowing for antibiotic-free positive selection in case of the use of Escherichia coli strain JM110-NAS.

Figure 8:
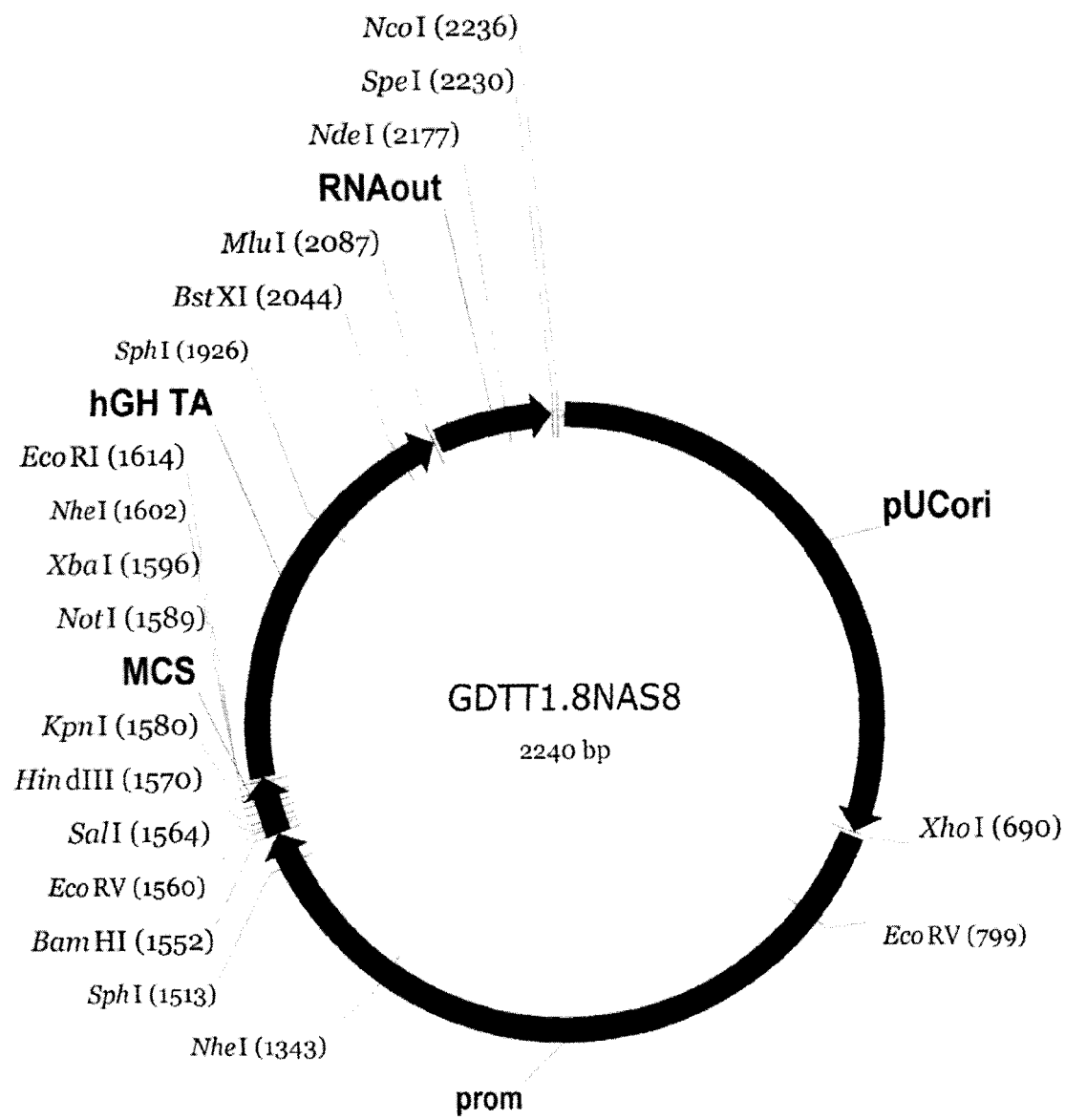

FIG. 8 shows the structure of gene therapy DNA vector GDTT1.8NAS8 that is a 2240 bp circular double-strand DNA molecule capable of autonomous replication in Escherichia coli cells without selective antibiotic in the culture medium.

FIG. 8 marks the following structural elements of the vector:
(1) pUCori (1 to 688 bp) is an origin of replication with a single nucleotide substitution to increase plasmid production, which serves for autonomous replication in Escherichia coli cells.
(2) prom (695 to 1550 bp) is the promoter region of the human common leukocyte antigen CD45 gene. It serves to provide a high specific level of therapeutic gene transcription in hematopoietic cells.
(3) MCS (1551 to 1618 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1619 to 2085 bp) is the transcription terminator and the polyadenylation sequence of the human growth factor gene;
(5) RNA-out (2092 to 2228 bp) is a regulatory element RNA-out of transposon Tn10 allowing for antibiotic-free positive selection in case of the use of Escherichia coli strain JM110-NAS.

Figure 9:
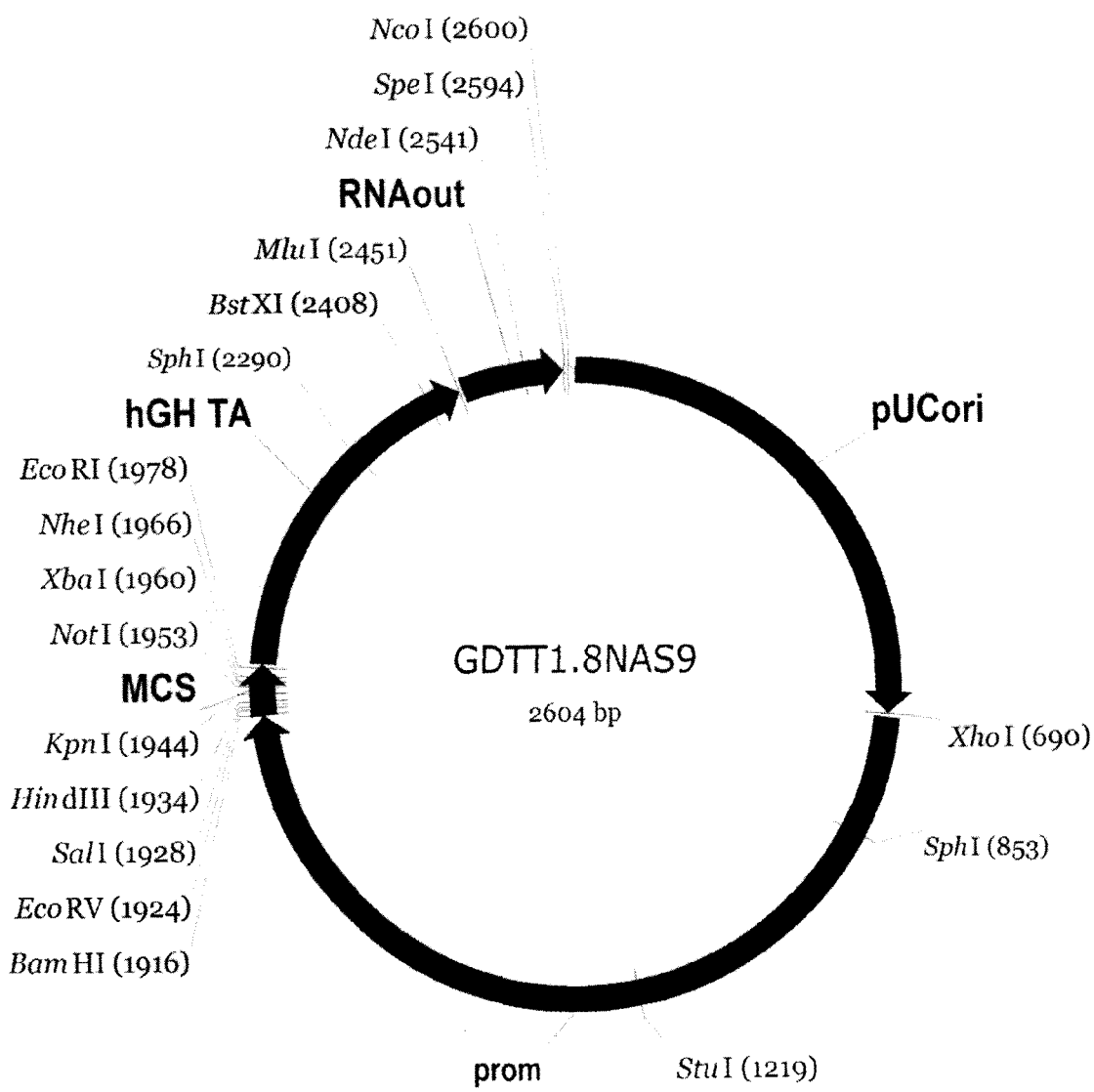

FIG. 9 shows the structure of gene therapy DNA vector GDTT1.8NAS9 that is a 2604 bp circular double-strand DNA molecule capable of autonomous replication in Escherichia coli cells without selective antibiotic in the culture medium.

FIG. 9 marks the following structural elements of the vector:
(1) pUCori (1 to 688 bp) is an origin of replication with a single nucleotide substitution to increase plasmid production, which serves for autonomous replication in Escherichia coli cells.
(2) prom (695 to 1914 bp) is the promoter region of human B29 protein gene. It serves to provide a high specific level of therapeutic gene transcription in lymphocytes.
(3) MCS (1915 to 1982 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1983 to 2449 bp) is the transcription terminator and the polyadenylation sequence of the human growth factor gene;

(5) RNA-out (2456 to 2592 bp) is a regulatory element RNA-out of transposon Tn10 allowing for antibiotic-free positive selection in case of the use of *Escherichia coli* strain JM110-NAS.

Figure 10:
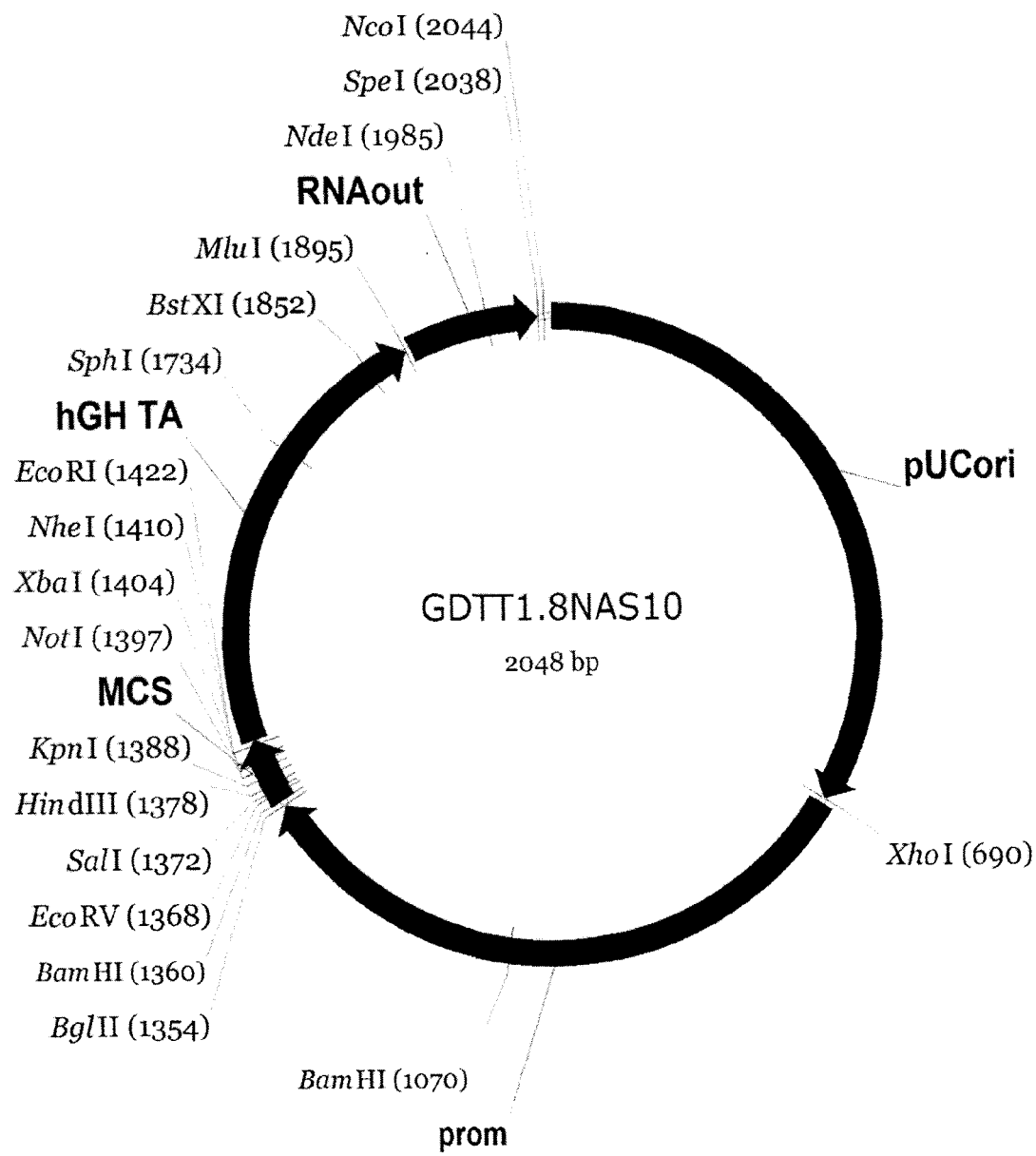

FIG. 10 shows the structure of gene therapy DNA vector GDTT1.8NAS10 that is a 2048 bp circular double-strand DNA molecule capable of autonomous replication in *Escherichia coli* cells without selective antibiotic in the culture medium.

FIG. 10 marks the following structural elements of the vector:
(1) pUCori (1 to 688 bp) is an origin of replication with a single nucleotide substitution to increase plasmid production, which serves for autonomous replication in *Escherichia coli* cells.
(2) prom (695 to 1352 bp) is the promoter region of human CD68 protein gene. It serves to provide a high specific level of therapeutic gene transcription in macrophages.
(3) MCS (1359 to 1426 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1427 to 1893 bp) is the transcription terminator and the polyadenylation sequence of the human growth factor gene;
(5) RNA-out (1900 to 2036 bp) is a regulatory element RNA-out of transposon Tn10 allowing for antibiotic-free positive selection in case of the use of *Escherichia coli* strain JM110-NAS.

Figure 11:
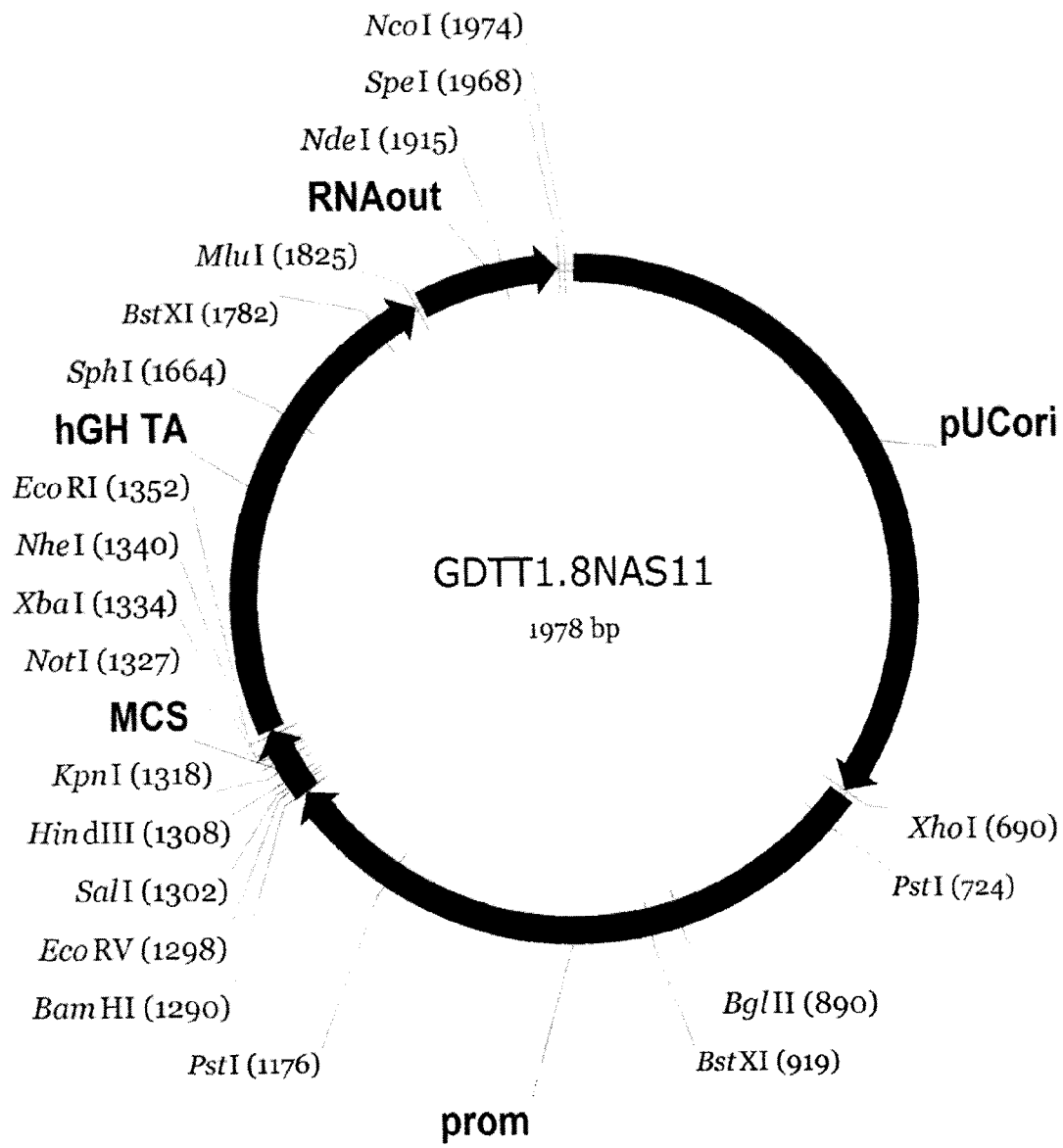

FIG. 11 shows the structure of gene therapy DNA vector GDTT1.8NAS11 that is a 1978 bp circular double-strand DNA molecule capable of autonomous replication in *Escherichia coli* cells without selective antibiotic in the culture medium.

FIG. 11 marks the following structural elements of the vector:
(1) pUCori (1 to 688 bp) is an origin of replication with a single nucleotide substitution to increase plasmid production, which serves for autonomous replication in *Escherichia coli* cells.
(2) prom (695-1288 to 1046 bp) is the promoter region of human insulin gene. It serves to provide a high specific level of therapeutic gene transcription in beta cells of pancreas.
(3) MCS (1289 to 1356 bp) is a polylinker (multiple cloning site) that contains BamHI, EcoRV, SalI, KpnI, EcoRI, XbaI, and NotI restriction sites and allows cloning of the therapeutic therapy genes.
(4) hGH-TA (1357 to 1823 bp) is the transcription terminator and the polyadenylation sequence of the human growth factor gene;
(5) RNA-out (1830 to 1966 bp) is a regulatory element RNA-out of transposon Tn10 allowing for antibiotic-free positive selection in case of the use of *Escherichia coli* strain JM110-NAS.

Figure 12:
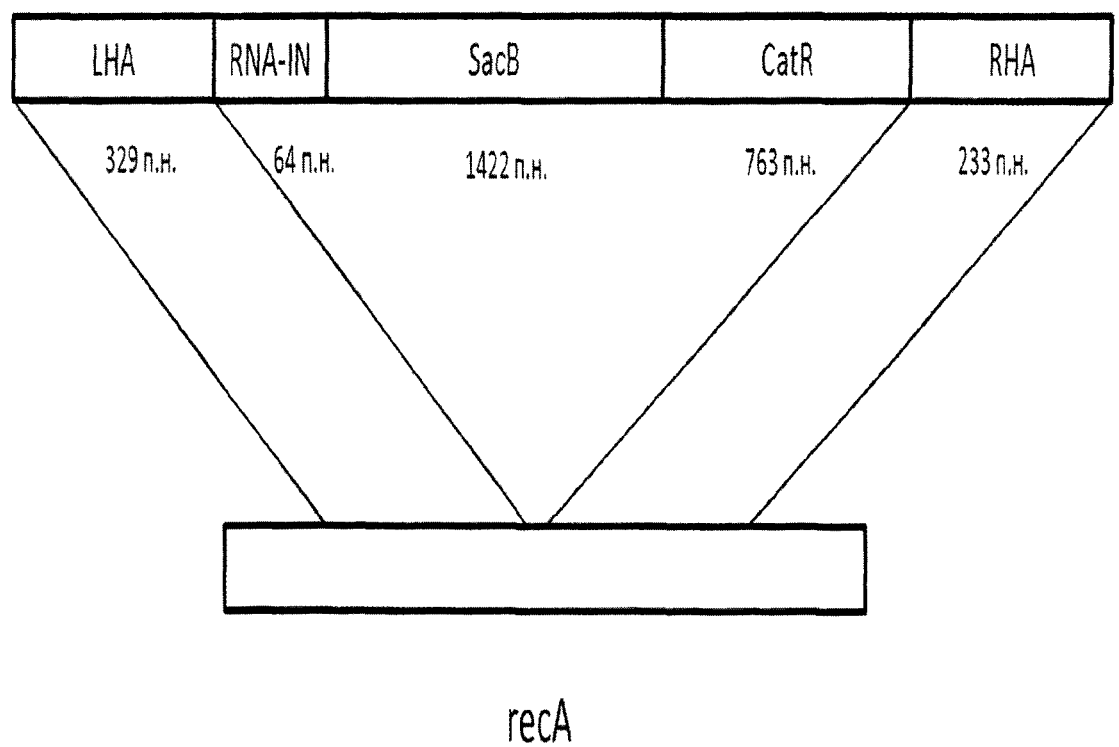

FIG. 12 shows the structure of the DNA fragment for homologous recombination in the region of recA gene of *Escherichia coli* for obtaining *Escherichia coli* strain JM 110, where: RNA-in is a linear fragment consisting of a cassette carrying the regulatory element RNA-in of transposon Tn10 for antibiotic-free selection (64 bp),
sacB is the sacB levansucrase gene, which product provides selection in the sucrose-containing medium (1422 bp),
catR is the catR chloramphenicol resistance gene necessary for selection of strain clones with homologous recombination (763 bp).
LHA and RHA—the cassette is flanked by two homology arms that ensure the process of recombination in the region of recA gene with concurrent gene inactivation (329 bp and 233 bp for the left arm and for the right arm, respectively).

Figure 13:
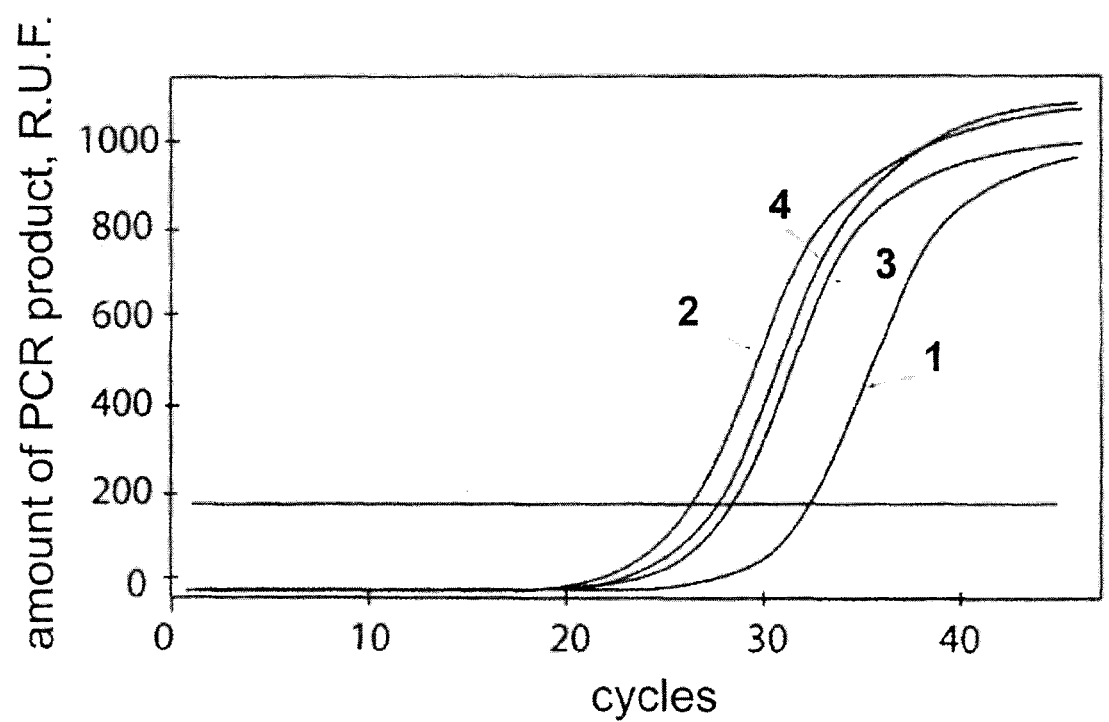

FIG. 13 shows diagrams of human VEGF mRNA accumulation in human skeletal myoblasts HSkM before their transfection and 48 hours after transfection of these cells with DNA vector GDTT1.8NAS1-VEGF carrying the human VEGF gene in order to assess changes in the mRNA accumulation of therapeutic gene, for example, the VEGF gene, in human skeletal myoblasts HSkM before their transfection and 48 hours after transfection of these cells with DNA vector GDTT1.8NAS1-VEGF carrying the human VEGF gene, where:
1—cDNA of VEGF gene after transfection with gene therapy vector GDTT1.8NAS1;
2—cDNA of VEGF gene after transfection with gene therapy vector GDTT1.8NAS1-VEGF carrying the human VEGF gene;
3—cDNA of B2M gene after transfection with gene therapy vector GDTT1.8NAS1;
4—cDNA of B2M gene after transfection with gene therapy vector GDTT1.8NAS1-VEGF carrying the human VEGF gene.

Figure 14:
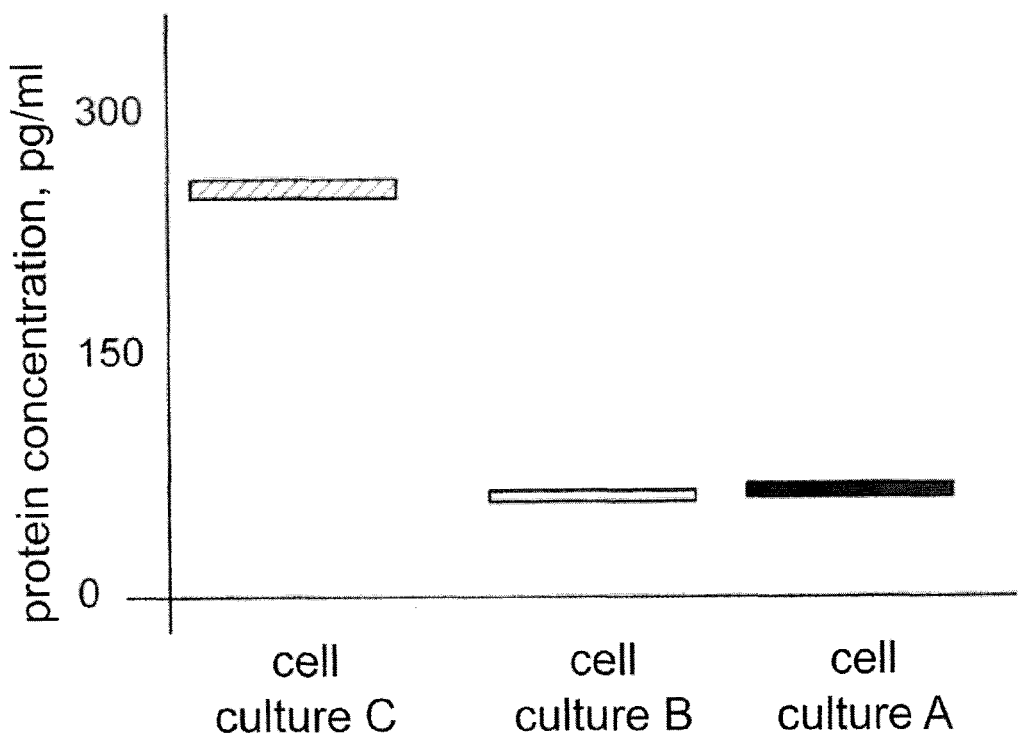

FIG. 14 shows the plot of VEGF protein concentration in the Human skeletal myoblast lysate HSkM upon transfection of these cells with the gene therapy DNA vector GDTT1.8NAS1-VEGF carrying the human VEGF gene and gene therapy DNA vector GDTT1.8NAS1 not carrying the human VEGF gene in order to compare the amount of target protein for example VEGF protein, where:
culture A—HSkM human skeletal myoblast cells transfected without plasmid DNA (reference)
culture B—HSkM human skeletal muscle myoblast cells transfected with DNA vector GDTT1.8NAS1
culture C—HSkM human skeletal muscle myoblast cells transfected with DNA vector GDTT1.8NAS1-VEGF.

Figure 15:
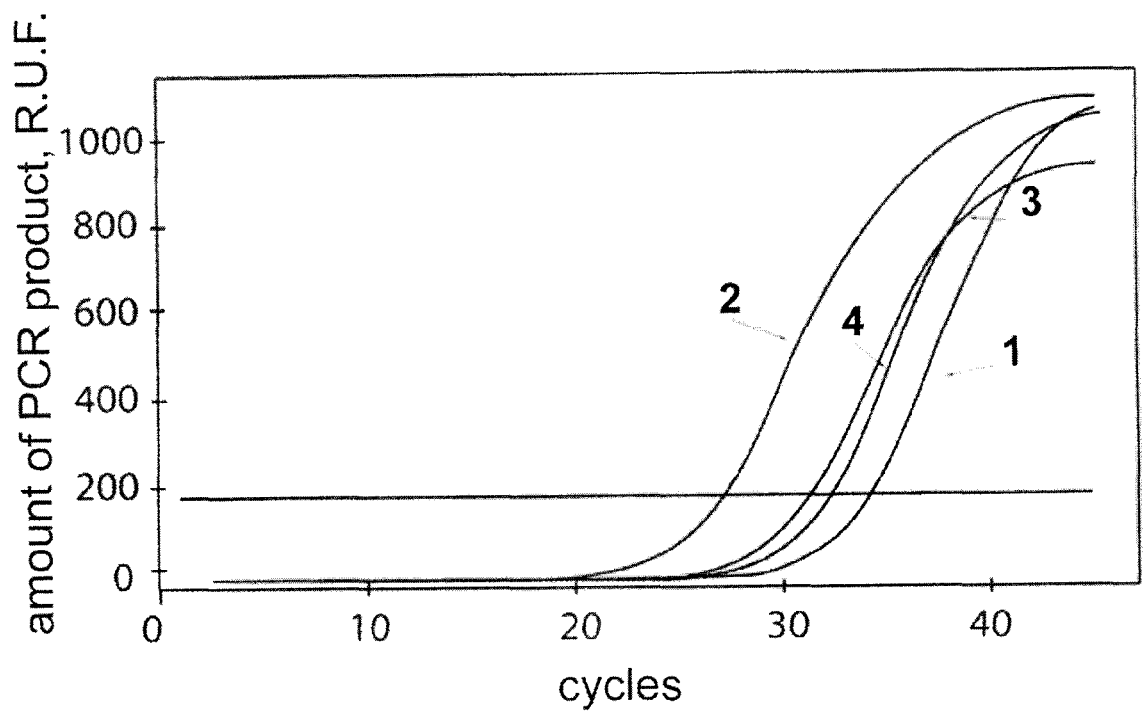

FIG. 15 shows diagrams of human CAT mRNA accumulation in the primary human dermal fibroblast cell culture HDFa before their transfection and 48 hours after transfection of these cells with DNA vector GDTT1.8NAS2-CAT carrying the human CAT gene in order to assess changes in the mRNA accumulation of therapeutic gene, for example, the CAT gene, in the primary human dermal fibroblast cell culture HDFa before their transfection and 48 hours after transfection of these cells with DNA vector GDTT1.8NAS2-CAT carrying the human CAT gene, where:
1—cDNA of CAT gene after transfection with gene therapy vector GDTT1.8NAS2;
2—cDNA of CAT gene after transfection with gene therapy vector GDTT1.8NAS2-CAT carrying the human CAT gene;
3—cDNA of B2M gene after transfection with gene therapy vector GDTT1.8NAS2;
4—cDNA of B2M gene after transfection with gene therapy vector GDTT1.8NAS2-CAT carrying the human CAT gene.

Figure 16:
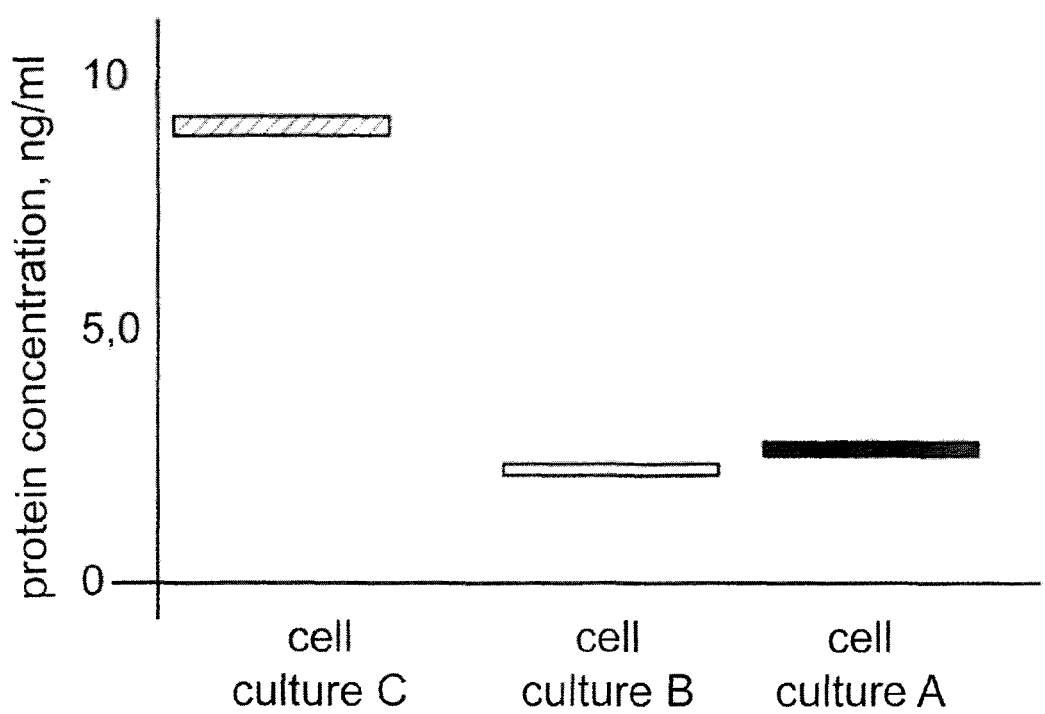
Figure 17:
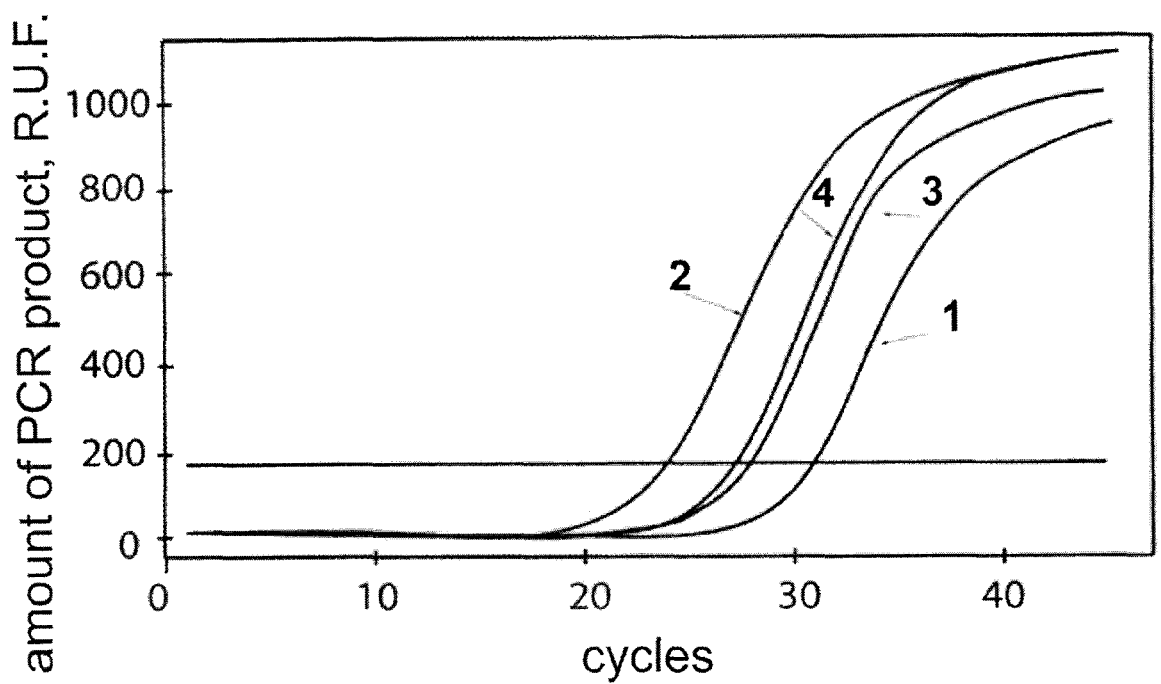

FIG. 16 shows the plot of CAT protein concentration in the primary human dermal fibroblast cell lysate HDFa upon transfection of these cells with the gene therapy DNA vector GDTT1.8NAS2-CAT carrying the human CAT gene and gene therapy DNA vector GDTT1.8NAS2 not carrying the human CAT gene in order to compare the amount of target protein for example CAT protein, where:
culture A—HDFa human primary dermal fibroblast cells transfected with Lipofectamine 3000 without plasmid DNA (reference)
culture B—HDFa human primary dermal fibroblast cells transfected with DNA vector GDTT1.8NAS2
culture C—HDFa human primary dermal fibroblast cells transfected with DNA vector GDTT1.8NAS2-CAT FIG. 17 shows diagrams of human HIF1a mRNA accumulation in umbilical vein endothelial cells HUVEC before their transfection and 48 hours after transfection of these cells with DNA vector GDTT1.8NAS3-HIF1a carrying the human HIF1a gene in order to assess changes in the mRNA accumulation of therapeutic gene, for example, the HIF1a gene, in umbilical vein endothelial cells HUVEC before their transfection and 48 hours after transfection of these cells with DNA vector GDTT1.8NAS3-HIF1a carrying the human HIF1a gene, where:
1—cDNA of HIF1a gene after transfection with gene therapy vector GDTT1.8NAS3;
2—cDNA of HIF1a gene after transfection with gene therapy vector GDTT1.8NAS3-HIF1a carrying the human HIF1a gene;
3—cDNA of B2M gene after transfection with gene therapy vector GDTT1.8NAS3;
4—cDNA of B2M gene after transfection with gene therapy vector GDTT1.8NAS3-HIF1a carrying the human HIF1a gene.

Figure 18:
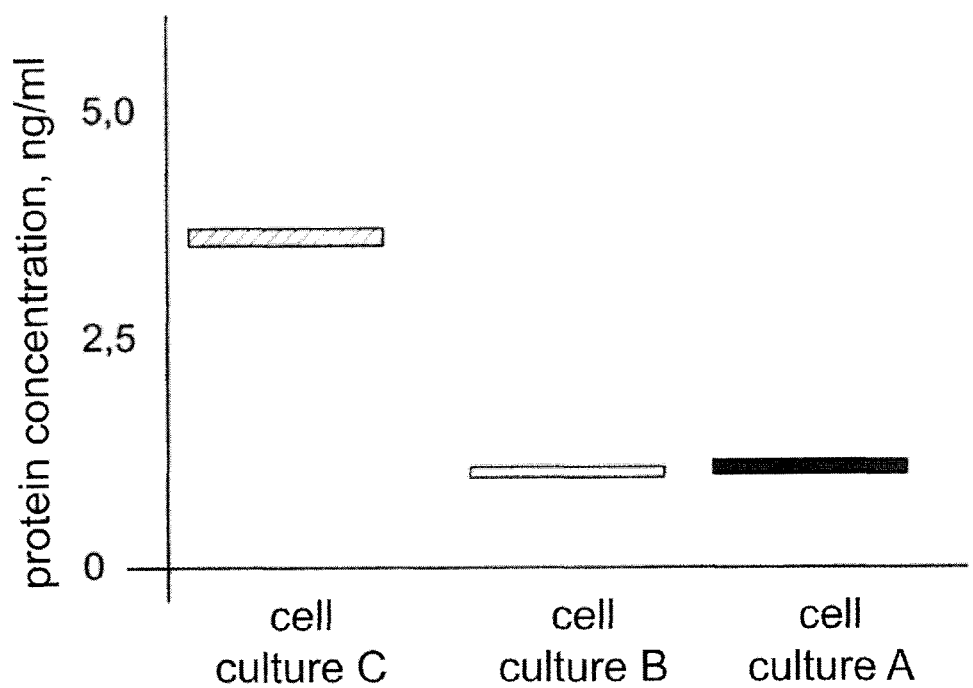

FIG. 18 shows the plot of HIF1a protein concentration in the human umbilical vein endothelial cell lysate HUVEC upon transfection of these cells with the gene therapy DNA vector GDTT1.8NAS3-HIF1a carrying the human CAT gene and gene therapy DNA vector GDTT1.8NAS3 not carrying the human HIF1a gene in order to compare the amount of target protein for example HIF1a protein, where:
culture A—HUVEC human umbilical vein endothelial cell culture transfected with Lipofectamine 3000 without plasmid DNA (reference)
culture B—HUVEC human umbilical vein endothelial cell culture transfected with DNA vector GDTT1.8NAS3
culture C—HUVEC human umbilical vein endothelial cell culture transfected with DNA vector GDTT1.8NAS3-HIF1a.

Figure 19:
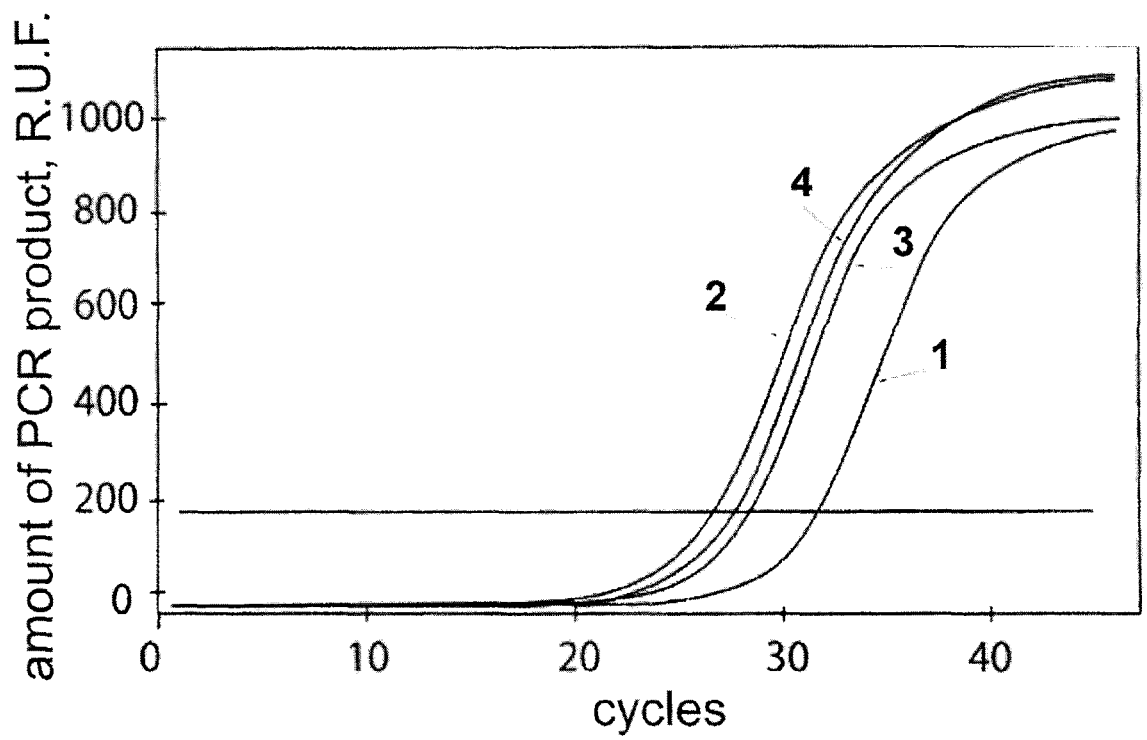

FIG. 19 shows diagrams of human BMP2 mRNA accumulation in human osteosarcoma cells MG-63 before their transfection and 48 hours after transfection of these cells with DNA vector GDTT1.8NAS4-BMP2 carrying the human BMP2 gene in order to assess changes in the mRNA accumulation of therapeutic gene, for example, the BMP2 gene, in human osteosarcoma cells MG-63 before their transfection and 48 hours after transfection of these cells with DNA vector GDTT1.8NAS4-BMP2 carrying the human BMP2 gene, where:
1—cDNA of BMP2 gene after transfection with gene therapy vector GDTT1.8NAS4;
2—cDNA of BMP2 gene after transfection with gene therapy vector GDTT1.8NAS4-BMP2 carrying the human BMP2 gene.
3—cDNA of B2M gene after transfection with gene therapy vector GDTT1.8NAS4;
4—cDNA of B2M gene after transfection with gene therapy vector GDTT1.8NAS4-BMP2 carrying the human BMP2 gene.

Figure 20:
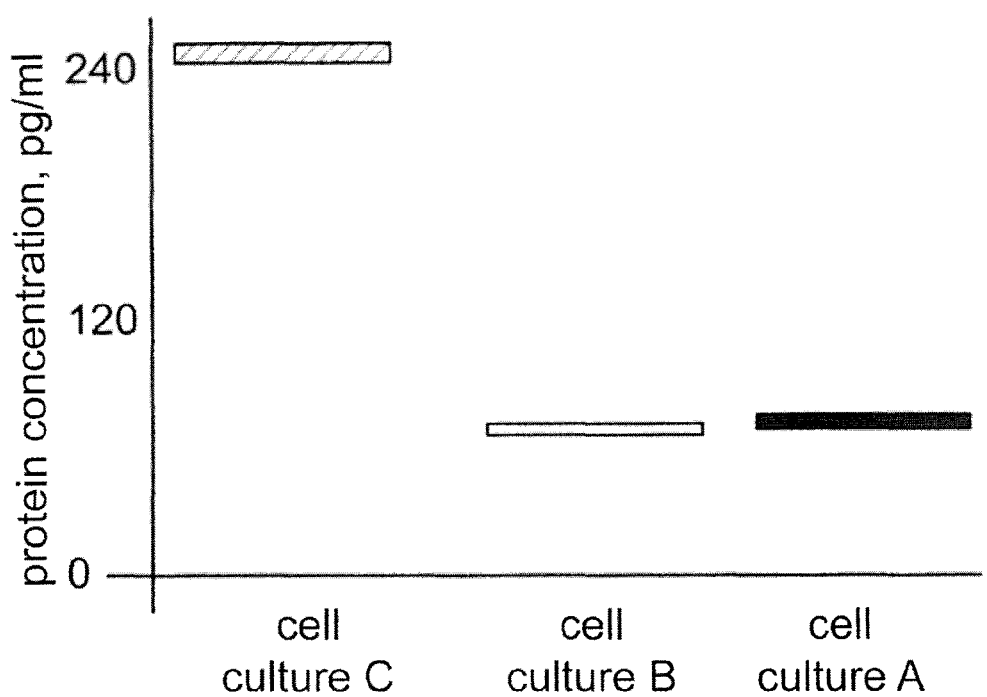

FIG. 20 shows the plot of BMP2 protein concentration in the human osteosarcoma cell lysate MG-63 upon transfection of these cells with the gene therapy DNA vector GDTT1.8NAS4-BMP2 carrying the human BMP2 gene and gene therapy DNA vector GDTT1.8NAS4 not carrying the human BMP2 gene in order to compare the amount of target protein for example BMP2 protein, where: culture A—MG-63 human osteosarcoma cell culture transfected with Lipofectamine 63 solution without plasmid DNA (reference) culture B—MG-63 human osteosarcoma cell culture transfected with DNA vector GDTT1.8NAS4 culture C—MG-63 human osteosarcoma cell culture transfected with DNA vector GDTT1.8NAS4-BMP2.

Figure 21:
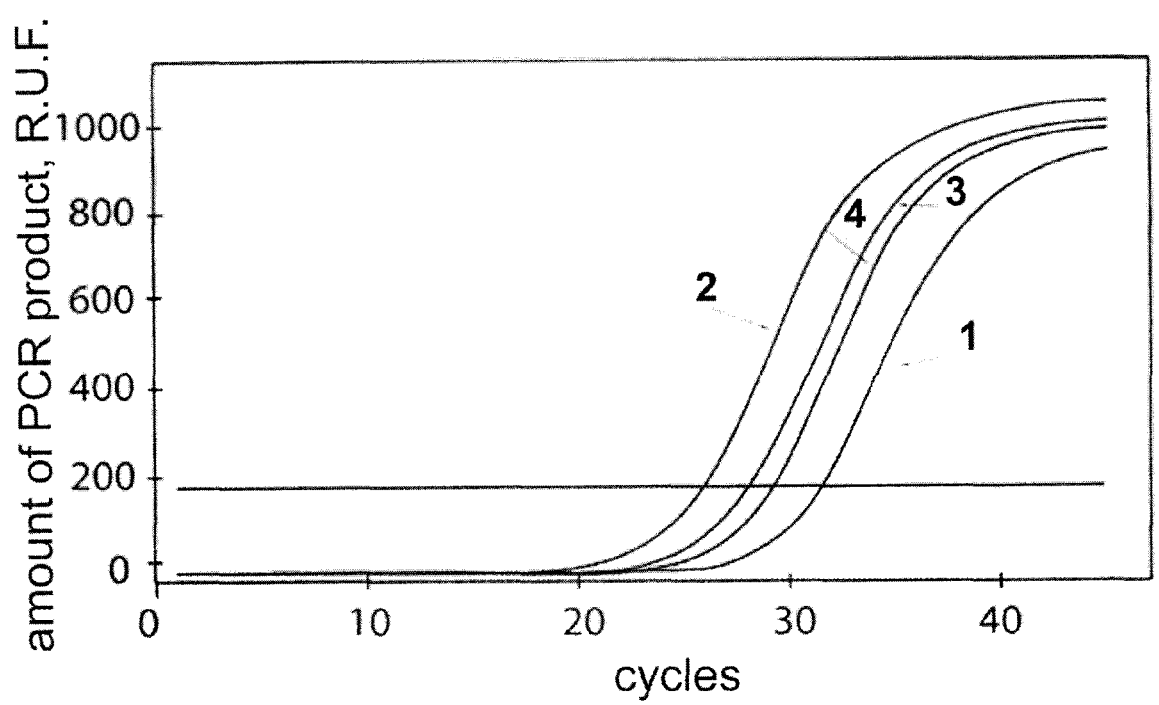
Figure 22:
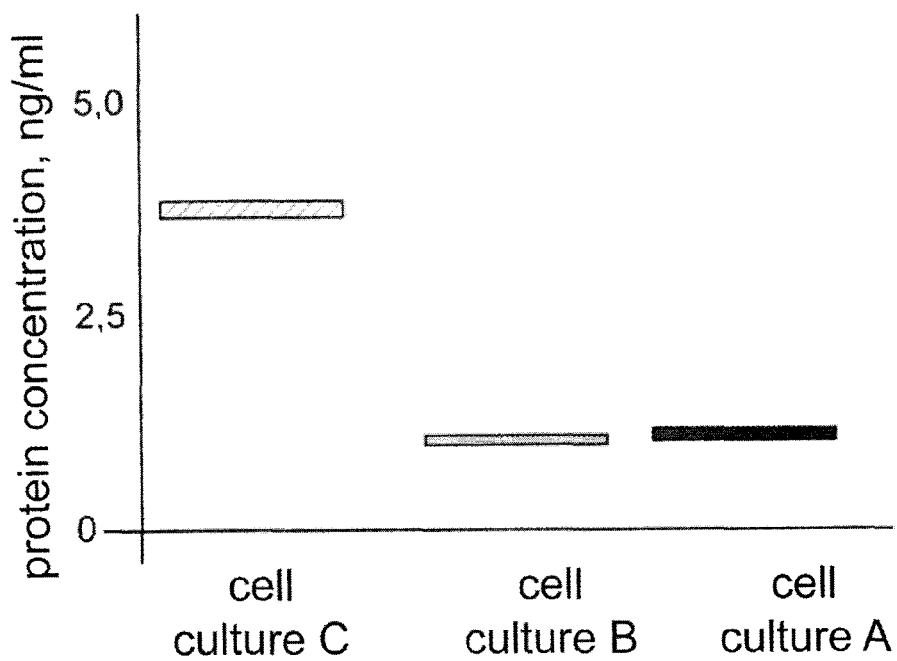

FIG. 21 shows diagrams of human CFTR mRNA accumulation in human tracheal epithelial cell line CFTE29o- before their transfection and 48 hours after transfection of these cells with DNA vector GDTT1.8NAS5-CFTR carrying the human CFTR gene in order to assess changes in the mRNA accumulation of therapeutic gene, for example, the CFTR gene, in human tracheal epithelial cell line CFTE29o- before their transfection and 48 hours after transfection of these cells with DNA vector GDTT1.8NAS5-CFTR carrying the human CFTR gene, where:
1—cDNA of CFTR gene after transfection with gene therapy vector GDTT1.8NAS5;
2—cDNA of CFTR gene after transfection with gene therapy vector GDTT1.8NAS5-CFTR carrying the human CFTR gene;
3—cDNA of B2M gene after transfection with gene therapy vector GDTT1.8NAS5;
4—cDNA of B2Mgene after transfection with gene therapy vector GDTT1.8NAS5-CFTR carrying the human CFTR gene;

FIG. 22 shows the plot of CFTR protein concentration in the human tracheal epithelium lysate CFTE29o- upon transfection of these cells with the gene therapy DNA vector GDTT1.8NAS5-CFTR carrying the human CFTR gene and gene therapy DNA vector GDTT1.8NAS5 not carrying the human CFTR gene in order to compare the amount of target protein for example CFTR protein, where:
culture A—human tracheal epithelial cell culture CFTE29o- transfected with Lipofectamine 3000 without plasmid DNA (reference)
culture B—human tracheal epithelial cell culture CFTE29o- transfected with DNA vector GDTT1.8NAS5
culture C—human tracheal epithelial cell culture CFTE29o- transfected with DNA vector GDTT1.8NAS5-CFTR.

Figure 23:
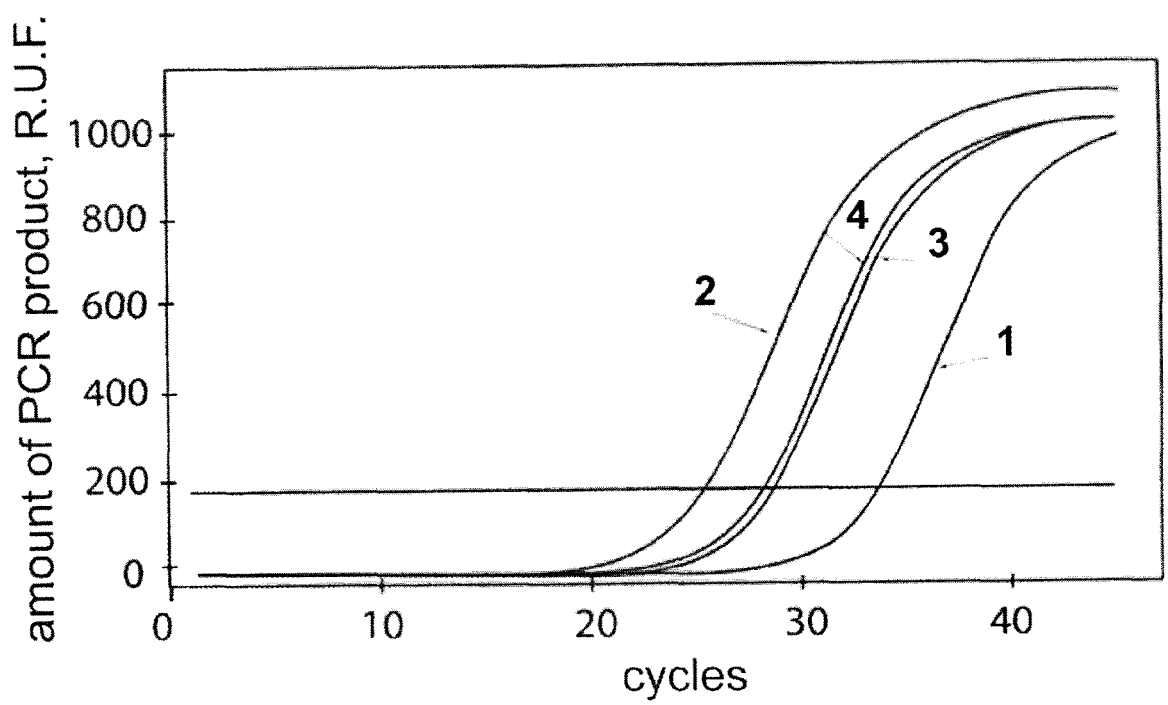

FIG. 23 shows diagrams of human BDNF mRNA accumulation in human neuroblastoma cells SH-SY5Y before their transfection and 48 hours after transfection of these cells with DNA vector GDTT1.8NAS6-BDNF carrying the human BDNF gene in order to assess changes in the mRNA accumulation of therapeutic gene, for example, the BDNF gene, in human neuroblastoma cells SH-SY5Y before their transfection and 48 hours after transfection of these cells with DNA vector GDTT1.8NAS6-BDNF carrying the human BDNF gene, where:
1—cDNA of BDNF gene after transfection with gene therapy vector GDTT1.8NAS6;
2—cDNA of BDNF gene after transfection with gene therapy vector GDTT1.8NAS6-BDNF carrying the human BDNF gene.
3—cDNA of B2M gene after transfection with gene therapy vector GDTT1.8NAS6;
4—cDNA of B2M gene after transfection with gene therapy vector GDTT1.8NAS6-BDNF carrying the human BDNF gene.

Figure 24:
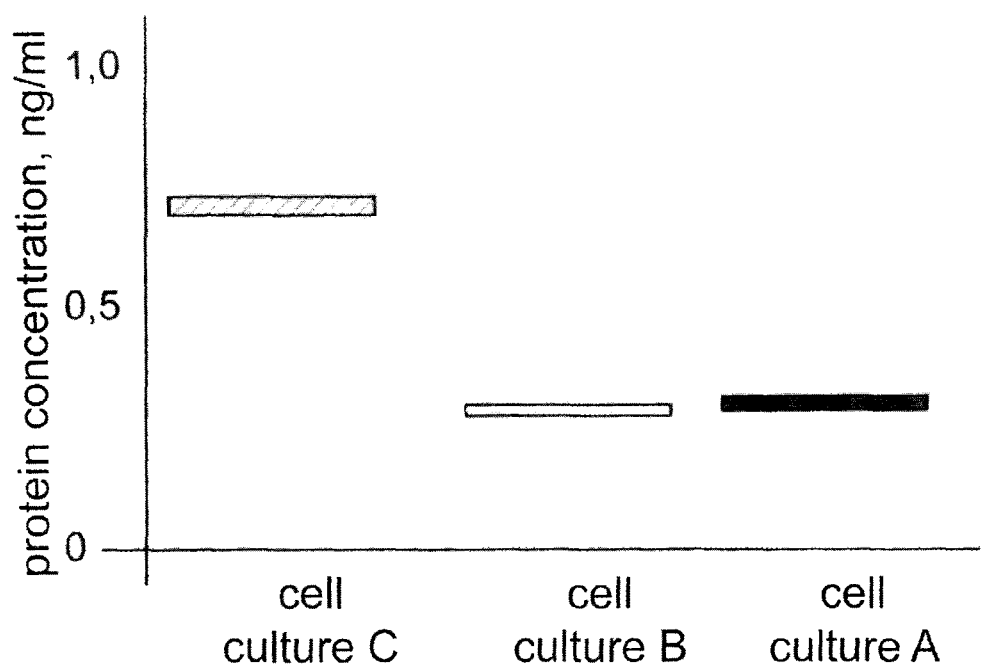

FIG. 24 shows the plot of BDNF protein concentration in the human neuroblastoma cell lysate SH-SY5Y upon transfection of these cells with the gene therapy DNA vector GDTT1.8NAS6-BDNF carrying the human BDNF gene and gene therapy DNA vector GDTT1.8NAS6 not carrying the human BDNF gene in order to compare the amount of target protein for example BDNF protein, where:
culture A—SH-SY5Y human neuroblastoma cell culture transfected with Lipofectamine 3000 without plasmid DNA (reference)

culture B—SH-SY5Y human neuroblastoma cell culture transfected with DNA vector GDTT1.8NAS6
culture C—SH-SY5Y human neuroblastoma cell culture transfected with DNA vector GDTT1.8NAS6-BDNF.

Figure 25:
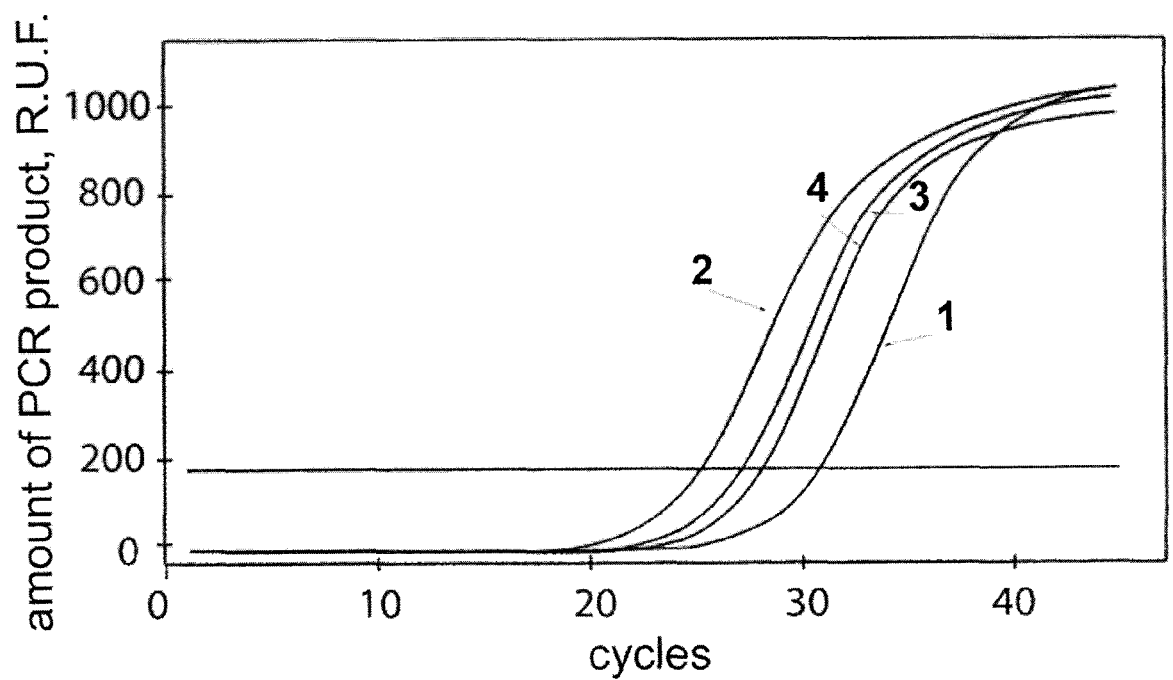

FIG. 25 shows diagrams of human ATGL mRNA accumulation in the primary human kidney epithelial mixed cell culture HREC before their transfection and 48 hours after transfection of these cells with DNA vector GDTT1.8NAS7-ATGL carrying the human ATGL gene in order to assess changes in the mRNA accumulation of therapeutic gene, for example, the ATGL gene, in the primary human kidney epithelial mixed cell culture HREC before their transfection and 48 hours after transfection of these cells with DNA vector GDTT1.8NAS7-ATGL carrying the human ATGL gene, where:
1—cDNA of ATGL gene after transfection with gene therapy vector GDTT1.8NAS7;
2—cDNA of ATGL gene after transfection with gene therapy vector GDTT1.8NAS7-ATGL carrying the human ATGL gene;
3—cDNA of B2M gene after transfection with gene therapy vector GDTT1.8NAS7;
4—cDNA of B2M gene after transfection with gene therapy vector GDTT1.8NAS7-ATGL carrying the human ATGL gene.

Figure 26:
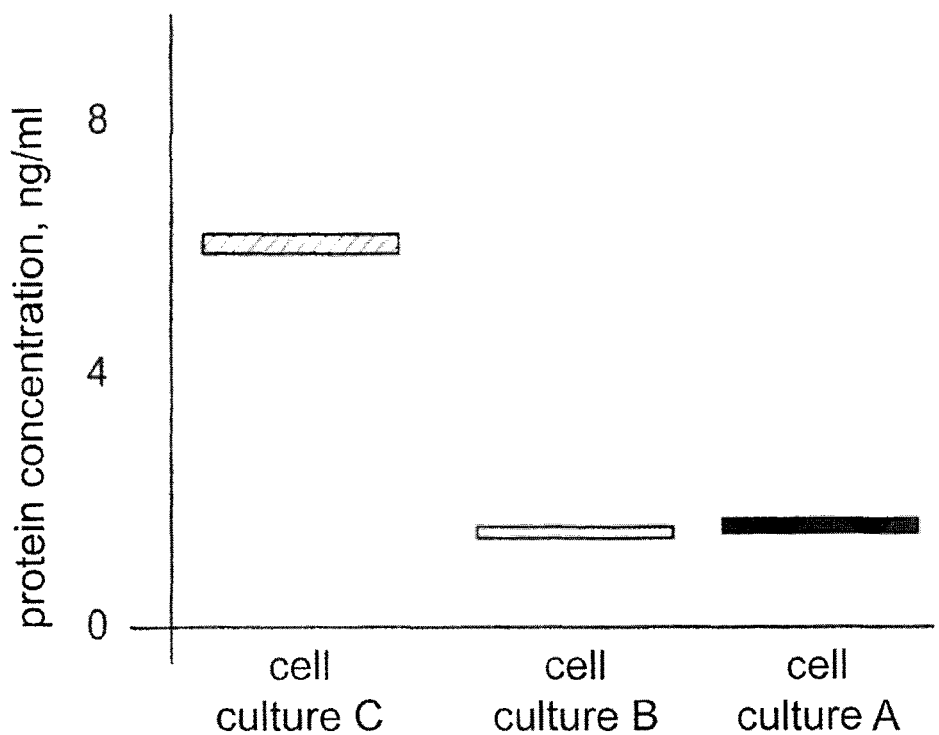

FIG. 26 shows the plot of ATGL protein concentration in the primary human kidney epithelial mixed cell lysate HREC upon transfection of these cells with the gene therapy DNA vector GDTT1.8NAS7-ATGL carrying the human ATGL gene and gene therapy DNA vector GDTT1.8NAS7 not carrying the human ATGL gene in order to compare the amount of target protein for example ATGL protein, where:
culture A—primary human kidney epithelial mixed cell culture HREC transfected with Lipofectamine 3000 without plasmid DNA (reference)
culture B—primary human kidney epithelial mixed cell culture HREC transfected with DNA vector GDTT1.8NAS7
culture C—primary human kidney epithelial mixed cell culture HREC transfected with DNA vector GDTT1.8NAS7-ATGL.

Figure 27:
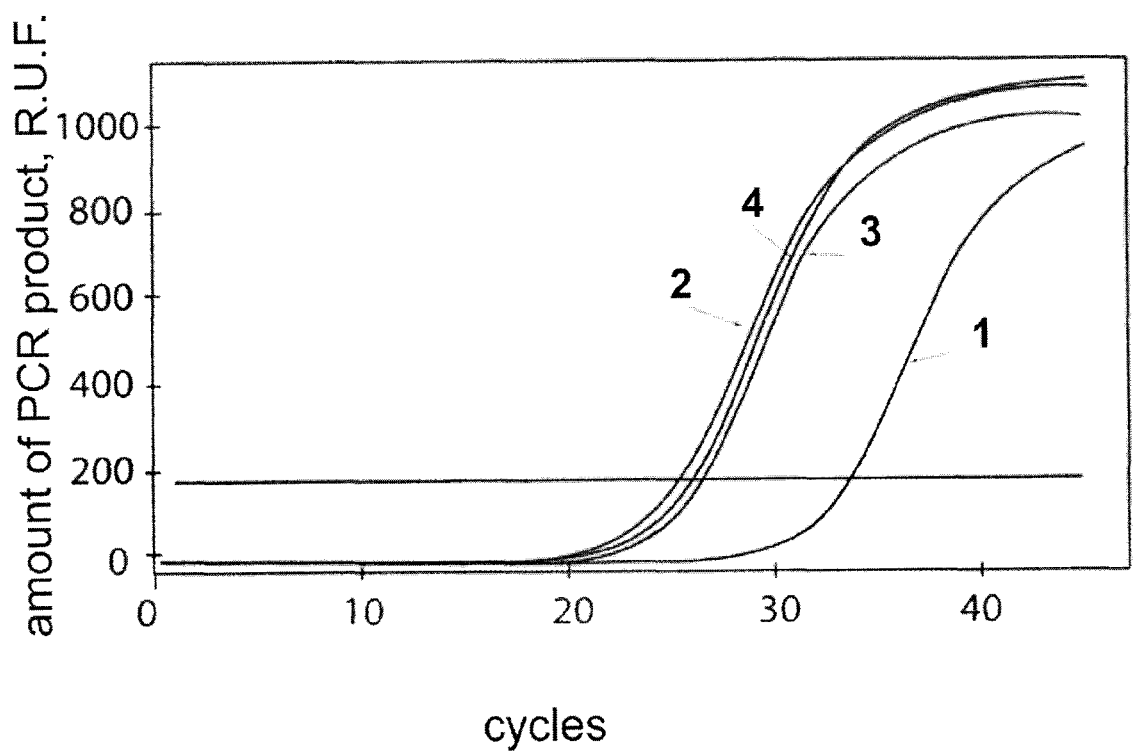

FIG. 27 shows diagrams of human CAS9 mRNA accumulation in the primary human bone marrow cell culture before their transfection and 48 hours after transfection of these cells with DNA vector GDTT1.8NAS8-CAS9 carrying the human CAS9 gene in order to assess changes in the mRNA accumulation of therapeutic gene, for example, the CAS9 gene, in the primary human bone marrow cell culture before their transfection and 48 hours after transfection of these cells with DNA vector GDTT1.8NAS8-CAS9 carrying the human CAS9 gene, where:
1—cDNA of CAS9 gene after transfection with gene therapy vector GDTT1.8NAS8;
2—cDNA of CAS9 gene after transfection with gene therapy vector GDTT1.8NAS8-CAS9 carrying the human CAS9 gene;
3—cDNA of B2M gene after transfection with gene therapy vector GDTT1.8NAS8;
4—cDNA of B2M gene after transfection with gene therapy vector GDTT1.8NAS8-CAS9 carrying the human CAS9 gene.

Figure 28:
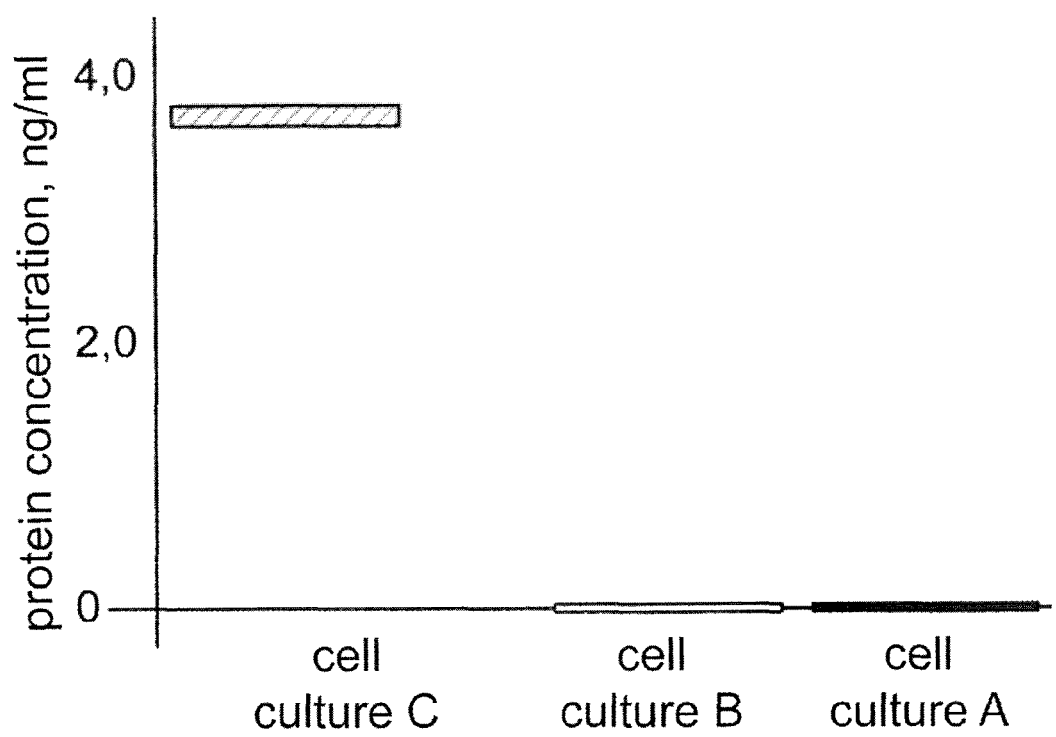

FIG. 28 shows the plot of CAS9 protein concentration in the primary human bone marrow cell lysate upon transfection of these cells with the gene therapy DNA vector GDTT1.8NAS8-CAS9 carrying the human CAS9 gene and gene therapy DNA vector GDTT1.8NAS8 not carrying the human CAS9 gene in order to compare the amount of target protein for example CAS9 protein, where:
culture A—primary human bone marrow cell culture transfected with Lipofectamine 3000 without plasmid DNA (reference)
culture B—primary human bone marrow cell culture transfected with DNA vector GDTT1.8NAS8
culture C—primary human bone marrow cell culture transfected with DNA vector GDTT1.8NAS8-CAS9.

Figure 29:
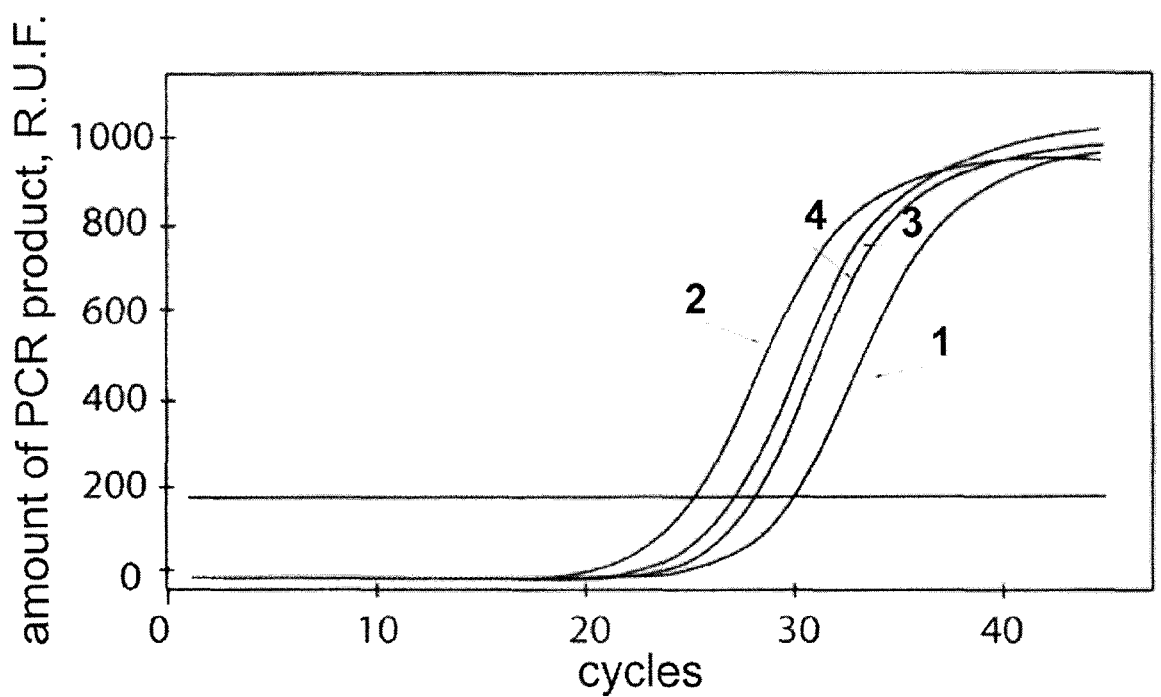

FIG. 29 shows diagrams of human BTK mRNA accumulation in the primary human peripheral blood mononuclear cell culture PBMC before their transfection and 48 hours after transfection of these cells with DNA vector GDTT1.8NAS9-BTK carrying the human BTK gene in order to assess changes in the mRNA accumulation of therapeutic gene, for example, the BTK gene, in the primary human peripheral blood mononuclear cell culture PBMC before their transfection and 48 hours after transfection of these cells with DNA vector GDTT1.8NAS9-VEGF carrying the human BTK gene, where:
1—cDNA of BTK gene after transfection with gene therapy vector GDTT1.8NAS9;
2—cDNA of BTK gene after transfection with gene therapy vector 8NAS9.8NAS9-BTK carrying the human BTK gene;
3—cDNA of B2M gene after transfection with gene therapy vector GDTT1.8NAS9;
4—cDNA of B2M gene after transfection with gene therapy vector GDTT1.8NAS9-BTK carrying the human BTK gene.

Figure 30:
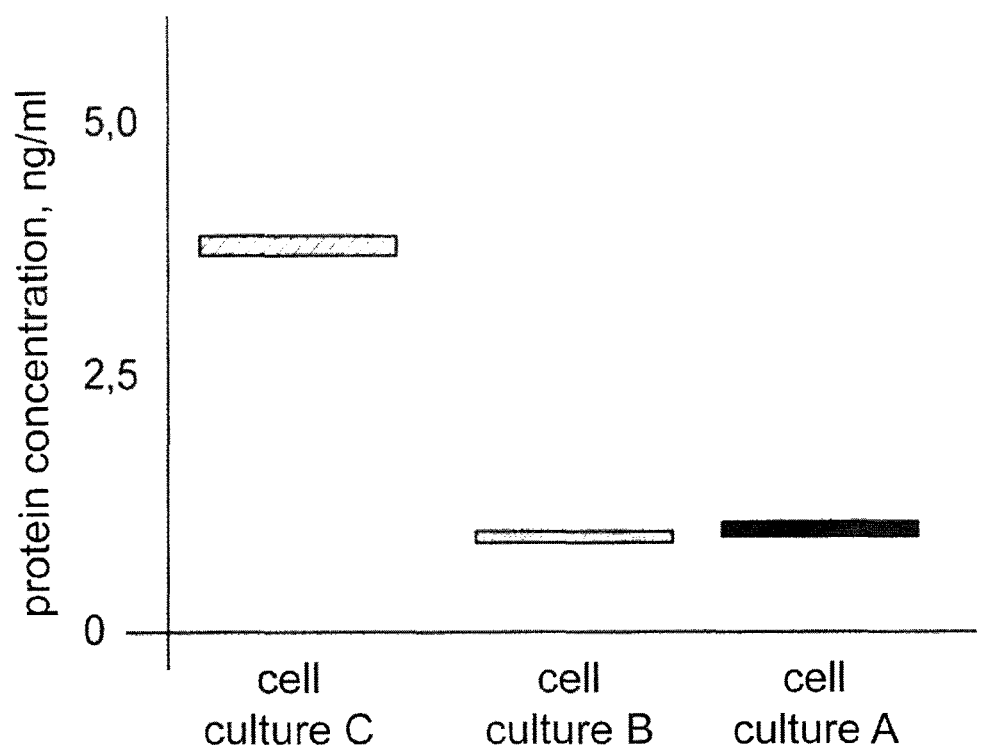

FIG. 30 shows the plot of BTK protein concentration in the primary human peripheral blood mononuclear cell lysate PBMC upon transfection of these cells with the gene therapy DNA vector GDTT1.8NAS9-BTK carrying the human BTK gene and gene therapy DNA vector GDTT1.8NAS9 not carrying the human BTK gene in order to compare the amount of target protein for example BTK protein, where:
culture A—primary human peripheral blood mononuclear cell culture PBMC transfected with Lipofectamine 3000 without plasmid DNA (reference)
culture B—primary human peripheral blood mononuclear cell culture PBMC transfected with DNA vector GDTT1.8NAS9
culture C—primary human peripheral blood mononuclear cell culture PBMC transfected with DNA vector GDTT1.8NAS9-BTK.

Figure 31:
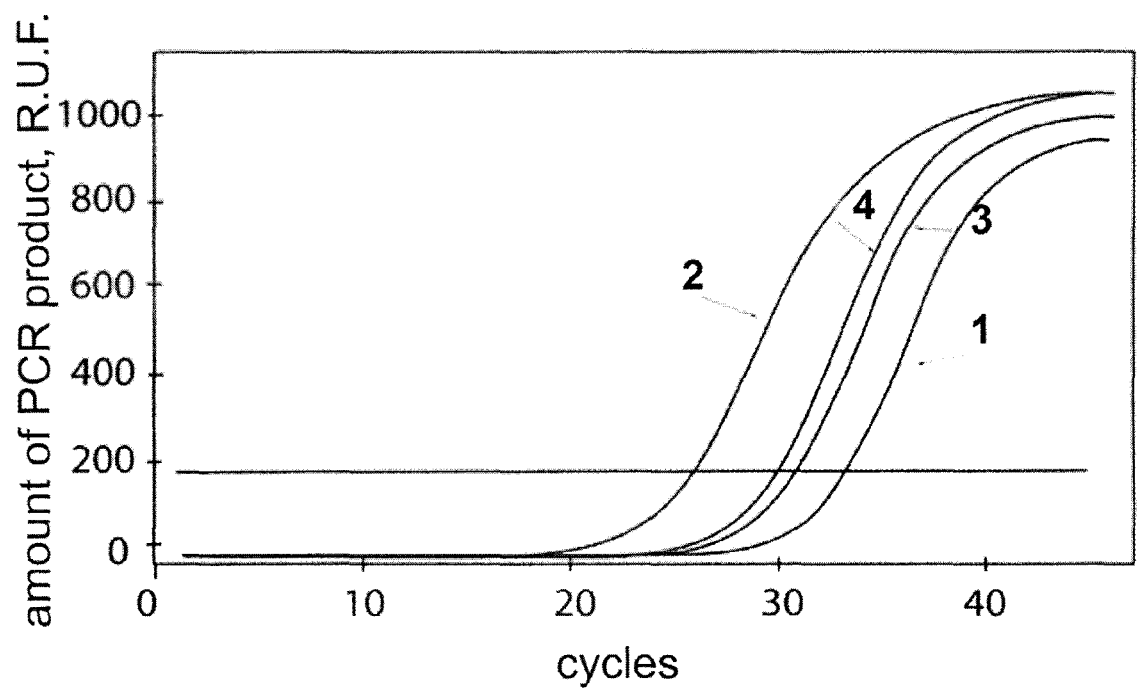

FIG. 31 shows diagrams of human GBA mRNA accumulation in human peripheral blood macrophages SC before their transfection and 48 hours after transfection of these cells with DNA vector GDTT1.8NAS10-GBA carrying the human GBA gene in order to assess changes in the mRNA accumulation of therapeutic gene, for example, the GBA gene, in human peripheral blood macrophages SC before their transfection and 48 hours after transfection of these cells with DNA vector GDTT1.8NAS10-GBA carrying the human GBA gene, where:
1—cDNA of GBA gene after transfection with gene therapy vector GDTT1.8NAS10;
2—cDNA of GBA gene after transfection with gene therapy vector GDTT1.8NAS10-GBA carrying the human GBA gene;
3—cDNA of B2M gene after transfection with gene therapy vector GDTT1.8NAS10;
4—cDNA of B2M gene after transfection with gene therapy vector GDTT1.8NAS10-GBA carrying the human GBA gene.

Figure 32:
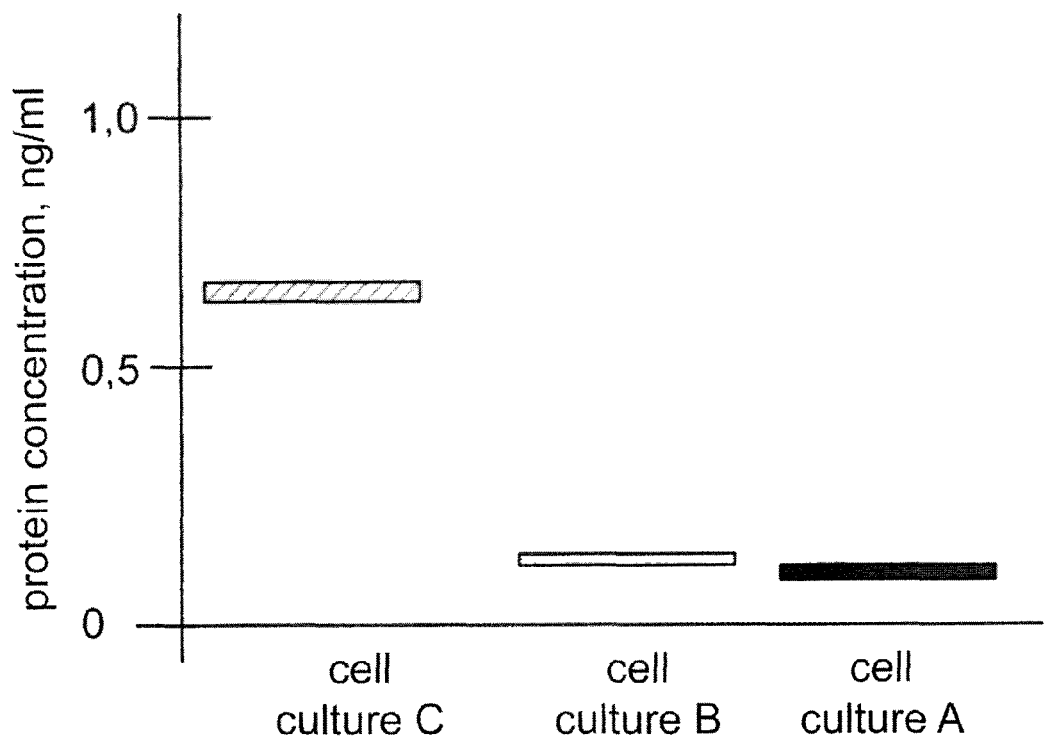

FIG. 32 shows the plot of GBA protein concentration in the human peripheral blood macrophages lysate SC upon transfection of these cells with the gene therapy DNA vector GDTT1.8NAS10-GBA carrying the human GBA gene and gene therapy DNA vector GDTT1.8NAS10 not carrying the human GBA gene in order to compare the amount of target protein for example GBA protein, where:

culture A—human peripheral blood macrophage cell culture SC transfected with Lipofectamine 3000 without plasmid DNA (reference)

culture B—human peripheral blood macrophage cell culture SC transfected with DNA vector GDTT1.8NAS10 culture C—human peripheral blood macrophage cell culture SC transfected with DNA vector GDTT1.8NAS10-GBA.

Figure 33:
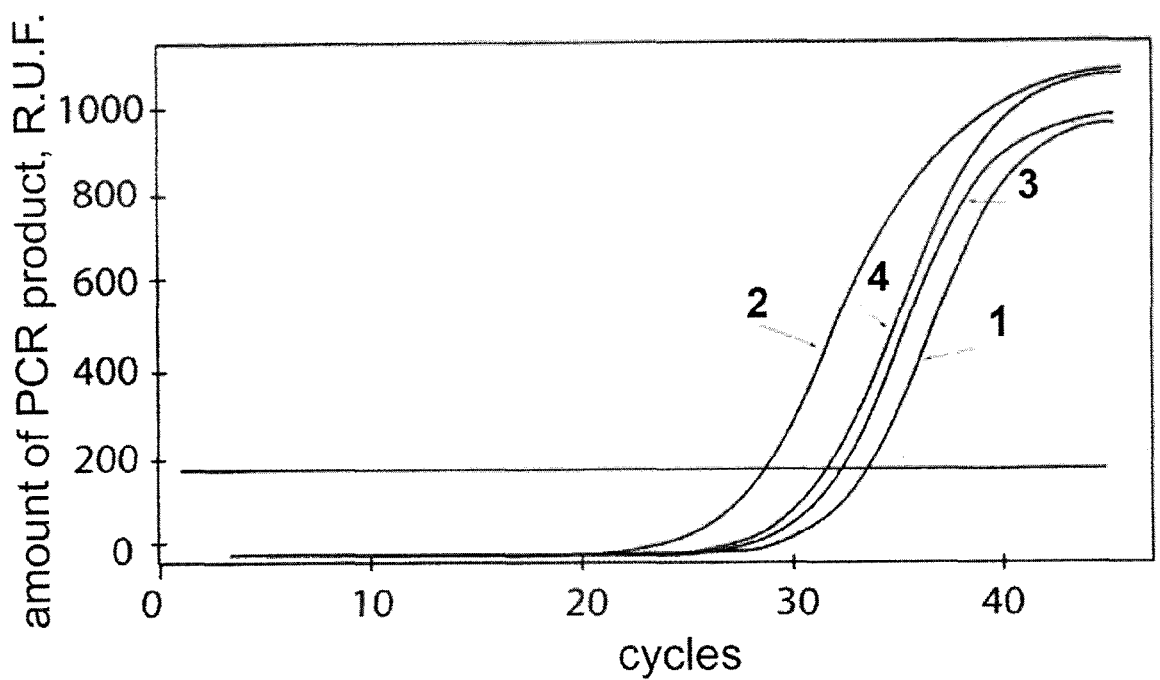

FIG. 33 shows diagrams of human PDX1 mRNA accumulation in pancreatic adenocarcinoma cells Panc 10.05 before their transfection and 48 hours after transfection of these cells with DNA vector GDTT1.8NAS11-PDX1 carrying the human PDX1 gene in order to assess changes in the mRNA accumulation of therapeutic gene, for example, the PDX1 gene, in pancreatic adenocarcinoma cells Panc 10.05 before their transfection and 48 hours after transfection of these cells with DNA vector GDTT1.8NAS11-PDX1 carrying the human PDX1 gene, where:

1—cDNA of PDX1 gene after transfection with gene therapy vector GDTT1.8NAS11;

2—cDNA of PDX1 gene after transfection with gene therapy vector GDTT1.8NAS11-PDX1 carrying the human PDX1 gene;

3—cDNA of B2M gene after transfection with gene therapy vector GDTT1.8NAS11;

4—cDNA of B2M gene after transfection with gene therapy vector GDTT1.8NAS11-PDX1 carrying the human PDX1 gene.

Figure 34:
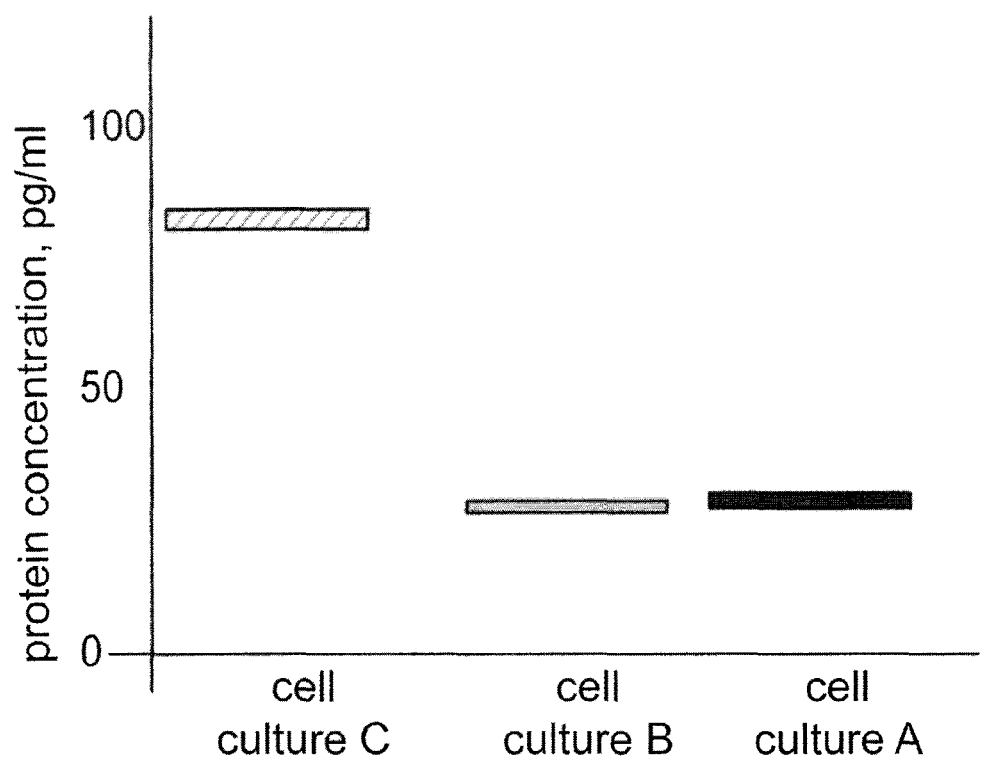

FIG. 34 shows the plot of PDX1 protein concentration in the pancreatic adenocarcinoma cells lysate Panc 10.05 upon transfection of these cells with the gene therapy DNA vector GDTT1.8NAS11-PDX1 carrying the human PDX1 gene and gene therapy DNA vector GDTT1.8NAS11 not carrying the human PDX1 gene in order to compare the amount of target protein for example PDX1 protein, where:

culture A—Panc 10.05 pancreatic adenocarcinoma cell culture transfected with Lipofectamine 63 solution without plasmid DNA (reference)

culture B—Panc 10.05 pancreatic adenocarcinoma cell culture transfected with DNA vector GDTT1.8NAS11 culture C—Panc 10.05 pancreatic adenocarcinoma cell culture transfected with DNA vector GDTT1.8NAS11-PDX1

Figure 35:
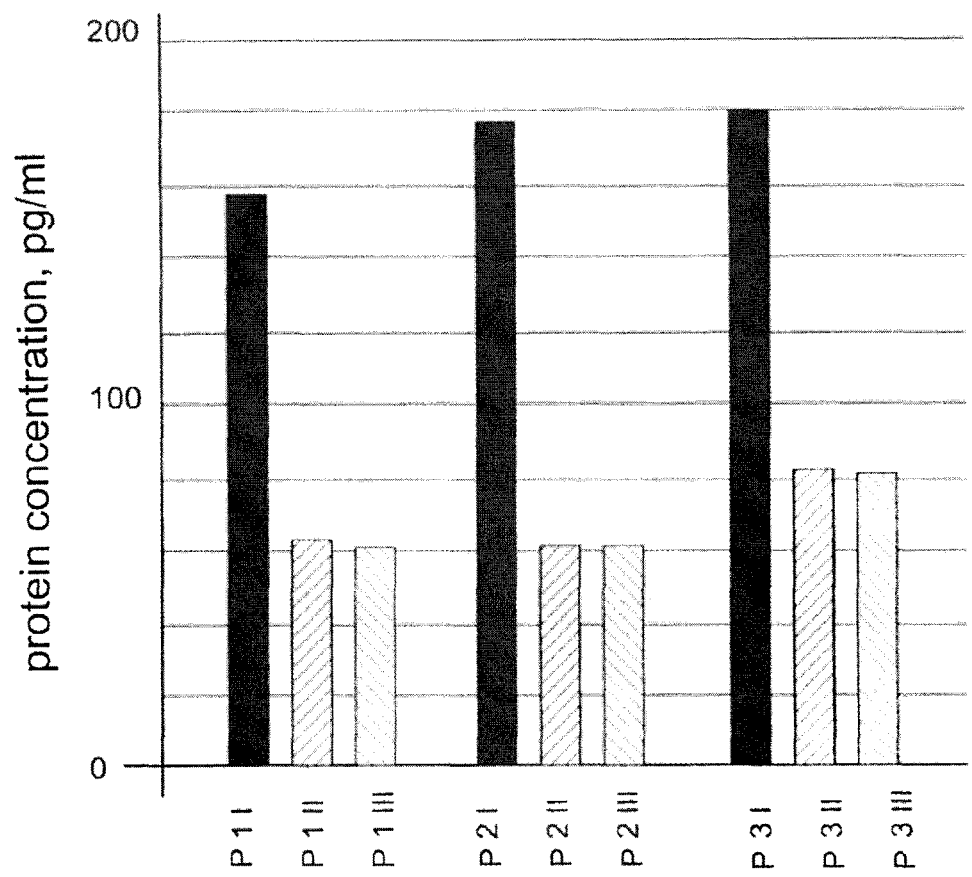

FIG. 35 shows the plot of VEGF protein concentration in gastrocnemius muscle biopsy specimens of three patients after the injection in the gastrocnemius muscle of these patients of gene therapy DNA vector GDTT1.8NAS1-VEGF carrying the human VEGF gene, and the concurrent injection of gene therapy DNA vector GDTT1.8NAS1 not carrying the human VEGF gene in order to compare the amount of the therapeutic protein, for example, VEGF protein, where:

P1I—patient P1 gastrocnemius muscle biopsy in the region of injection of gene therapy DNA vector GDTT1.8NAS1-VEGF P1II—patient P1 gastrocnemius muscle biopsy in the region of injection of gene therapy DNA vector GDTT1.8NAS1 (placebo)

P1III—patient P1 gastrocnemius muscle biopsy from intact site

P2I—patient P2 gastrocnemius muscle biopsy in the region of injection of gene therapy DNA vector GDTT1.8NAS1-VEGF P2II—patient P2 gastrocnemius muscle biopsy in the region of injection of gene therapy DNA vector GDTT1.8NAS1 (placebo)

P2III—patient P2 gastrocnemius muscle biopsy from intact site

P3I—patient P3 gastrocnemius muscle biopsy in the region of injection of gene therapy DNA vector GDTT1.8NAS1-VEGF P3II—patient P3 gastrocnemius muscle biopsy in the region of injection of gene therapy DNA vector GDTT1.8NAS1 (placebo)

P3III—patient P3 gastrocnemius muscle biopsy from intact site.

Figure 36:
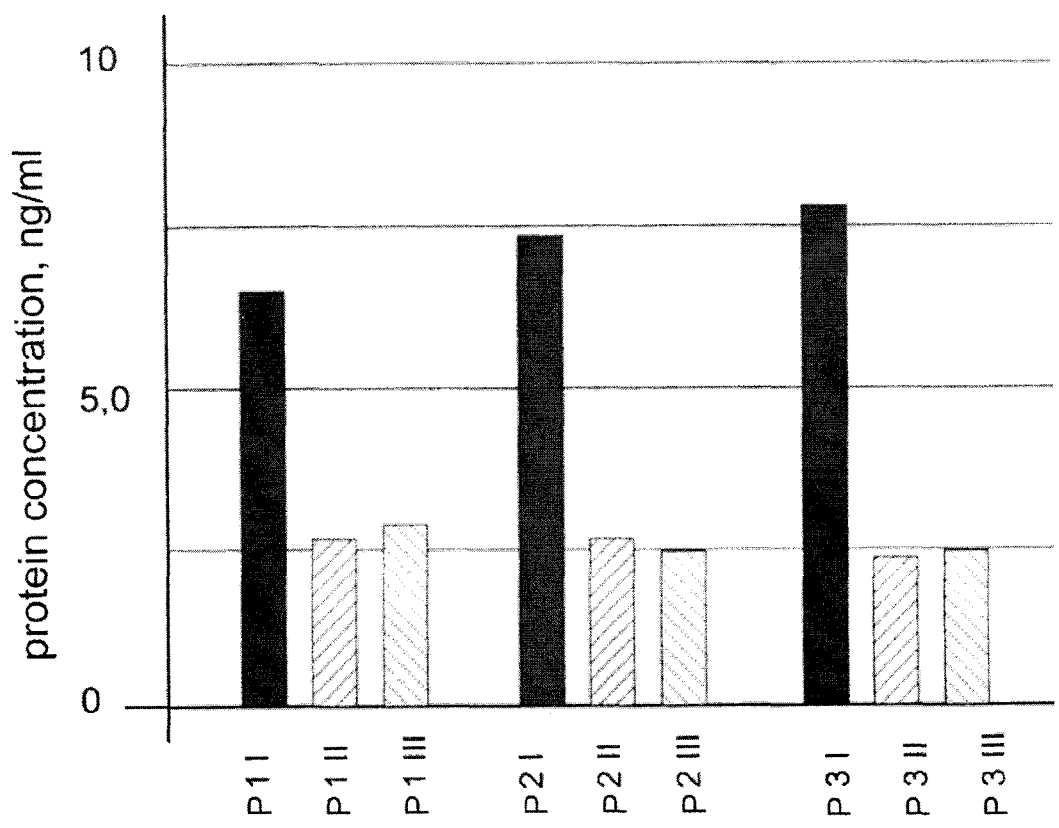

FIG. 36 shows the plot of CAT protein concentration in skin biopsy specimens of three patients after the injection in the skin of these patients of gene therapy DNA vector GDTT1.8NAS2-CAT carrying the human CAT gene, and the parallel injection of gene therapy DNA vector GDTT1.8NAS2 not carrying the human CAT gene in order to compare the amount of the therapeutic protein, for example, CAT protein, where:

P1I is patient P1 skin biopsy in the region of injection of gene therapy DNA vector GDTT1.8NAS2-CAT P1II is patient P1 skin biopsy in the region of injection of gene therapy DNA vector GDTT1.8NAS2 (placebo)

P1III—patient P1 skin biopsy from intact site

P2I is patient P2 skin biopsy in the region of injection of gene therapy DNA vector GDTT1.8NAS2-CAT P2II is patient P2 skin biopsy in the region of injection of gene therapy DNA vector GDTT1.8NAS2 (placebo)

P2III—patient P2 skin biopsy from intact site

P3I is patient P3 skin biopsy in the region of injection of gene therapy DNA vector GDTT1.8NAS2-CAT P3II is patient P3 skin biopsy in the region of injection of gene therapy DNA vector GDTT1.8NAS2 (placebo)

P3III is patient P3 skin biopsy from intact site

Figure 37:
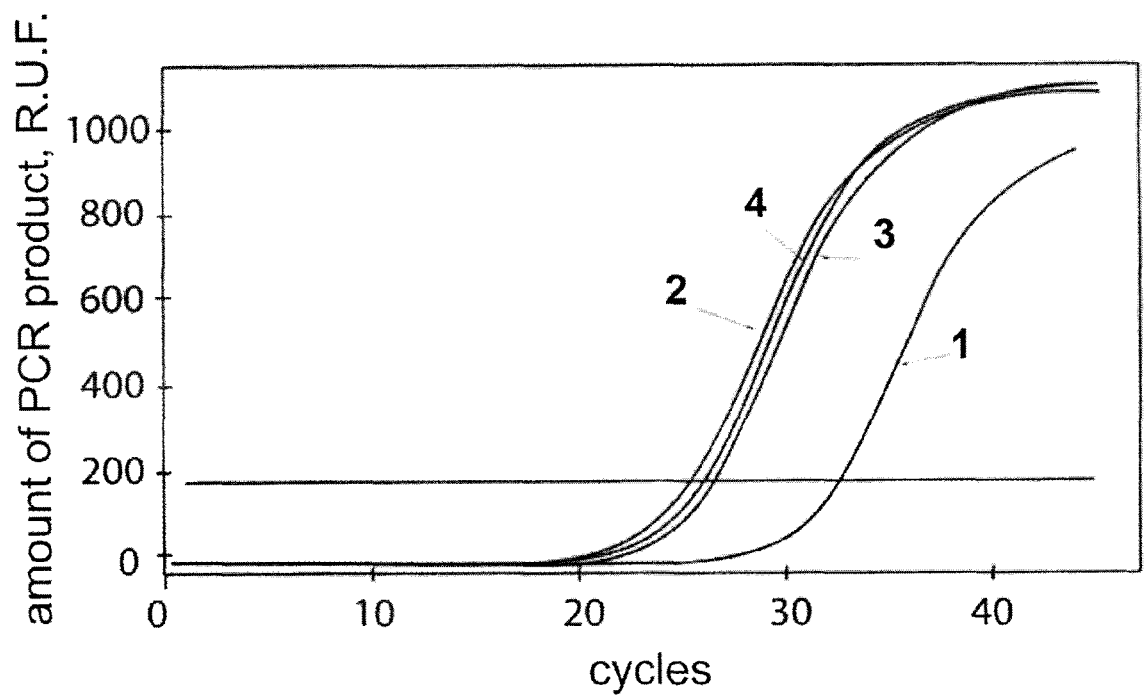

FIG. 37 shows diagrams of human ATGL mRNA accumulation in the bovine kidney cells MDBK before their transfection and 48 hours after transfection of these cells with DNA vector GDTT1.8NAS7-ATGL carrying the human ATGL gene in order to assess changes in the mRNA accumulation of therapeutic gene, for example, the ATGL gene, in the bovine kidney cells MDBK before their transfection and 48 hours after transfection of these cells with DNA vector GDTT1.8NAS1-ATGL carrying the human ATGL gene, where:

1—cDNA of ATGL gene after transfection with gene therapy vector GDTT1.8NAS7;

2—cDNA of ATGL gene after transfection with gene therapy vector GDTT1.8NAS7-ATGL carrying the human ATGL gene;

3—cDNA of bovine ACT gene after transfection with gene therapy vector GDTT1.8NAS7;

4—cDNA of bovine ACT gene after transfection with gene therapy vector 8NAS7.8NAS7-ATGL carrying the human ATGL gene.

Figure 38:
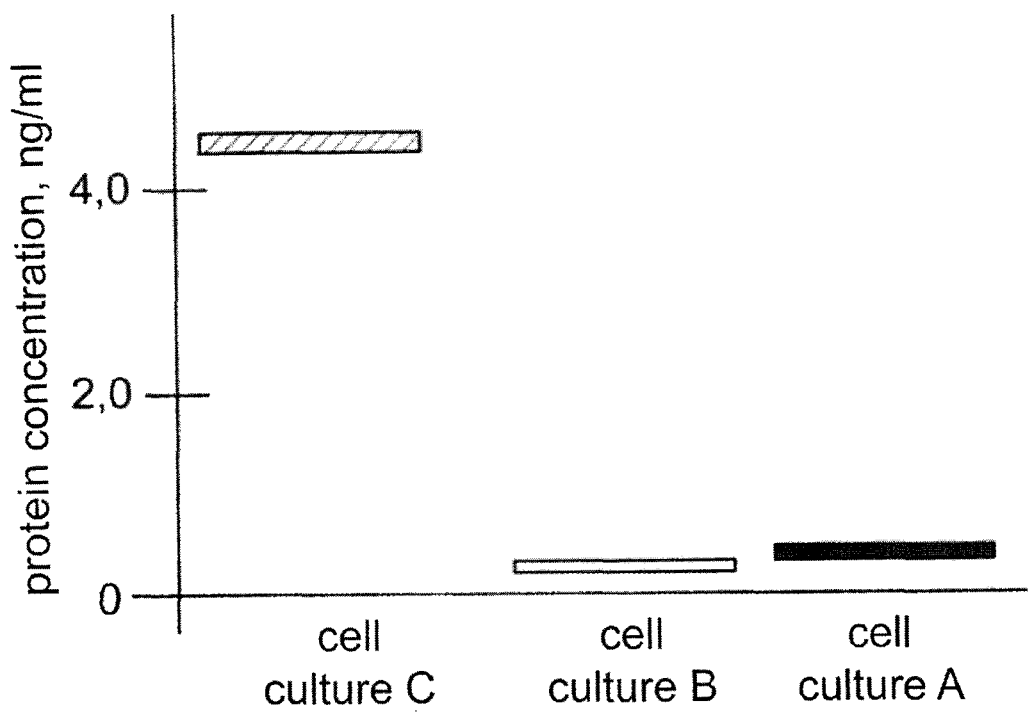

FIG. 38 shows the plot of ATGL protein concentration in the bovine kidney cell lysate MDBK upon transfection of these cells with the gene therapy DNA vector GDTT1.8NAS7-ATGL carrying the human ATGL gene and gene therapy DNA vector GDTT1.8NAS7 not carrying the human ATGL gene in order to compare the amount of target protein for example ATGL protein, where:

culture A—bovine kidney cell culture MDBK transfected with Lipofectamine 3000 without plasmid DNA (reference)

culture B—MDBK bovine kidney cell culture transfected with DNA vector GDTT1.8NAS7 culture C—MDBK bovine kidney cell culture transfected with DNA vector GDTT1.8NAS7-ATGL

EMBODIMENT OF THE INVENTION

In order to confirm the efficiency of the constructed gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11 the following was assessed:
A) change in mRNA accumulation of therapeutic/therapy genes in human and animal cell lysate after transfection of different human and animal cell lines with gene therapy DNA vectors;
B) change in the quantitative level of therapeutic/therapy proteins in the human and animal cell lysate after transfection of different human and animal cell lines with gene therapy DNA vectors;
C) change in the quantitative level of therapeutic/therapy proteins in the supernatant of human tissue biopsies after the injection of gene therapy DNA vectors into these tissues;
In order to confirm the practicability of use of the constructed gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11, the following was performed:
D) transfection of different human and animal cell lines with gene therapy DNA vectors;
E) injection of gene therapy DNA vectors into different human tissues;
For the validation of the tissue specificity of the constructed gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11, the following was performed:
F) transfection of several human and animal cell lines with several gene therapy DNA vectors; To confirm the producibility and constructability on an industrial scale of gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11, the following was performed:
H) fermentation on an industrial scale of *Escherichia coli* strain JM-110-NAS-GDTT1.8NAS1 or *Escherichia coli* strain JM-110-NAS-GDTT1.8NAS2 or *Escherichia coli* strain JM-110-NAS-GDTT1.8NAS3 or *Escherichia coli* strain JM-110-NAS-GDTT1.8NAS4 or *Escherichia coli* strain JM-110-NAS-GDTT1.8NAS5 or *Escherichia coli* strain JM-110-NAS-GDTT1.8NAS6 or *Escherichia coli* strain JM-110-NAS-GDTT1.8NAS7 or *Escherichia coli* strain JM-110-NAS-GDTT1.8NAS8 or *Escherichia coli* strain JM-110-NAS-GDTT1.8NAS9 or *Escherichia coli* strain JM-110-NAS-GDTT1.8NAS10 or *Escherichia coli* strain JM-110-NAS-GDTT1.8NAS11 each containing gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11.

The essence of the invention is explained in the following examples.

Example 1

Production of gene therapy DNA vector GDTT1.8NAS1 containing the promoter and regulatory region of the human myoglobin gene in order to increase the expression of therapeutic genes in muscle cells.

Gene therapy DNA vector GDTT1.8NAS1 was constructed by consolidating six fragments of DNA derived from different sources:
(a) the origin of replication was produced by PCR amplification of a region of commercially available pUC19 plasmid with UCori-Bam and UCori-Nco oligonucleotides (List of Sequences, (1)-(2)),
(b) the hGH-TA transcription terminator was produced by PCR amplification of a region of human genomic DNA using hGH-F and hGH-R oligonucleotides (List of Sequences, (3) and (4)),
(c) the regulatory region RNA-OUT of transposon Tn10 was obtained from RO-F, RO-R, RO-1, RO-2, and RO-3 oligonucleotides (List of Sequences, (5H9)),
(d) the kanamycin resistance gene was produced by PCR amplification of a region of commercially available pET-28 plasmid using Kan-F and Kan-R oligonucleotides (List of Sequences, (10) and (11)),
(e) the polylinker was produced by phosphorylation and annealing of four synthetic oligonucleotides MCS1, MCS2, MCS3, and MCS4 (List of Sequences, (12)-(15)),
(f) the promoter and regulatory region of human myoglobin was produced by PCR amplification of a region of human genomic DNA using oligonucleotides Myo-F and Myo-R (List of Sequences, (16)-(17)).

PCR amplification was performed using the commercially available kit Phusion® High-Fidelity DNA Polymerase (New England Biolabs) as per the manufacturer's instructions. The fragments (b), (c), and (d) had overlapping regions allowing for their consolidation with subsequent PCR amplification. Fragments (b), (c), and (d) were joined using hGH-F and Kan-R oligonucleotides (List of Sequences, (3) and (11)). Afterwards, the obtained DNA fragments were consolidated by restriction with subsequent ligation by BamHI and NcoI sites. This resulted in a plasmid still devoid of the polylinker. To introduce it, the plasmid was cleaved by restriction endonucleases in BamHI and EcoRI sites with further ligation to the fragment (f). This resulted in a 2408 bp intermediate vector carrying a kanamycin resistance gene, but still without promoter and regulatory region of human myoglobin. The vector obtained was cleaved by restriction endonucleases in XhoI and BamHI sites with further ligation to the fragment (f). This resulted in a 2753 bp vector carrying a kanamycin resistance gene and promoter and regulatory region of human myoglobin. Then the kanamycin resistance gene was cleaved by SpeI restriction sites, and the remaining fragment was ligated to itself. Thus, a 1736 bp recombinant gene therapy DNA vector GDTT1.8NAS1 enabling antibiotic-free selection and tissue-specific expression of therapeutic genes cloned into it mainly in muscle tissue cells (SEQ ID No. 1).

Example 2

Production of gene therapy DNA vector GDTT1.8NAS2 containing the promoter and regulatory region of the human elastase gene in order to increase the expression of therapeutic genes in skin cells.

The gene therapy DNA vector GDTT1.8NAS2 was constructed as described in Example 1, except that fragment (e), which is a promoter and regulatory region of human elastase gene, was obtained by PCR amplification of a region of human genomic DNA using Els-F and Els-R oligonucleotides (List of Sequences, (18)-(19)).

Then a 2408 bp intermediate vector carrying a kanamycin resistance gene, which still does not contain a promoter and regulatory region of the human elastase gene, was cleaved by restriction endonucleases in XhoI and BamHI sites with further ligation to the fragment (f). This resulted in a 2671 bp vector carrying a kanamycin resistance gene and promoter and regulatory region of human elastase gene. Then the kanamycin resistance gene was cleaved by SpeI restriction sites, and the remaining fragment was ligated to itself. Thus, a 1654 bp recombinant gene therapy DNA vector GDTT1.8NAS2 enabling antibiotic-free selection and tissue-specific expression of therapeutic genes cloned into it mainly in skin cells (SEQ ID No. 2).

Example 3

Production of gene therapy DNA vector GDTT1.8NAS3 containing the promoter and regulatory region of the human intercellular adhesion molecule gene 2 in order to increase the expression of therapeutic genes in the vascular endothelial cells.

The gene therapy DNA vector GDTT1.8NAS3 was constructed as described in Example 1, except that fragment (e), which is a promoter and regulatory region of the human intercellular adhesion molecule gene 2, was obtained by PCR amplification of a region of human genomic DNA using ICAM-F and ICAM-R oligonucleotides (List of Sequences, (20)-(21)).

Then a 2408 bp intermediate vector carrying a kanamycin resistance gene, which still does not contain a promoter and regulatory region of the human intercellular adhesion molecule gene 2, was cleaved by restriction endonucleases in XhoI and BamHI sites with further ligation to the fragment (f). This resulted in a 2800 bp vector carrying a kanamycin resistance gene and promoter and regulatory region of the human intercellular adhesion molecule gene 2. Then the kanamycin resistance gene was cleaved by SpeI restriction sites, and the remaining fragment was ligated to itself. Thus, a 1783 bp recombinant gene therapy DNA vector GDTT1.8NAS3 enabling antibiotic-free selection and tissue-specific expression of therapeutic genes cloned into it mainly in the vascular endothelial cells (SEQ ID No. 3).

Example 4

Production of gene therapy DNA vector GDTT1.8NAS4 containing the promoter and regulatory region of the human osteocalcin gene 2 in order to increase the expression of therapeutic genes in osteoblasts and odontoblasts.

The gene therapy DNA vector GDTT1.8NAS4 was constructed as described in Example 1, except that fragment (e), which is a promoter and regulatory region of human osteocalcin gene 2, was obtained by PCR amplification of a region of human genomic DNA using OS2-F and OS2-R oligonucleotides (List of Sequences, (22)-(23)).

Then a 2408 bp intermediate vector carrying a kanamycin resistance gene, which still does not contain a promoter and regulatory region of the human osteocalcin gene 2, was cleaved by restriction endonucleases in XhoI and BamHI sites with further ligation to the fragment (f). This resulted in a 2970 bp vector carrying a kanamycin resistance gene and promoter and regulatory region of human osteocalcin gene 2. Then the kanamycin resistance gene was cleaved by SpeI restriction sites, and the remaining fragment was ligated to itself. Thus, a 1953 bp recombinant gene therapy DNA vector GDTT1.8NAS4 enabling antibiotic-free selection and tissue-specific expression of therapeutic genes cloned into it mainly in osteoblasts and odontoblasts (SEQ ID No. 4).

Example 5

Production of gene therapy DNA vector GDTT1.8NAS5 containing the promoter and regulatory region of the surfactant protein B gene in order to increase the expression of therapeutic genes in bronchi and alveoli epithelial cells.

The gene therapy DNA vector GDTT1.8NAS5 was constructed as described in Example 1, except that fragment (e), which is a promoter and regulatory region of surfactant protein B gene, was obtained by PCR amplification of a region of human genomic DNA using Spb-F and Spb-R oligonucleotides (List of Sequences, (24)-(25)).

Then a 2408 bp intermediate vector carrying a kanamycin resistance gene, which still does not contain a promoter and regulatory region of the surfactant protein B gene, was cleaved by restriction endonucleases in XhoI and BamHI sites with further ligation to the fragment (f). This resulted in a 3036 bp vector carrying a kanamycin resistance gene and promoter and regulatory region of surfactant protein B gene. Then the kanamycin resistance gene was cleaved by SpeI restriction sites, and the remaining fragment was ligated to itself. Thus, a 2019 bp recombinant gene therapy DNA vector GDTT1.8NAS5 enabling antibiotic-free selection and tissue-specific expression of therapeutic genes cloned into it mainly in bronchi and alveoli epithelial cells (SEQ ID No. 5).

Example 6

Production of gene therapy DNA vector GDTT1.8NAS6 containing the promoter and regulatory region of the human synapsin I gene in order to increase the expression of therapeutic genes in neurons.

The gene therapy DNA vector GDTT1.8NAS6 was constructed as described in Example 1, except that fragment (e), which is a promoter and regulatory region of human synapsin I gene, was obtained by PCR amplification of a region of human genomic DNA using Syn-F and Syn-R oligonucleotides (List of Sequences, (26)-(27)).

Then a 2408 bp intermediate vector carrying a kanamycin resistance gene, which still does not contain a promoter and regulatory region of the human synapsin I gene, was cleaved by restriction endonucleases in XhoI and BamHI sites with further ligation to the fragment (f). This resulted in a 2957 bp vector carrying a kanamycin resistance gene and promoter and regulatory region of human synapsin I gene. Then the kanamycin resistance gene was cleaved by SpeI restriction sites, and the remaining fragment was ligated to itself. Thus, a 1940 bp recombinant gene therapy DNA vector GDTT1.8NAS6 enabling antibiotic-free selection and tissue-specific expression of therapeutic genes cloned into it mainly in neurons (SEQ ID No. 6).

Example 7

Production of gene therapy DNA vector GDTT1.8NAS7 containing the promoter and regulatory region of the human nephrin gene in order to increase the expression of therapeutic genes in renal podocytes.

The gene therapy DNA vector GDTT1.8NAS7 was constructed as described in Example 1, except that fragment (e), which is a promoter and regulatory region of human nephrin gene, was obtained by PCR amplification of a region of human genomic DNA using NPHS-F and NPHS-R oligonucleotides (List of Sequences, (28)-(29)).

Then a 2408 bp intermediate vector carrying a kanamycin resistance gene, which still does not contain a promoter and regulatory region of the human nephrin gene, was cleaved by restriction endonucleases in XhoI and BamHI sites with further ligation to the fragment (f). This resulted in a 3637 bp vector carrying a kanamycin resistance gene and promoter and regulatory region of human nephrin gene. Then the kanamycin resistance gene was cleaved by SpeI restriction sites, and the remaining fragment was ligated to itself. Thus, a 2620 bp recombinant gene therapy DNA vector GDTT1.8NAS7 enabling antibiotic-free selection and tissue-specific expression of therapeutic genes cloned into it mainly in renal podocytes (SEQ ID No. 7).

Example 8

Production of gene therapy DNA vector GDTT1.8NAS8 containing the promoter and regulatory region of the human common leukocyte antigen CD45 gene in order to increase the expression of therapeutic genes in hematopoietic cells.

The gene therapy DNA vector GDTT1.8NAS8 was constructed as described in Example 1, except that fragment (e), which is a promoter and regulatory region of human common leukocyte antigen CD45 gene, was obtained by PCR amplification of a region of human genomic DNA using cd45-F and cd45-R oligonucleotides (List of Sequences, (30)-(31)).

Then a 2408 bp intermediate vector carrying a kanamycin resistance gene, which still does not contain a promoter and regulatory region of the human common leukocyte antigen CD45 gene, was cleaved by restriction endonucleases in XhoI and BamHI sites with further ligation to the fragment (f). This resulted in a 3257 bp vector carrying a kanamycin resistance gene and promoter and regulatory region of human common leukocyte antigen CD45 gene. Then the kanamycin resistance gene was cleaved by SpeI restriction sites, and the remaining fragment was ligated to itself. Thus, a 2240 bp recombinant gene therapy DNA vector GDTT1.8NAS8 enabling antibiotic-free selection and tissue-specific expression of therapeutic genes cloned into it mainly in hematopoietic cells (SEQ ID No. 8).

Example 9

Production of gene therapy DNA vector GDTT1.8NAS9 containing the promoter and regulatory region of the human B29 protein gene in order to increase the expression of therapeutic genes in lymphocytes.

The gene therapy DNA vector GDTT1.8NAS9 was constructed as described in Example 1, except that fragment (e), which is a promoter and regulatory region of human B29 protein gene, was obtained by PCR amplification of a region of human genomic DNA using b29-F and b29-R oligonucleotides (List of Sequences, (32)-(33)).

Then a 2408 bp intermediate vector carrying a kanamycin resistance gene, which still does not contain a promoter and regulatory region of the human B29 protein gene, was cleaved by restriction endonucleases in XhoI and BamHI sites with further ligation to the fragment (f). This resulted in a 3621 bp vector carrying a kanamycin resistance gene and promoter and regulatory region of human B29 protein gene. Then the kanamycin resistance gene was cleaved by SpeI restriction sites, and the remaining fragment was ligated to itself. Thus, a 2604 bp recombinant gene therapy DNA vector GDTT1.8NAS9 enabling antibiotic-free selection and tissue-specific expression of therapeutic genes cloned into it mainly in lymphocytes (SEQ ID No. 9).

Example 10

Production of gene therapy DNA vector GDTT1.8NAS10 containing the promoter and regulatory region of the human CD68 protein gene in order to increase the expression of therapeutic genes in macrophages.

The gene therapy DNA vector GDTT1.8NAS10 was constructed as described in Example 1, except that fragment (e), which is a promoter and regulatory region of human CD68 protein gene, was obtained by PCR amplification of a region of human genomic DNA using cd68-F and cd68-R oligonucleotides (List of Sequences, (34)-(35)).

Then a 2408 bp intermediate vector carrying a kanamycin resistance gene, which still does not contain a promoter and regulatory region of the human CD68 protein gene, was cleaved by restriction endonucleases in XhoI and BglII sites with further ligation to the fragment (f). This resulted in a 3065 bp vector carrying a kanamycin resistance gene and promoter and regulatory region of human CD68 protein gene. Then the kanamycin resistance gene was cleaved by SpeI restriction sites, and the remaining fragment was ligated to itself. Thus, a 2048 bp recombinant gene therapy DNA vector GDTT1.8NAS10 enabling antibiotic-free selection and tissue-specific expression of therapeutic genes cloned into it mainly in macrophages (SEQ ID No. 10).

Example 11

Production of gene therapy DNA vector GDTT1.8NAS11 containing the promoter and regulatory region of the human insulin gene in order to increase the expression of therapeutic genes in beta cells of pancreas.

The gene therapy DNA vector GDTT1.8NAS11 was constructed as described in Example 1, except that fragment (e), which is a promoter and regulatory region of human insulin gene, was obtained by PCR amplification of a region of human genomic DNA using Ins-F and Ins-R oligonucleotides (List of Sequences, (36)-(37)).

Then a 2408 bp intermediate vector carrying a kanamycin resistance gene, which still does not contain a promoter and regulatory region of the human insulin gene, was cleaved by restriction endonucleases in XhoI and BamHI sites with further ligation to the fragment (f). This resulted in a 2995 bp vector carrying a kanamycin resistance gene and promoter and regulatory region of human insulin gene. Then the kanamycin resistance gene was cleaved by SpeI restriction sites, and the remaining fragment was ligated to itself. Thus, a 1978 bp recombinant gene therapy DNA vector GDTT1.8NAS11 enabling antibiotic-free selection and tissue-specific expression of therapeutic genes cloned into it mainly in beta cells of pancreas. (SEQ ID No. 11).

Example 12

Proof of the ability of gene therapy DNA vector GDTT1.8NAS1 to penetrate eukaryotic cells and its functional activity at the level of therapeutic gene mRNA expression and therapeutic protein. This example also demonstrates practicability of use of gene therapy DNA vector GDTT1.8NAS1.

For the validation of functional activity of DNA vector GDTT1.8NAS1 and practicability of its use, the therapeutic gene was cloned into a polylinker, e.g. the VEGF gene listed in the GenBank database with number NM_001025368.

Obtaining of gene therapy DNA vector GDTT1.8NAS1-VEGF carrying the therapeutic gene coding region, e.g. the VEGF gene. The coding region of VEGF gene was obtained by isolating total RNA from the biological human tissue sample followed by reverse transcription reaction using commercial kit Mint-2 (Evrogen, Russia) and PCR amplification using VEGF165_F and VEGF165_R oligonucleotides: (List of Sequences, (38) and (39)). The obtained PCR fragment was cleaved by BamHI and EcoRI restriction endonucleases and ligated with a 2753 bp DNA vector carrying the kanamycin resistance gene and cleaved by the same enzymes. Further on, the kanamycin resistance gene was removed from the vector produced, as described in Example 1. This resulted in a 2269 bp DNA vector GDTT1.8NAS1-VEGF allowing for antibiotic-free selection.

Changes in the mRNA accumulation of the VEGF therapeutic gene were assessed in HSkM human primary skeletal myoblast cell culture (ThermoFisher Scientific #A12555) before and 48 hours after their transfection with DNA vector GDTT1.8NAS1-VEGF carrying the human VEGF gene, and the quantitative content of the therapeutic VEGF protein was compared after transfection of these cells with the gene therapy DNA vector GDTT1.8NAS1-VEGF carrying the human VEGF gene and DNA vector GDTT1.8NAS1 not carrying the human VEGF gene.

HSkM cell culture was grown under standard conditions (37° C., 5% CO2) using the DMEM growth medium: The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS1-VEGF expressing the human VEGF gene was performed using Lipofectamine 3000 (ThermoFisher Scientific, USA) according to the manufacturer's recommendations. In test tube 1, 1 µl of DNA vector GDTT1.8NAS1-VEGF solution (concentration 500 ng/µl) and 1 µl of reagent P3000 was added to 25 µl of medium Opti-MEM (Gibco, USA). The preparation was mixed by gentle shaking. In test tube 2, 1 µl of Lipofectamine 3000 was added to 25 µl of medium Opti-MEM (Gibco, USA). The preparation was mixed by gentle shaking. The contents from test tube 1 were added to the contents of test tube 2, and the mixture was incubated at room temperature for 5 minutes. The resulting solution was added dropwise to the cells in the volume of 40 µl.

HSkM cells transfected with the gene therapy DNA vector GDTT1.8NAS1 devoid of the inserted therapeutic VEGF gene (cDNA of VEGF gene before and after transfection with gene therapy DNA vector GDTT1.8NAS1 devoid of the inserted therapeutic gene is not shown in the figures) were used as a reference. Reference vector GDTT1.8NAS1 for transfection was prepared as described above.

Total RNA from HSkM cells was extracted using Trizol Reagent (Invitrogen, USA) according to the manufacturer's recommendations. 1 ml of Trizol Reagent was added to the well with cells and homogenised and heated for 5 minutes at 65° C. Then the sample was centrifuged at 14,000 g for 10 minutes and heated again for 10 minutes at 65° C. Then 200 µl of chloroform was added, and the mixture was gently stirred and centrifuged at 14,000 g for 10 minutes. Then the water phase was isolated and mixed with 1/10 of the volume of 3M sodium acetate, pH 5.2, and an equal volume of isopropyl alcohol. The sample was incubated at −20° C. for 10 minutes and then centrifuged at 14,000 g for 10 minutes. The precipitated RNA was rinsed in 1 ml of 70% ethyl alcohol, air-dried and dissolved in 10 µl of RNase-free water. The level of VEGF mRNA expression after transfection was determined by assessing the dynamics of the accumulation of cDNA amplicons by real-time PCR. For the production and amplification of cDNA specific for the human VEGF gene, the VEGF165_SF and VEGF165_SK oligonucleotides were used (list of sequences (40) and (41)). The length of amplification product is 576 bp.

Reverse transcription reaction and PCR amplification was performed using Quantitect SYBR Green RT-PCR Kit (Qiagen, USA) for real-time PCR. The reaction was carried out in a volume of 20 µl, containing: 25 µl of QuantiTect SYBR Green RT-PCR Master Mix, 2.5 mM of magnesium chloride, 0.5 µM of each primer, and 5 µl of RNA. For the reaction, CFX96 amplifier (Bio-Rad, USA) was used under the following conditions: 1 cycle of reverse transcription at 42° C. for 30 minutes, denaturation at 98° C. for 15 minutes, followed by 40 cycles comprising denaturation at 94° C. for 15 s, annealing of primers at 60° C. for 30 s and elongation at 72° C. for 30 s. B2M (human beta-2-microglobuline) gene listed in the GenBank database under number NM 004048.2 was used as a reference gene. Positive control included amplicons from PCR on matrices represented by plasmids in known concentrations containing cDNA sequences of VEGF and B2M genes. Negative control included deionised water. Real-time quantification of the dynamics of accumulation of cDNA amplicons of VEGF and B2M genes was conducted using the Bio-Rad CFX Manager 2.1 software (Bio-Rad, USA). Diagrams resulting from the assay are shown in FIG. 13.

The VEGF protein was assayed by enzyme-linked immunosorbent assay (ELISA) using the ELISA Kit for Vascular Endothelial Growth Factor A (VEGFA), Cloud-Clone Corp., USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of VEGF protein was used. The sensitivity was at least 6.2 pg/ml, measurement range—from 15.6 pg/ml to 1000 pg/ml. R-3.0.2 was used for the statistical treatment of the results and data visualization (https://www.r-project.org/). Drawings resulting from the assay are shown in FIG. 14.

FIG. 13 shows that the level of specific mRNA of human VEGF gene has grown massively as a result of transfection of HSkM primary human skeletal myoblast cell culture with gene therapy DNA vector GDTT1.8NAS1-VEGF, which confirms the ability of the vector to penetrate eukaryotic cells and express the VEGF gene at the mRNA level. FIG. 14 shows that the transfection of HSkM primary human skeletal myoblast cell culture with gene therapy DNA vector GDTT1.8NAS1-VEGF results in increased VEGF protein concentration compared to reference samples, which confirms the ability of the vector to penetrate eukaryotic cells and express the VEGF gene at the protein level.

The presented results also confirm the practicability of use of gene therapy DNA vector GDTT1.8NAS1-VEGF in order to increase the expression level of VEGF gene in eukaryotic cells.

Example 13

Proof of the ability of gene therapy DNA vector GDTT1.8NAS2 to penetrate eukaryotic cells and its functional activity at the level of therapeutic gene mRNA expression and therapeutic protein. This example also demonstrates practicability of use of gene therapy DNA vector GDTT1.8NAS2.

For the validation of functional activity of DNA vector GDTT1.8NAS2 and practicability of its use, the therapeutic gene was cloned into a polylinker, e.g. the VEGF gene listed in the GenBank database with number NM_001025368. Obtaining of gene therapy DNA vector GDTT1.8NAS2-CAT carrying the therapeutic gene coding region, e.g. the CAT gene. The coding region of CAT gene was obtained by isolating total RNA from the biological human tissue sample followed by reverse transcription reaction using commercial kit Mint-2 (Evrogen, Russia) and PCR amplification using CAT_F and CAT_R oligonucleotides: (List of Sequences, (42) and (43)). The obtained PCR fragment was cleaved by EcoRV and XbaI restriction endonucleases and ligated with a 2671 bp DNA vector carrying the kanamycin resistance gene and cleaved by the same enzymes. Further on, the kanamycin resistance gene was removed from the vector produced, as described in Example 1. This resulted in a 3237 bp DNA vector GDTT1.8NAS2-CAT allowing for antibiotic-free selection.

Changes in the mRNA accumulation of the CAT therapeutic gene were assessed in human primary dermal fibroblast cell culture HDFa (ATCC® PCS-201-012™) before and 48 hours after their transfection with DNA vector GDTT1.8NAS2-CAT carrying the human CAT gene, and the quantitative content of the therapeutic CAT protein was compared after transfection of these cells with the gene therapy DNA vector GDTT1.8NAS2-CAT carrying the human CAT gene and DNA vector GDTT1.8NAS2 not carrying the human CAT gene.

HDFa cell culture was grown under standard conditions (37° C., 5% CO2) using the Fibroblast Growth Kit-Serum-Free (ATCC® PCS-201-040). The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS2-CAT expressing the human CAT gene was performed using Lipofectamine 3000 (ThermoFisher Scientific, USA) as described in Example 12. HDFa cells transfected with the gene therapy DNA vector GDTT1.8NAS2 devoid of the inserted therapeutic CAT gene (cDNA of CAT gene before and after transfection with gene therapy DNA vector GDTT1.8NAS2 devoid of the inserted therapeutic gene is not shown in the figures) were used as a reference. Reference vector GDTT1.8NAS2 for transfection was prepared as described above.

Total RNA from HDFa cells was extracted using Trizol Reagent (Invitrogen, USA) as described in Example 12. The level of CAT mRNA expression after transfection was determined by assessing the dynamics of the accumulation of cDNA amplicons by real-time PCR as described in Example 12. For the production and amplification of cDNA specific for the human CAT gene, the CAT_SF and CAT_SR oligonucleotides were used (list of sequences (44) and (45)). The length of amplification product is 272 bp.

Diagrams resulting from the assay are shown in FIG. 15.

The CAT protein was assayed by enzyme-linked immunosorbent assay (ELISA) using the ELISA Kit for Catalase (CAT) Cloud-Clone Corp. according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of CAT protein was used. The sensitivity was at least 0.124 ng/ml, measurement range—from 0.312 ng/ml to 20 ng/ml. R-3.0.2 was used for the statistical treatment of the results and data visualization (https://www.r-project.org/). Drawings resulting from the assay are shown in FIG. 16.

FIG. 15 shows that the level of specific mRNA of human CAT gene has grown massively as a result of transfection of HDFa human primary dermal fibroblast cell culture with gene therapy DNA vector GDTT1.8NAS2-CAT, which confirms the ability of the vector to penetrate eukaryotic cells and express the CAT gene at the mRNA level. FIG. 16 shows that the transfection of HDFa human primary dermal fibroblast cell culture with gene therapy DNA vector GDTT1.8NAS2-CAT results in increased CAT protein concentration compared to reference samples, which confirms the ability of the vector to penetrate eukaryotic cells and express the CAT gene at the protein level.

The presented results also confirm the practicability of use of gene therapy DNA vector GDTT1.8NAS2-CAT in order to increase the expression level of CAT gene in eukaryotic cells.

Example 14

Proof of the ability of gene therapy DNA vector GDTT1.8NAS3 to penetrate eukaryotic cells and its functional activity at the level of therapeutic gene mRNA expression and therapeutic protein. This example also demonstrates practicability of use of gene therapy DNA vector GDTT1.8NAS3.

For the validation of functional activity of DNA vector GDTT1.8NAS3 and practicability of its use, the therapeutic gene was cloned into a polylinker, e.g. the HIF1a gene listed in the GenBank database with number NM_001530. Obtaining of gene therapy DNA vector GDTT1.8NA3-HIF1a carrying the therapeutic gene coding region, e.g. the HIF1a gene. The coding region of HIF1a gene was obtained by isolating total RNA from the biological human tissue sample followed by reverse transcription reaction using commercial kit Mint-2 (Evrogen, Russia) and PCR amplification using HIF1a_F and HIF1a_R oligonucleotides: (List of Sequences, (46) and (47)). The obtained PCR fragment was cleaved by BamHI and XbaI restriction endonucleases and ligated with a 2800 bp DNA vector carrying the kanamycin resistance gene and cleaved by the same enzymes. Further on, the kanamycin resistance gene was removed from the vector produced, as described in Example 1. This resulted in a 4257 bp DNA vector GDTT1.8NAS3-HIF1a allowing for antibiotic-free selection.

Changes in the mRNA accumulation of the HIF1a therapeutic gene were assessed in human umbilical vein endothelial cells HUVEC (ATCC® PCS-100-013™) before and 48 hours after their transfection with DNA vector GDTT1.8NAS3-HIF1a carrying the human HIF1a gene, and the quantitative content of the therapeutic HIF1a protein was compared after transfection of these cells with the gene therapy DNA vector GDTT1.8NAS3-HIF1a carrying the human HIF1a gene and DNA vector GDTT1.8NAS3 not carrying the human HIF1a gene.

HUVEC cell culture was grown under standard conditions (37° C., 5% CO2) using the Endothelial Cell Growth Kit-BBE (ATCC® PCS-100-040). The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS3-HIF1a expressing the human HIF1a gene was performed using Lipofectamine 3000 (ThermoFisher Scientific, USA) as described in Example 12.

HUVEC cells transfected with the gene therapy DNA vector GDTT1.8NAS3 devoid of the inserted therapeutic HIF1a gene (cDNA of HIF1a gene before and after transfection with gene therapy DNA vector GDTT1.8NAS3 devoid of the inserted therapeutic gene is not shown in the figures) were used as a reference. Reference vector GDTT1.8NAS3 for transfection was prepared as described above.

Total RNA from HUVEC cells was extracted using Trizol Reagent (Invitrogen, USA) as described in Example 12. The level of HIF1a mRNA expression after transfection was determined by assessing the dynamics of the accumulation of cDNA amplicons by real-time PCR as described in Example 12. For the production and amplification of cDNA specific for the human HIF1a gene, the HIF1a_SF and HIF1a_SR oligonucleotides were used (list of sequences (48) and (49)). The length of amplification product is 379 bp.

Diagrams resulting from the assay are shown in FIG. 17.

The HIF1a protein was assayed by enzyme-linked immunosorbent assay (ELISA) using the ELISA Kit for Hypoxia Inducible Factor 1 Alpha (HIF1a), Cloud-Clone Corp., USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of HIF1a protein was used. The sensitivity was at least 0.054 ng/ml, measurement range—from 0.156 ng/ml to 10 ng/ml. R-3.0.2 was used for the statistical treatment of the results and data visualization (https://www.r-project.org/). Drawings resulting from the assay are shown in FIG. 18.

FIG. 17 shows that the level of specific mRNA of human HIF1a gene has grown massively as a result of transfection of HUVEC human umbilical vein endothelial cells with gene therapy DNA vector GDTT1.8NAS3-HIF1a, which confirms the ability of the vector to penetrate eukaryotic cells and express the HIF1a gene at the mRNA level. FIG. 18 shows that the transfection of HUVEC human umbilical vein endothelial cell culture with gene therapy DNA vector GDTT1.8NAS3-HIF1a results in increased HIF1a protein concentration compared to reference samples, which confirms the ability of the vector to penetrate eukaryotic cells and express the HIF1a gene at the protein level.

The presented results also confirm the practicability of use of gene therapy DNA vector GDTT1.8NAS3-HIF1a in order to increase the expression level of HIF1a gene in eukaryotic cells.

Example 15

Proof of the ability of gene therapy DNA vector GDTT1.8NAS4 to penetrate eukaryotic cells and its functional activity at the level of therapeutic gene mRNA expression and therapeutic protein. This example also demonstrates practicability of use of gene therapy DNA vector GDTT1.8NAS4.

For the validation of functional activity of DNA vector GDTT1.8NAS4 and practicability of its use, the therapeutic gene was cloned into a polylinker, e.g. the BMP2 gene listed in the GenBank database with number NM_001200. Obtaining of gene therapy DNA vector GDTT1.8NAS4-BMP2 carrying the therapeutic gene coding region, e.g. the BMP2 gene. The coding region of BMP2 gene was obtained by isolating total RNA from the biological human tissue sample followed by reverse transcription reaction using commercial kit Mint-2 (Evrogen, Russia) and PCR amplification using BMP2_F and BMP2_R oligonucleotides: (List of Sequences, (50) and (51)). The obtained PCR fragment was cleaved by BamHI and EcoRI restriction endonucleases and ligated with a 2970 bp DNA vector carrying the kanamycin resistance gene and cleaved by the same enzymes. Further on, the kanamycin resistance gene was removed from the vector produced, as described in Example 1. This resulted in a 3104 bp DNA vector GDTT1.8NAS4-BMP2 allowing for antibiotic-free selection.

Changes in the mRNA accumulation of the BMP2 therapeutic gene were assessed in human osteosarcoma cells MG-63 (ATCC® CRL-1427™) before and 48 hours after their transfection with DNA vector GDTT1.8NAS4-BMP2 carrying the human BMP2 gene, and the quantitative content of the therapeutic BMP2 protein was compared after transfection of these cells with the gene therapy DNA vector GDTT1.8NAS4-BMP2 carrying the human BMP2 gene and DNA vector GDTT1.8NAS4 not carrying the human BMP2 gene.

MG-63 cell culture was grown under standard conditions (37° C., 5% CO2) using the DMEM (Gibco) growth medium with the addition of 10% fetal bovine serum (Gibco). The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS4-BMP2 expressing the human BMP2 gene was performed using Lipofectamine 3000 (ThermoFisher Scientific, USA) as described in Example 12.

MG-63 cells transfected with the gene therapy DNA vector GDTT1.8NAS4 devoid of the inserted therapeutic BMP2 gene (cDNA of BMP2 gene before and after transfection with gene therapy DNA vector GDTT1.8NAS4 devoid of the inserted therapeutic gene is not shown in the figures) were used as a reference. Reference vector GDTT1.8NAS4 for transfection was prepared as described above.

Total RNA from MG-63 cells was extracted using Trizol Reagent (Invitrogen, USA) as described in Example 12. The level of BMP2 mRNA expression after transfection was determined by assessing the dynamics of the accumulation of cDNA amplicons by real-time PCR as described in Example 12. For the production and amplification of cDNA specific for the human BMP2 gene, the BMP2_SF and BMP2_SR oligonucleotides were used (list of sequences (52) and (53)). The length of amplification product is 353 bp.

Diagrams resulting from the assay are shown in FIG. 19.

The BMP2 protein was assayed by enzyme-linked immunosorbent assay (ELISA) using the ELISA Kit for Bone Morphogenetic Protein 2 (BMP2), Cloud-Clone Corp, USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of BMP2 protein was used. The sensitivity was at least 6.1 pg/ml, measurement range—from 15.6 pg/ml to 1000 pg/ml. R-3.0.2 was used for the statistical treatment of the results and data visualization (https://www.r-project.org/). Drawings resulting from the assay are shown in FIG. 20.

FIG. 19 shows that the level of specific mRNA of human BMP2 gene has grown massively as a result of transfection of MG-63 human osteosarcoma cell culture with gene therapy DNA vector GDTT1.8NAS4-BMP2, which confirms the ability of the vector to penetrate eukaryotic cells and express the BMP2 gene at the mRNA level. FIG. 20 shows that the transfection of MG-63 human osteosarcoma cell culture with gene therapy DNA vector GDTT1.8NAS4-BMP2 results in increased BMP2 protein concentration compared to the reference samples, which confirms the ability of the vector to penetrate eukaryotic cells and express the BMP2 gene at the protein level.

The presented results also confirm the practicability of use of gene therapy DNA vector GDTT1.8NAS4-BMP2 in order to increase the expression level of BMP2 gene in eukaryotic cells.

Example 16

Proof of the ability of gene therapy DNA vector GDTT1.8NAS5 to penetrate eukaryotic cells and its functional activity at the level of therapeutic gene mRNA expression and therapeutic protein. This example also demonstrates practicability of use of gene therapy DNA vector GDTT1.8NAS5.

For the validation of functional activity of DNA vector GDTT1.8NAS5 and practicability of its use, the therapeutic gene was cloned into a polylinker, e.g. the CFTR gene listed in the GenBank database with number NM_000492. Obtaining of gene therapy DNA vector GDTT1.8NAS5-CFTR carrying the therapeutic gene coding region, e.g. the CFTR gene. The coding region of CFTR gene was obtained by isolating total RNA from the biological human tissue sample followed by reverse transcription reaction using commercial kit Mint-2 (Evrogen, Russia) and PCR amplification using CFTR_F and CFTR_R oligonucleotides: (List of Sequences, (54) and (55)). The obtained PCR fragment was cleaved by SalI and NotI restriction endonucleases and ligated with a 3036 bp DNA vector carrying the kanamycin resistance gene and cleaved by the same enzymes. Further on, the kanamycin resistance gene was removed from the vector produced, as described in Example 1. This resulted in a 6448 bp DNA vector GDTT1.8NAS5-CFR allowing for antibiotic-free selection.

Changes in the mRNA accumulation of the CFTR therapeutic gene were assessed in human tracheal epithelial cells CFTE29o-(Collection of Institute of Cytology RAS) before and 48 hours after their transfection with DNA vector GDTT1.8NA5-CFTR carrying the human CFTR gene, and the quantitative content of the therapeutic CFTR protein was compared after transfection of these cells with the gene therapy DNA vector GDTT1.8NAS5-CFTR carrying the human CFTR gene and DNA vector GDTT1.8NAS5 not carrying the human CFTR gene.

CFTE29o-cell culture was grown under standard conditions (37° C., 5% CO2) using the DMEM (Gibco) growth medium with the addition of 10% fetal bovine serum (Gibco). The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS5-CFTR expressing the human CFTR gene was performed using Lipofectamine 3000 (ThermoFisher Scientific, USA) as described in Example 12.

CFTE29o-cells transfected with the gene therapy DNA vector GDTT1.8NAS5 devoid of the inserted therapeutic CFTR gene (cDNA of CFTR gene before and after transfection with gene therapy DNA vector GDTT1.8NAS5 devoid of the inserted therapeutic gene is not shown in the figures) were used as a reference. Reference vector GDTT1.8NAS5 for transfection was prepared as described above.

Total RNA from CFTE29o-cells was extracted using Trizol Reagent (Invitrogen, USA) as described in Example 12. The level of CFTR mRNA expression after transfection was determined by assessing the dynamics of the accumulation of cDNA amplicons by real-time PCR as described in Example 12. For the production and amplification of cDNA specific for the human CFTR gene, CFTR_SF and CFTR_SR oligonucleotides were used (list of sequences, (56) and (57)). The length of the amplification product is 328 bp.

Diagrams resulting from the assay are shown in FIG. 21.

The CFTR protein was assayed by enzyme-linked immunosorbent assay (ELISA) using the ELISA Kit for Cystic Fibrosis Transmembrane Conductance Regulator (CFTR), Cloud-Clone Corp, USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of CFTR protein was used. The sensitivity is 0.059 ng/ml, measurement range—0.156-10 ng/ml. R-3.0.2 was used for the statistical treatment of the results and data visualization (https://www.r-project.org/). Drawings resulting from the assay are shown in FIG. 22.

FIG. 21 shows that the level of specific mRNA of human CFTR gene has grown massively as a result of transfection of CFTE29o-human tracheal epithelial cell culture with gene therapy DNA vector GDTT1.8NAS5-CFTR, which confirms the ability of the vector to penetrate eukaryotic cells and express the CFTR gene at the mRNA level. FIG. 22 shows that the transfection of CFTE29o-human tracheal epithelial cell culture with gene therapy DNA vector GDTT1.8NAS5-CFTR results in increased CFTR protein concentration compared to the reference samples, which confirms the ability of the vector to penetrate eukaryotic cells and express the CFTR gene at the protein level.

The presented results also confirm the practicability of use of gene therapy DNA vector GDTT1.8NAS5-CFTR in order to increase the expression level of CFTR gene in eukaryotic cells.

Example 17

Proof of the ability of gene therapy DNA vector GDTT1.8NAS6 to penetrate eukaryotic cells and its functional activity at the level of therapeutic gene mRNA expression and therapeutic protein. This example also demonstrates practicability of use of gene therapy DNA vector GDTT1.8NAS6.

For the validation of functional activity of DNA vector GDTT1.8NAS6 and practicability of its use, the therapeutic gene was cloned into a polylinker, e.g. the BDNF gene listed in the GenBank database with number NM_170735. Obtaining of gene therapy DNA vector GDTT1.8NAS6-BDNF carrying the therapeutic gene coding region, e.g. the BDNF gene. The coding region of BDNF gene was obtained by isolating total RNA from the biological human tissue sample followed by reverse transcription reaction using commercial kit Mint-2 (Evrogen, Russia) and PCR amplification using BDNF_F and BDNF_R oligonucleotides: (List of Sequences, (58) and (59)). The obtained PCR fragment was cleaved by BamHI and EcoRI restriction endonucleases and ligated with a 2957 bp DNA vector carrying the kanamycin resistance gene and cleaved by the same enzymes. Further on, the kanamycin resistance gene was removed from the vector produced, as described in Example 1. This resulted in a 2637 bp DNA vector GDTT1.8NAS6-BDNF allowing for antibiotic-free selection.

Changes in the mRNA accumulation of the BDNF therapeutic gene were assessed in human neuroblastoma cell culture SH-SY5Y (ATCC® CRL-2266™) before and 48 hours after their transfection with DNA vector GDTT1.8NAS6-BDNF carrying the human BDNF gene, and the quantitative content of the therapeutic BDNF protein was compared after transfection of these cells with the gene therapy DNA vector GDTT1.8NAS6-BDNF carrying the human BDNF gene and DNA vector GDTT1.8NAS6 not carrying the human BDNF gene.

SH-SY5Y cell culture was grown under standard conditions (37° C., 5% CO2) using a mixture of the following growth media (1:1) ATCC-formulated Eagle's Minimum Essential Medium (ATCC) and F12 Medium (Gibco). The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS6-BDNF expressing the human BDNF gene was performed using Lipofectamine 3000 (ThermoFisher Scientific, USA) as described in Example 12. SH-SY5Y cells transfected with the gene therapy DNA vector GDTT1.8NAS6 devoid of the inserted therapeutic BDNF gene (cDNA of BDNF gene before and after transfection with gene therapy DNA vector GDTT1.8NAS6 devoid of the inserted therapeutic gene is not shown in the figures) were used as a reference. Reference vector GDTT1.8NAS6 for transfection was prepared as described above.

Total RNA from SH-SY5Y cells was extracted using Trizol Reagent (Invitrogen, USA) as described in Example 12. The level of BDNF mRNA expression after transfection was determined by assessing the dynamics of the accumulation of cDNA amplicons by real-time PCR as described in Example 12. For the production and amplification of cDNA specific for the human BDNF gene, the BDNF_SF and BDNF_SR oligonucleotides were used (list of sequences (60) and (61)). The length of amplification product is 199 bp.

Diagrams resulting from the assay are shown in FIG. 23.

The BDNF protein was assayed by enzyme-linked immunosorbent assay (ELISA) using the ELISA Kit for Brain Derived Neurotrophic Factor (BDNF), Cloud-Clone Corp, USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of BDNF protein was used. The sensitivity was at least 12.6 pg/ml, measurement range—from 31.2 pg/ml to 2000 pg/ml. R-3.0.2 was used for the statistical treatment of the results and data visualization (https://www.r-project.org/). Drawings resulting from the assay are shown in FIG. 24.

FIG. 23 shows that the level of specific mRNA of human BDNF gene has grown massively as a result of transfection of SH-SY5Y human neuroblastoma cell culture with gene therapy DNA vector GDTT1.8NAS6-BDNF, which confirms the ability of the vector to penetrate eukaryotic cells and express the BDNF gene at the mRNA level. FIG. 24 shows that the transfection of SH-SY5Y human neuroblastoma cell culture with gene therapy DNA vector GDTT1.8NAS6-BDNF results in increased BDNF protein concentration compared to reference samples, which confirms the ability of the vector to penetrate eukaryotic cells and express the BDNF gene at the mRNA level.

The presented results also confirm the practicability of use of gene therapy DNA vector GDTT1.8NAS6-BDNF in order to increase the expression level of BDNF gene in eukaryotic cells.

Example 18

Proof of the ability of gene therapy DNA vector GDTT1.8NAS7 to penetrate eukaryotic cells and its functional activity at the level of therapeutic gene mRNA expression and therapeutic protein. This example also demonstrates practicability of use of gene therapy DNA vector GDTT1.8NAS7.

For the validation of functional activity of DNA vector GDTT1.8NAS7 and practicability of its use, the therapeutic gene was cloned into a polylinker, e.g. the ATGL gene listed in the GenBank database with number NM_020376. Obtaining of gene therapy DNA vector GDTT1.8NAS7-ATGLF carrying the therapeutic gene coding region, e.g. the ATGL gene. The coding region of ATGL gene was obtained by isolating total RNA from the biological human tissue sample followed by reverse transcription reaction using commercial kit Mint-2 (Evrogen, Russia) and PCR amplification using ATGL_F and ATGL_R oligonucleotides: (List of Sequences, (62) and (63)). The obtained PCR fragment was cleaved by BamHI and EcoRI restriction endonucleases and ligated with a 3637 bp DNA vector carrying the kanamycin resistance gene and cleaved by the same enzymes. Further on, the kanamycin resistance gene was removed from the vector produced, as described in Example 1. This resulted in a 4088 bp DNA vector GDTT1.8NAS7-ATGL allowing for antibiotic-free selection.

Changes in the mRNA accumulation of the ATGL therapeutic gene were assessed in primary human kidney epithelial mixed cell culture HREC (ATCC® PCS-400-012™) before and 48 hours after their transfection with DNA vector GDTT1.8NAS7-ATGL carrying the human ATGL gene, and the quantitative content of the therapeutic ATGL protein was compared after transfection of these cells with the gene therapy DNA vector GDTT1.8NAS7-ATGL carrying the human ATGL gene and DNA vector GDTT1.8NAS7 not carrying the human ATGL gene.

HREC cell culture was grown under standard conditions (37° C., 5% CO2) using the Renal Epithelial Cell Growth Kit (ATCC). The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS7-ATGL expressing the human ATGL gene was performed using Lipofectamine 3000 (ThermoFisher Scientific, USA) as described in Example 12.

HREC cells transfected with the gene therapy DNA vector GDTT1.8NAS7 devoid of the inserted therapeutic ATGL gene (cDNA of ATGL gene before and after transfection with gene therapy DNA vector GDTT1.8NAS7 devoid of the inserted therapeutic gene is not shown in the figures) were used as a reference. Reference vector GDTT1.8NAS7 for transfection was prepared as described above.

Total RNA from HREC cells was extracted using Trizol Reagent (Invitrogen, USA) as described in Example 12. The level of ATGL mRNA expression after transfection was determined by assessing the dynamics of the accumulation of cDNA amplicons by real-time PCR as described in Example 12. For the production and amplification of cDNA specific for the human ATGL gene, ATGL_SF and ATGL_SR oligonucleotides were used (list of sequences, (64) and (65)). The length of amplification product is 417 bp.

Diagrams resulting from the assay are shown in FIG. 25.

The ATGL protein was assayed by enzyme-linked immunosorbent assay (ELISA) using the ELISA Kit for Patatin Like Phospholipase Domain Containing Protein 2 (PN-PLA2), Cloud-Clone Corp, USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of ATGL protein was used. The sensitivity was at least 0.128 ng/ml, measurement range—from 0,312 ng/ml to 20 ng/ml. R-3.0.2 was used for the statistical treatment of the results and data visualization (https://www.r-project.org/). Drawings resulting from the assay are shown in FIG. 26.

FIG. 25 shows that the level of specific mRNA of human ATGL gene has grown massively as a result of transfection of HREC primary human kidney epithelial mixed cell culture with gene therapy DNA vector GDTT1.8NAS7-ATGL, which confirms the ability of the vector to penetrate eukaryotic cells and express the ATGL gene at the mRNA level. FIG. 26 shows that the transfection of HREC primary human kidney epithelial mixed cell culture with gene therapy DNA vector GDTT1.8NAS7-ATGL results in increased ATGL protein concentration compared to reference samples, which confirms the ability of the vector to penetrate eukaryotic cells and express the ATGL gene at the protein level.

The presented results also confirm the practicability of use of gene therapy DNA vector GDTT1.8NAS7-ATGL in order to increase the expression level of ATGL gene in eukaryotic cells.

Example 19

Proof of the ability of gene therapy DNA vector GDTT1.8NAS8 to penetrate eukaryotic cells and its functional activity at the level of therapeutic gene mRNA expression and therapeutic protein. This example also demonstrates practicability of use of gene therapy DNA vector GDTT1.8NAS8.

For the validation of functional activity of DNA vector GDTT1.8NAS8 and practicability of its use, the therapeutic gene was cloned into a polylinker, e.g. the CAS9 gene listed in the GenBank database with number EZM83080.1.

Obtaining of gene therapy DNA vector GDTT1.8NAS8-CAS9 carrying the therapeutic gene coding region, e.g. the CAS9 gene. The coding region of CAS9 gene was obtained by isolating total RNA from the biological human tissue sample followed by reverse transcription reaction using commercial kit Mint-2 (Evrogen, Russia) and PCR amplification using CAS9_F and CAS9_R oligonucleotides: (List of Sequences, (66) and (67)). The obtained PCR fragment was cleaved by BamHI and EcoRI restriction endonucleases and ligated with a 3257 bp DNA vector carrying the kanamycin resistance gene and cleaved by the same enzymes. Further on, the kanamycin resistance gene was removed from the vector produced, as described in Example 1. This resulted in a 6461 bp DNA vector GDTT1.8NAS8-CAS9 allowing for antibiotic-free selection.

Changes in the mRNA accumulation of the CAS9 therapeutic gene were assessed in primary human bone marrow cell culture (ATCC® PCS-800-012™) before and 48 hours after their transfection with DNA vector GDTT1.8NAS8-CAS9 carrying the human CAS9 gene, and the quantitative content of the therapeutic CAS9 protein was compared after transfection of these cells with the gene therapy DNA vector GDTT1.8NAS8-CAS9 carrying the human CAT gene and DNA vector GDTT1.8NAS8 not carrying the human CAS9 gene.

Human primary bone marrow cell culture CD34 (ATCC® PCS-800-012™) was thawed 24 hours before transfection and transferred to a 24-well plate in Hanks' solution with the addition of 10% fetal bovine serum (Gibco) in the quantity of 5×104 cells per well. Transfection with gene therapy DNA vector GDTT1.8NAS8-CAS9 expressing the human CAS9 gene was performed using Lipofectamine 3000 (ThermoFisher Scientific, USA) as described in Example 12.

Human bone marrow cells transfected with the gene therapy DNA vector GDTT1.8NAS8 devoid of the inserted therapeutic CAS9 gene (cDNA of CAS9 gene before and after transfection with gene therapy DNA vector GDTT1.8NAS8 devoid of the inserted therapeutic gene is not shown in the figures) were used as a reference. Reference vector GDTT1.8NAS8 for transfection was prepared as described above.

Total RNA from human bone marrow cells was extracted using Trizol Reagent (Invitrogen, USA) as described in Example 12. The level of CAS9 mRNA expression after transfection was determined by assessing the dynamics of the accumulation of cDNA amplicons by real-time PCR as described in Example 12. For the production and amplification of cDNA specific for the human CAS9 gene, the CAS9_SF and CAS9_SR oligonucleotides were used (list of sequences (68) and (69)).

The length of amplification product is 275 bp.

Diagrams resulting from the assay are shown in FIG. 27.

The CAS9 protein was assayed by enzyme-linked immunosorbent assay (ELISA) using Cas9 (CRISPR Associated Protein 9) ELISA Kit, Cell Biolabs Inc, according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of CAS9 protein was used. The sensitivity was at least 1.5 ng/ml, measurement range—from 1.56 ng/ml to 100 ng/ml. R-3.0.2 was used for the statistical treatment of the results and data visualization (https://www.r-project.org/). Drawings resulting from the assay are shown in FIG. 28.

FIG. 27 shows that the level of specific mRNA of human CAS9 gene has grown massively as a result of transfection of human primary bone marrow cell culture with gene therapy DNA vector GDTT1.8NAS8-CAS9, which confirms the ability of the vector to penetrate eukaryotic cells and express the CAS9 gene at the mRNA level. FIG. 28 shows that the transfection of human primary bone marrow cell culture with gene therapy DNA vector GDTT1.8NAS8-CAS9 results in increased CAS9 protein concentration compared to reference samples, which confirms the ability of the vector to penetrate eukaryotic cells and express the CAS9 gene at the protein level.

The presented results also confirm the practicability of use of gene therapy DNA vector GDTT1.8NAS8-CAS9 in order to increase the expression level of CAS9 gene in eukaryotic cells.

Example 20

Proof of the ability of gene therapy DNA vector GDTT1.8NAS9 to penetrate eukaryotic cells and its functional activity at the level of therapeutic gene mRNA expression and therapeutic protein. This example also demonstrates practicability of use of gene therapy DNA vector GDTT1.8NAS9.

For the validation of functional activity of DNA vector GDTT1.8NAS9 and practicability of its use, the therapeutic gene was cloned into a polylinker, e.g. the BTK gene listed in the GenBank database with number NM_000061. Obtaining of gene therapy DNA vector GDTT1.8NAS9-BTK carrying the therapeutic gene coding region, e.g. the BTK gene. The coding region of BTK gene was obtained by isolating total RNA from the biological human tissue sample followed by reverse transcription reaction using commercial kit Mint-2 (Evrogen, Russia) and PCR amplification using BTK_F and BTK_R oligonucleotides: (List of Sequences, (70) and (71)). The obtained PCR fragment was cleaved by BamHI and EcoRI restriction endonucleases and ligated with a 3621 bp DNA vector carrying the kanamycin resistance gene and cleaved by the same enzymes. Further on, the kanamycin resistance gene was removed from the vector produced, as described in Example 1. This resulted in a 2637 bp DNA vector GDTT1.8NAS9-BTK allowing for antibiotic-free selection.

Changes in the mRNA accumulation of the BTK therapeutic gene were assessed in primary human peripheral blood mononuclear cell culture PBMC (ATCC® PCS-800-011™) before and 48 hours after their transfection with DNA vector GDTT1.8NAS9-BTK carrying the human BTK gene, and the quantitative content of the therapeutic BTK protein was compared after transfection of these cells with the gene therapy DNA vector GDTT1.8NAS9-BTK carrying the human BTK gene and DNA vector GDTT1.8NAS8 not carrying the human BTK gene.

PBMC cell culture was thawed 24 hours before transfection and transferred to a 10-well plate in Hanks' solution with the addition of 5% fetal bovine serum (Gibco) in the quantity of 5×104 cells per well. Transfection with gene therapy DNA vector GDTT1.8NAS9-BTK expressing the human BTK gene was performed using Lipofectamine 3000 (ThermoFisher Scientific, USA) as described in Example 12. PBMC cells transfected with the gene therapy DNA vector GDTT1.8NAS9 devoid of the inserted therapeutic BTK gene (cDNA of BTK gene before and after transfection with gene therapy DNA vector GDTT1.8NAS9 devoid of the inserted therapeutic gene is not shown in the figures) were used as a reference. Reference vector GDTT1.8NAS9 for transfection was prepared as described above.

Total RNA from PBMC cells was extracted using Trizol Reagent (Invitrogen, USA) as described in Example 12. The level of BTK mRNA expression after transfection was determined by assessing the dynamics of the accumulation of cDNA amplicons by real-time PCR as described in Example 12. For the production and amplification of cDNA specific for the human BTK gene, the BTK_SF and BTK_SR oligonucleotides were used (list of sequences (72) and (73)). The length of amplification product is 579 bp.

Diagrams resulting from the assay are shown in FIG. 29.

The BTK protein was assayed by enzyme-linked immunosorbent assay (ELISA) using the ELISA Kit for Bruton'S Tyrosine Kinase (Btk), Cloud-Clone Corp, USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of BTK protein was used. The sensitivity was at least 0.055 ng/ml, measurement range—from 0,156 ng/ml to 10 ng/ml. R-3.0.2 was used for the statistical treatment of the results and data visualization (https://www.r-project.org/). Drawings resulting from the assay are shown in FIG. 30.

FIG. 29 shows that the level of specific mRNA of human BTK gene has grown massively as a result of transfection of primary human peripheral blood mononuclear cell culture PBMC with gene therapy DNA vector GDTT1.8NAS9-BTK, which confirms the ability of the vector to penetrate eukaryotic cells and express the BTK gene at the mRNA level. FIG. 30 shows that the transfection of primary human peripheral blood mononuclear cell culture PBMC with gene therapy DNA vector GDTT1.8NAS9-BTK results in increased BTK protein level compared to reference samples which confirms the ability of the vector to penetrate eukaryotic cells and express the BTK gene at the protein level.

The presented results also confirm the practicability of use of gene therapy DNA vector GDTT1.8NAS9-BTK in order to increase the expression level of BTK gene in eukaryotic cells.

Example 21

Proof of the ability of gene therapy DNA vector GDTT1.8NAS10 to penetrate eukaryotic cells and its functional activity at the level of therapeutic gene mRNA expression and therapeutic protein. This example also demonstrates practicability of use of gene therapy DNA vector GDTT1.8NAS10.

For the validation of functional activity of DNA vector GDTT1.8NAS10 and practicability of its use, the therapeutic gene was cloned into a polylinker, e.g. the GBA gene listed in the GenBank database with number NM_000157. Obtaining of gene therapy DNA vector GDTT1.8NAS10-GBA carrying the therapeutic gene coding region, e.g. the GBA gene. The coding region of GBA gene was obtained by isolating total RNA from the biological human tissue sample followed by reverse transcription reaction using commercial kit Mint-2 (Evrogen, Russia) and PCR amplification using GBA_F and GBA_R oligonucleotides: (List of Sequences, (74) and (75)). The obtained PCR fragment was cleaved by EcoRV and EcoRI restriction endonucleases and ligated with a 3065 bp DNA vector carrying the kanamycin resistance gene and cleaved by the same enzymes. Further on, the kanamycin resistance gene was removed from the vector produced, as described in Example 1. This resulted in a 3617 bp DNA vector GDTT1.8NAS10-GBA allowing for antibiotic-free selection.

Changes in the mRNA accumulation of the GBA therapeutic gene were assessed in human peripheral blood macrophages SC (ATCC® CRL-9855™) before and 48 hours after their transfection with DNA vector GDTT1.8NAS10-GBA carrying the human GBA gene, and the quantitative content of the therapeutic GBA protein was compared after transfection of these cells with the gene therapy DNA vector GDTT1.8NAS10-GBA carrying the human GBA gene and DNA vector GDTT1.8NAS10 not carrying the human GBA gene.

SC cell culture was grown according to supplier recommendations (https://www.lgcstandards-atcc.org/Products/All/CRL-9855.aspx#culturemethod). The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS10-GBA expressing the human GBA gene was performed using Lipofectamine 3000 (ThermoFisher Scientific, USA) as described in Example 12. SC cells transfected with the gene therapy DNA vector GDTT1.8NAS10 devoid of the inserted therapeutic GBA gene (cDNA of GBA gene before and after transfection with gene therapy DNA vector GDTT1.8NAS10 devoid of the inserted therapeutic gene is not shown in the figures) were used as a reference. Reference vector GDTT1.8NAS10 for transfection was prepared as described above.

Total RNA from SC cells was extracted using Trizol Reagent (Invitrogen, USA) as described in Example 12. The level of GBA mRNA expression after transfection was determined by assessing the dynamics of the accumulation of cDNA amplicons by real-time PCR as described in Example 12. For the production and amplification of cDNA specific for the human GBA gene, the GBA_SF and GBA_SR oligonucleotides were used (list of sequences (76) and (77)). The length of amplification product is 397 bp.

Diagrams resulting from the assay are shown in FIG. 31.

The GBA protein was assayed by enzyme-linked immunosorbent assay (ELISA) using the ELISA Kit for Glucosidase Beta, Acid (GbA), Cloud-Clone Corp, USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of GBA protein was used. The sensitivity was at least 12.8 pg/ml, measurement range—from 31.2 pg/ml to 2000 pg/ml. R-3.0.2 was used for the statistical treatment of the results and data visualization (https://www.r-project.org/). Drawings resulting from the assay are shown in FIG. 32.

FIG. 31 shows that the level of specific mRNA of human GBA gene has grown massively as a result of transfection of human peripheral blood macrophages cell culture SC with gene therapy DNA vector GDTT1.8NAS10-GBA, which confirms the ability of the vector to penetrate eukaryotic cells and express the GBA gene at the mRNA level. FIG. 32 shows that the transfection of human peripheral blood macrophages cell culture SC with gene therapy DNA vector GDTT1.8NAS10-GBA results in increased GBA protein concentration compared to reference samples, which confirms the ability of the vector to penetrate eukaryotic cells and express the GBA gene at the mRNA level.

The presented results also confirm the practicability of use of gene therapy DNA vector GDTT1.8NAS10-GBA in order to increase the expression level of GBA gene in eukaryotic cells.

Example 22

Proof of the ability of gene therapy DNA vector GDTT1.8NAS11 to penetrate eukaryotic cells and its functional activity at the level of therapeutic gene mRNA expression and therapeutic protein. This example also demonstrates practicability of use of gene therapy DNA vector GDTT1.8NAS11.

For the validation of functional activity of DNA vector GDTT1.8NAS11 and practicability of its use, the therapeutic gene was cloned into a polylinker, e.g. the PDX1 gene listed in the GenBank database with number NM_000209. Obtaining of gene therapy DNA vector GDTT1.8NAS11-PDX1 carrying the therapeutic gene coding region, e.g. the PDX1 gene. The coding region of PDX1 gene was obtained by isolating total RNA from the biological human tissue sample followed by reverse transcription reaction using commercial kit Mint-2 (Evrogen, Russia) and PCR amplification using PDX1_F and PDX1_R oligonucleotides: (List of Sequences, (78) and (79)). The obtained PCR fragment was cleaved by BamHI and EcoRI restriction endonucleases and ligated with a 2995 bp DNA vector carrying the kanamycin resistance gene and cleaved by the same enzymes. Further on, the kanamycin resistance gene was removed from the vector produced, as described in Example 1. This resulted in a 2784 bp DNA vector GDTT1.8NAS11-PDX1 allowing for antibiotic-free selection.

Changes in the mRNA accumulation of the PDX1 therapeutic gene were assessed in pancreatic adenocarcinoma cells Panc 10.05 (ATCC® CRL-2547™) before and 48 hours after their transfection with DNA vector GDTT1.8NAS11-PDX1 carrying the human PDX1 gene, and the quantitative content of the therapeutic PDX1 protein was compared after transfection of these cells with the gene therapy DNA vector GDTT1.8NAS11-PDX1 carrying the human PDX1 gene and DNA vector GDTT1.8NAS11 not carrying the human PDX1 gene.

Panc 10.05 cell culture was grown under standard conditions (37° C., 5% CO2) using the ATCC-formulated RPMI-1640 Medium (ATCC) with the addition of 10 U/ml recombinant human insulin and 15% fetal bovine serum (Gibco). The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS11-PDX1 expressing the human PDX1 gene was performed using Lipofectamine 3000 (ThermoFisher Scientific, USA). Panc 10.05 cells transfected with the gene therapy DNA vector GDTT1.8NAS11 devoid of the inserted therapeutic PDX1 gene (cDNA of PDX1 gene before and after transfection with gene therapy DNA vector GDTT1.8NAS11 devoid of the inserted therapeutic gene is not shown in the figures) were used as a reference. Reference vector GDTT1.8NAS11 for transfection was prepared as described above.

Total RNA from Panc 10.05 cells was extracted using Trizol Reagent (Invitrogen, USA) as described in Example 12. The level of PDX1 mRNA expression after transfection was determined by assessing the dynamics of the accumulation of cDNA amplicons by real-time PCR as described in Example 12. For the production and amplification of cDNA specific for the human PDX1 gene, the PDX1_SF and PDX1_SR oligonucleotides were used (list of sequences (80) and (81)). The length of amplification product is 365 bp.

Diagrams resulting from the assay are shown in FIG. 33.

The PDX1 protein was assayed by enzyme-linked immunosorbent assay (ELISA) using Human PDX1 (Pancreas/duodenum homeobox protein 1) ELISA Kit, Wuhan Fine Biological Technology Co., Ltd., China according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of PDX1 protein was used. The sensitivity was at least 9.375 pg/ml, measurement range—from 15.6 pg/ml to 1000 pg/ml. R-3.0.2 was used for the statistical treatment of the results and data visualization (https://www.r-project.org/). Drawings resulting from the assay are shown in FIG. 34.

FIG. 33 shows that the level of specific mRNA of human PDX1 gene has grown massively as a result of transfection of pancreatic adenocarcinoma cell culture Panc 10.05 with gene therapy DNA vector GDTT1.8NAS11-PDX1, which confirms the ability of the vector to penetrate eukaryotic cells and express the PDX1 gene at the mRNA level. FIG. 34 shows that the transfection of pancreatic adenocarcinoma cell culture Panc 10.05 with gene therapy DNA vector GDTT1.8NAS11-PDX1 results in increased PDX1 protein concentration compared to reference samples, which confirms the ability of the vector to penetrate eukaryotic cells and express the PDX1 gene at the mRNA level.

The presented results also confirm the practicability of use of gene therapy DNA vector GDTT1.8NAS11-PDX1 in order to increase the expression level of PDX1 gene in eukaryotic cells.

Example 23

Proof of the ability of gene therapy DNA vector GDTT1.8NAS1 to penetrate eukaryotic cells and its functional activity at the level of therapeutic protein. This example also demonstrates practicability of use of gene therapy DNA vector GDTT1.8NAS1.

For the validation of functional activity of DNA vector GDTT1.8NAS1 and practicability of its use, the therapeutic gene was cloned into a polylinker, e.g. the VEGF gene listed in the GenBank database with number NM_001025368. Production of gene therapy DNA vector GDTT1.8NAS1-VEGF carrying the therapeutic gene coding region, e.g. the VEGF gene was performed as described in example 12.

To confirm the efficiency of gene therapy DNA vector GDTT1.8NAS1-VEGF carrying the therapeutic gene, namely the VEGF gene, and practicability of its use, changes in VEGF protein concentration in human muscle tissue upon injection of gene therapy DNA vector GDTT1.8NAS1-VEGF carrying the human VEGF gene into the muscle tissue were assessed.

To analyse changes in the concentration of VEGF protein, gene therapy DNA vector GDTT1.8NAS1-VEGF carrying the VEGF gene with transport molecule was injected into the gastrocnemius muscle of three patients with concurrent injection of a placebo being gene therapy DNA vector GDTT1.8NAS1 devoid of cDNA of VEGF gene with transport molecule.

Patient 1, man, 60 y.o. (P1); Patient 2, woman, 53 y.o. (P2); Patient 3, man, 49 y.o. (P3). Polyethyleneimine Transfection reagent cGMP grade in-vivo-jetPEI (Polyplus Transfection, France) was used as a transport system; sample preparation was carried out in accordance with the manufacturer's recommendations.

Gene therapy DNA vector GDTT1.8NAS1 (placebo) and gene therapy DNA vector GDTT1.8NAS1-VEGF carrying the VEGF gene were injected in the quantity of 1 mg for each genetic construct using the tunnel method with a 30 G needle to the depth of around 10 mm. The injectate volume of gene therapy DNA vector GDTT1.8NAS1 (placebo) and gene therapy DNA vector GDTT1.8NAS1-VEGF, carrying the VEGF gene was 0.3 ml for each genetic construct. The points of injection of each genetic construct were located medially at 8 to 10 cm intervals.

The biopsy samples were taken on the 2nd day after the injection of the genetic constructs of gene therapy DNA vectors. The biopsy samples were taken from the patients' muscle tissues in the site of injection of gene therapy DNA vector GDTT1.8NAS1-VEGF carrying the VEGF gene (I), gene therapy DNA vector GDTT1.8NAS1 (placebo) (II), and intact site of gastrocnemius muscle (III) using the skin biopsy device MAGNUM (BARD, USA). The skin of patients in the biopsy site was preliminarily rinsed with sterile saline and anaesthetised with a lidocaine solution. The biopsy sample size was ca. 10 mm3, and the weight was approximately 11 mg. The sample was placed in a buffer solution containing 50 mM of Tris-HCl, pH 7.6, 100 mM of NaCl, 1 mM of EDTA, and 1 mM of phenylmethylsulfonyl fluoride, and homogenised to obtain a homogenised suspension. The suspension was then centrifuged for 10 minutes at 14,000 g. Supernatant was collected and used to assay the therapeutic protein.

The VEGF protein was assayed by enzyme-linked immunosorbent assay (ELISA) using the ELISA Kit for Vascular Endothelial Growth Factor A (VEGFA), Cloud-Clone Corp., USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of VEGF protein was used. R-3.0.2 was used for the statistical treatment of the results and data visualization (https://www.r-project.org/). Drawings resulting from the assay are shown in FIG. 35.

FIG. 35 shows the increased VEGF protein concentration in the gastrocnemius muscle of all three patients in the injection site of gene therapy DNA vector GDTT1.8NAS1-VEGF carrying the therapeutic gene, namely human VEGF gene, compared to the VEGF protein concentration in the injection site of gene therapy DNA vector 8NAS1 (placebo) devoid of the human VEGF gene, which indicates the efficiency of gene therapy DNA vector GDTT1.8NAS1-VEGF and confirms the practicability of its use, in particular upon intramuscular injection of gene therapy DNA vector in human tissues.

Example 24

Proof of the ability of gene therapy DNA vector GDTT1.8NAS2 to penetrate eukaryotic cells and its functional activity at the level of therapeutic protein. This example also demonstrates practicability of use of gene therapy DNA vector GDTT1.8NAS2.

For the validation of functional activity of DNA vector GDTT1.8NAS2 and practicability of its use, the therapeutic gene was cloned into a polylinker, e.g. the CAT gene listed in the GenBank database with number NM_001752. Production of gene therapy DNA vector GDTT1.8NAS2-CAT carrying the therapeutic gene coding region, e.g. the CAT gene was performed as described in example 13. This resulted in a 3237 bp DNA vector GDTT1.8NAS2-CAT allowing for antibiotic-free selection.

To confirm the efficiency of gene therapy DNA vector GDTT1.8NAS2-CAT carrying the therapeutic gene, namely the CAT gene, and practicability of its use, changes in CAT protein concentration in human skin upon injection of gene therapy DNA vector GDTT1.8NAS2-CAT carrying the human CAT gene were assessed.

To analyse changes in the CAT protein concentration, gene therapy DNA vector GDTT1.8NAS2-CAT carrying the CAT gene was injected into the forearm skin of three patients with concurrent injection of a placebo being gene therapy DNA vector GDTT1.8NAS2-CAT devoid of cDNA of CAT gene.

Patient 1, woman, 38 y.o. (P1); Patient 2, woman, 66 y.o. (P2); Patient 3, man, 49 y.o. (P3). Polyethyleneimine Transfection reagent cGMP grade in-vivo-jetPEI (Polyplus Transfection, France) was used as a transport system. Gene therapy DNA vector GDTT1.8NAS2-CAT containing cDNA of CAT gene and gene therapy DNA vector GDTT1.8NAS2 used as a placebo not containing cDNA of CAT gene were dissolved in sterile nuclease-free water. To obtain a gene construct, DNA-cGMP grade in-vivo-jetPEI complexes were prepared according to the manufacturer recommendations.

Gene therapy DNA vector GDTT1.8NAS2 (placebo) and gene therapy DNA vector GDTT1.8NAS2-CAT carrying the CAT gene were injected in the quantity of 1 mg for each genetic construct using the tunnel method with a 30 G needle to the depth of 3 mm. The injectate volume of gene therapy DNA vector GDTT1.8NAS2 (placebo) and gene therapy DNA vector GDTT1.8NAS2-CAT, carrying the CAT gene was 0.3 ml for each genetic construct. The points of injection of each genetic construct were located at 8 to 10 cm intervals at the forearm site.

The biopsy samples were taken on the 2nd day after the injection of the genetic constructs of gene therapy DNA vectors. The biopsy samples were taken from the patients' skin in the site of injection of gene therapy DNA vector GGDTT1.8NAS2-CAT carrying the CAT gene (I), gene therapy DNA vector GDTT1.8NAS2 (placebo) (II), and from intact skin (III) using the skin biopsy device Epitheasy 3.5 (Medax SRL, Italy). The skin of patients in the biopsy site was preliminarily rinsed with sterile saline and anaesthetised with a lidocaine solution. The biopsy sample size was ca. 10 mm3, and the weight was approximately 11 mg. The sample was placed in a buffer solution containing 50 mM of Tris-HCl, pH 7.6, 100 mM of NaCl, 1 mM of EDTA, and 1 mM of phenylmethylsulfonyl fluoride, and homogenised to obtain a homogenised suspension. The suspension was then centrifuged for 10 minutes at 14,000 g. Supernatant was collected and used to assay the therapeutic protein by enzyme-linked immunosorbent assay (ELISA) using the ELISA Kit for Catalase (CAT) Cloud-Clone Corp. according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of CAT protein was used. R-3.0.2 was used for the statistical treatment of the results and data visualization (https://www.r-project.org/). Drawings resulting from the assay are shown in FIG. 36.

FIG. 36 shows the increased CAT protein concentration in the skin of all three patients in the injection site of gene therapy DNA vector GDTT1.8NAS2-CAT carrying the human CAT therapeutic gene compared to the CAT protein concentration in the injection site of gene therapy DNA vector GDTT1.8NAS2 (placebo) devoid of the human CAT gene, which indicates the efficiency of gene therapy DNA vector GDTT1.8NAS2-CAT and confirms the practicability of its use, in particular upon intracutaneous injection of gene therapy DNA vector in human tissues.

Example 25

Proof of the ability of gene therapy DNA vector GDTT1.8NAS7 to penetrate eukaryotic cells and its functional activity at the level of therapeutic gene mRNA expression and therapeutic protein. This example also demonstrates practicability of use of gene therapy DNA vector GDTT1.8NAS7 in animal cells.

For the validation of functional activity of DNA vector GDTT1.8NAS7 and practicability of its use, the therapeutic gene was cloned into a polylinker, e.g. the ATGL gene listed in the GenBank database with number NM_020376. Production of gene therapy DNA vector GDTT1.8NAS7-ATGL carrying the therapeutic gene coding region, e.g. the ATGL gene was performed as described in example 18. This resulted in a 4088 bp DNA vector GDTT1.8NAS7-ATGL allowing for antibiotic-free selection.

Changes in the mRNA accumulation of the ATGL therapeutic gene were assessed in primary bovine kidney cells MDBK (ATCC CLL-22) before and 48 hours after their transfection with DNA vector GDTT1.8NAS7-ATGL carrying the human ATGL gene, and the quantitative content of the therapeutic ATGL protein was compared after transfection of these cells with the gene therapy DNA vector GDTT1.8NAS7-ATGL carrying the human ATGL gene and DNA vector GDTT1.8NAS7 not carrying the human ATGL gene.

MDBK bovine kidney cell culture was grown in MEM medium (ThermoFisher Scientific, USA) containing 10% fetal bovine serum (ThermoFisher Scientific, USA), 1 g/l of glucose and 2 mM of glutamine with a 5% CO2 overlay at 37° C. The growth medium was replaced every 48 hours during the cultivation process.

To achieve 90% confluence, 24 hours before the transfection procedure, the cells were seeded into a 24-well plate in the quantity of 5×104 cells per well. Transfection with gene therapy DNA vector GDTT1.8NAS7-ATGL expressing the human ATGL gene was performed using Lipofectamine 3000 (ThermoFisher Scientific, USA) according to the manufacturer's recommendations. In test tube 1, 1 µl of DNA vector GDTT1.8NAS7-ATGL solution (concentration 500 ng/µl) and 1 µl of reagent P3000 was added to 25 µl of medium Opti-MEM (Gibco, USA). The preparation was mixed by gentle shaking. In test tube 2, 1 µl of Lipofectamine 3000 was added to 25 µl of medium Opti-MEM (Gibco, USA). The preparation was mixed by gentle shaking. The contents from test tube 1 were added to the contents of test tube 2, and the mixture was incubated at room temperature for 5 minutes. The resulting solution was added dropwise to the cells in the volume of 40 µl.

MDBK bovine kidney cells transfected with the gene therapy DNA vector GDTT1.8NAS7 devoid of the inserted therapeutic ATGL gene (cDNA of ATGL gene before and after transfection with gene therapy DNA vector GDTT1.8NAS7 devoid of the inserted therapeutic gene is not shown in the figures) were used as a reference. Reference vector GDTT1.8NAS7 for transfection was prepared as described above.

Total RNA from MDBK bovine kidney cells was extracted using Trizol Reagent (Invitrogen, USA) according to the manufacturer's recommendations. 1 ml of Trizol Reagent was added to the well with cells and homogenised and heated for 5 minutes at 65° C. Then the sample was centrifuged at 14,000 g for 10 minutes and heated again for 10 minutes at 65° C. Then 200 μl of chloroform was added, and the mixture was gently stirred and centrifuged at 14,000 g for 10 minutes. Then the water phase was isolated and mixed with ⅒ of the volume of 3M sodium acetate, pH 5.2, and an equal volume of isopropyl alcohol. The sample was incubated at −20° C. for 10 minutes and then centrifuged at 14,000 g for 10 minutes. The precipitated RNA was rinsed in 1 ml of 70% ethyl alcohol, air-dried and dissolved in 10 μl of RNase-free water. The level of ATGL mRNA expression after transfection was determined by assessing the dynamics of the accumulation of cDNA amplicons by real-time PCR. For the production and amplification of cDNA specific for the human ATGL gene, ATGL_SF and ATGL_SR oligonucleotides were used (list of sequences, (64) and (65)). The length of amplification product is 417 bp.

Reverse transcription reaction and PCR amplification was performed using SYBR GreenQuantitect RT-PCR Kit (Qiagen, USA) for real-time PCR. The reaction was carried out in a volume of 20 μl, containing: 25 μl of QuantiTect SYBR Green RT-PCR Master Mix, 2.5 mM of magnesium chloride, 0.5 μM of each primer, and 5 μl of RNA. For the reaction, CFX96 amplifier (Bio-Rad, USA) was used under the following conditions: 1 cycle of reverse transcription at 42° C. for 30 minutes, denaturation at 98° C. for 15 minutes, followed by 40 cycles comprising denaturation at 94° C. for 15 s, annealing of primers at 60° C. for 30 s and elongation at 72° C. for 30 s. bovine/cow actin gene listed in the GenBank database under the number AH001130.2 was used as a reference gene. Positive control included amplicons from PCR on matrices represented by plasmids in known concentrations containing cDNA sequences of ATGL and bovine ACT genes. Negative control included deionised water. Real-time quantification of the dynamics of accumulation of cDNA amplicons of ATGL and bovine ACT genes was conducted using the Bio-Rad CFX Manager 2.1 software (Bio-Rad, USA). Diagrams resulting from the assay are shown in FIG. 37.

The ATGL protein was assayed by enzyme-linked immunosorbent assay (ELISA) using the ELISA Kit for Patatin Like Phospholipase Domain Containing Protein 2 (PN-PLA2), Cloud-Clone Corp, USA according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of ATGL protein was used. R-3.0.2 was used for the statistical treatment of the results and data visualization (https://www.r-project.org/). Drawings resulting from the assay are shown in FIG. 38.

FIG. 37 shows that the level of specific mRNA of human ATGL gene has grown massively as a result of transfection of MDBK bovine kidney cell culture with gene therapy DNA vector GDTT1.8NAS7-ATGL, which confirms the ability of the vector to penetrate eukaryotic cells and express the ATGL gene at the mRNA level. FIG. 38 shows that the transfection of MDBK bovine kidney cell culture with gene therapy DNA vector GDTT1.8NAS7-ATGL results in increased ATGL protein concentration compared to reference samples, which confirms the ability of the vector to penetrate eukaryotic cells and express the ATGL gene at the protein level.

The presented results also confirm the practicability of use of gene therapy DNA vector GDTT1.8NAS7-ATGL in order to increase the expression level of ATGL gene in eukaryotic cells.

Example 26

Confirmation of functional activity at the level of therapeutic protein of the gene therapy DNA vector GDTT1.8NAS1 with the possibility of tissue-specific expression of therapeutic genes cloned into it mainly in muscle cells, gene therapy DNA vector GDTT1.8NAS2 with the possibility of tissue-specific expression of therapeutic genes cloned into it mainly in skin cells, gene therapy DNA vector GDTT1.8NAS3 with the possibility of tissue-specific expression of therapeutic genes cloned into it mainly in vascular endothelial cells, gene therapy DNA vector GDTT1.8NAS4, with the possibility of tissue-specific expression of therapeutic genes cloned into it mainly in osteoblasts and odontoblasts, gene therapy DNA vector GDTT1.8NAS5 with the possibility of tissue-specific expression of therapeutic genes cloned into it mainly in the epithelial cells of bronchi and alveoli, the gene therapy DNA vector GDTT1.8NAS6 with the possibility of tissue-specific expression of therapeutic genes cloned into it mainly in neurons, gene therapy DNA vector GDTT1.8NAS7 with the possibility of tissue-specific expression of therapeutic genes cloned into it mainly in kidney podocytes, gene therapy DNA vector GDTT1.8NAS8 with the possibility of tissue-specific expression of therapeutic genes cloned into it mainly in hematopoietic cells, GDTT1.8NAS9 gene therapy DNA vector with the possibility of tissue-specific expression of therapeutic genes cloned into it mainly in lymphocytes, gene therapy DNA vector GDTT1.8NAS10 with the possibility of tissue-specific expression of therapeutic genes cloned into it mainly in macrophages, gene therapy DNA vector GDTT1.8NAS11 with the possibility of tissue-specific expression of therapeutic genes cloned into it mainly in beta cells of pancreas, taking into account the tissue specificity of these gene therapy DNA vectors, i.e. the possibility to express the therapeutic genes cloned into it only in a specific target cell line, target tissue or human organ. This example also demonstrates practicability of use of gene therapy DNA vector GDTT1.8NAS1, GDTT1.8NAS2, GDTT1.8NAS3, GDTT1.8NAS4, GDTT1.8NAS5, GDTT1.8NAS6, GDTT1.8NAS7, GDTT1.8NAS8, GDTT1.8NAS9, GDTT1.8NAS10, GDTT1.8NAS11 for targeted gene therapy taking into account their tissue specificity.

For the validation of functional activity of DNA vectors GDTT1.8NAS1, GDTT1.8NAS2, GDTT1.8NAS3, GDTT1.8NAS4, GDTT1.8NAS5, GDTT1.8NAS6, GDTT1.8NAS7, GDTT1.8NAS8, GDTT1.8NAS9, GDTT1.8NAS10, GDTT1.8NAS11 and practicability of its use, the therapeutic gene was cloned into a polylinker of each gene therapy DNA vectors, e.g. the GFP gene.

Obtaining of gene therapy DNA vector GDTT1.8NAS1-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) using MVGFP-F and MVGFP-R oligonucleotides (List of Sequences, (82) and (83)). The obtained PCR fragment was cleaved by BamHI and EcoRI restriction endonucleases and ligated with a 2753 bp DNA vector carrying the kanamycin resistance gene and cleaved by the same enzymes. Further on, the kanamycin resistance gene was removed from the vector produced, as described in Example 1. This resulted in a 2413 bp DNA vector GDTT1.8NAS1-eGFP allowing for antibiotic-free selection.

Obtaining of gene therapy DNA vector GDTT1.8NAS2-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) as described above. The obtained PCR fragment was cleaved by BamHI and EcoRI restriction endonucleases and ligated with a 2671 bp DNA vector carrying the kanamycin resistance gene and cleaved by the same enzymes. Further on, the kanamycin resistance gene was removed from the vector produced, as described in Example 1. This resulted in a 2331 bp DNA vector GDTT1.8NAS2-eGFP allowing for antibiotic-free selection.

Obtaining of gene therapy DNA vector GDTT1.8NAS3-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) as described above. The obtained PCR fragment was cleaved by BamHI and EcoRI restriction endonucleases and ligated with a 2800 bp DNA vector carrying the kanamycin resistance gene and cleaved by the same enzymes. Further on, the kanamycin resistance gene was removed from the vector produced, as described in Example 1. This resulted in a 2460 bp DNA vector GDTT1.8NAS3-eGFP allowing for antibiotic-free selection.

Obtaining of gene therapy DNA vector GDTT1.8NAS4-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) as described above. The obtained PCR fragment was cleaved by BamHI and EcoRI restriction endonucleases and ligated with a 2970 bp DNA vector carrying the kanamycin resistance gene and cleaved by the same enzymes. Further on, the kanamycin resistance gene was removed from the vector produced, as described in Example 1. This resulted in a 2630 bp DNA vector GDTT1.8NAS4-eGFP allowing for antibiotic-free selection.

Obtaining of gene therapy DNA vector GDTT1.8NAS5-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) as described above. The obtained PCR fragment was cleaved by BamHI and EcoRI restriction endonucleases and ligated with a 3036 bp DNA vector carrying the kanamycin resistance gene and cleaved by the same enzymes. Further on, the kanamycin resistance gene was removed from the vector produced, as described in Example 1. This resulted in a 2696 bp DNA vector GDTT1.8NAS5-eGFP allowing for antibiotic-free selection.

Obtaining of gene therapy DNA vector GDTT1.8NAS6-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) as described above. The obtained PCR fragment was cleaved by BamHI and EcoRI restriction endonucleases and ligated with a 2957 bp DNA vector carrying the kanamycin resistance gene and cleaved by the same enzymes. Further on, the kanamycin resistance gene was removed from the vector produced, as described in Example 1. This resulted in a 2617 bp DNA vector GDTT1.8NAS6-eGFP allowing for antibiotic-free selection.

Obtaining of gene therapy DNA vector GDTT1.8NAS7-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) as described above. The obtained PCR fragment was cleaved by BamHI and EcoRI restriction endonucleases and ligated with a 3637 bp DNA vector carrying the kanamycin resistance gene and cleaved by the same enzymes. Further on, the kanamycin resistance gene was removed from the vector produced, as described in Example 1. This resulted in a 3297 bp DNA vector GDTT1.8NAS7-eGFP allowing for antibiotic-free selection.

Obtaining of gene therapy DNA vector GDTT1.8NAS8-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) as described above. The obtained PCR fragment was cleaved by BamHI and EcoRI restriction endonucleases and ligated with a 3257 bp DNA vector carrying the kanamycin resistance gene and cleaved by the same enzymes. Further on, the kanamycin resistance gene was removed from the vector produced, as described in Example 1. This resulted in a 2917 bp DNA vector GDTT1.8NAS8-eGFP allowing for antibiotic-free selection.

Obtaining of gene therapy DNA vector GDTT1.8NAS9-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) as described above. The obtained PCR fragment was cleaved by BamHI and EcoRI restriction endonucleases and ligated with a 3621 bp DNA vector carrying the kanamycin resistance gene and cleaved by the same enzymes. Further on, the kanamycin resistance gene was removed from the vector produced, as described in Example 1. This resulted in a 3281 bp DNA vector GDTT1.8NAS9-eGFP allowing for antibiotic-free selection.

Obtaining of gene therapy DNA vector GDTT1.8NAS10-eGFP carrying the therapeutic gene, e.g. the gene coding green fluorescent protein (GFP).

The coding region of the green fluorescent protein gene was produced by PCR amplification of commercially available plasmid pEGFP-N1 (Clontech) as described above. The obtained PCR fragment was cleaved by BamHI and EcoRI restriction endonucleases and ligated with a 3065 bp DNA vector carrying the kanamycin resistance gene and cleaved by the same restriction endonucleases BglII and EcoRI. Further on, the kanamycin resistance gene was removed from the vector produced, as described in Example 1. This resulted in a 2719 bp DNA vector GDTT1.8NAS10-eGFP allowing for antibiotic-free selection.

Obtaining of gene therapy DNA vector GDTT1.8NAS11-eGFP carrying the therapeutic gene, e.g. the gene coding green fluorescent protein (GFP).

The coding region of the green fluorescent protein gene was produced by PCR amplification of commercially available plasmid pEGFP-N1 as described above. The obtained PCR fragment was cleaved by BamHI and EcoRI restriction endonucleases and ligated with a 2995 bp DNA vector carrying the kanamycin resistance gene and cleaved by the same enzymes. Further on, the kanamycin resistance gene was removed from the vector produced, as described in Example 1. This resulted in a 2655 bp DNA vector GDTT1.8NAS11-eGFP allowing for antibiotic-free selection.

Comparison of levels of accumulation of a therapeutic gene, e.g. the green fluorescent protein (GFP) in each cell line: in primary human skeletal myoblast cell culture HSkM (ThermoFisher Scientific #A12555), in primary human dermal fibroblast cell culture HDFa (ATCC® PCS-201-012™), in primary umbilical vein endothelial cell culture HUVEC (ATCC® PCS-100-013™), in human osteosarcoma cells MG-63 (ATCC® CRL-1427™), in human tracheal epithelial cell line CFTE29o- (Collection of Institute of Cytology RAS RF), in human neuroblastoma cell culture SH-SY5Y (ATCC® CRL-2266™), in primary human kidney epithelial mixed cell culture HREC (ATCC® PCS-400-012™), in human primary bone marrow cell culture (ATCC® PCS-800-012™), in primary human peripheral blood mononuclear cell culture PBMC (ATCC® PCS-800-011™), in human peripheral blood macrophages SC (ATCC® CRL-9855™), in pancreatic adenocarcinoma cells Panc 10.05 (ATCC® CRL-2547™) 48 hours after their transfection with each gene therapy DNA vector: gene therapy DNA vector GDTT1.8NAS1-eGFP, gene therapy DNA vector GDTT1.8NAS2-eGFP, gene therapy DNA vector GDTT1.8NAS3-eGFP, gene therapy DNA vector GDTT1.8NAS4-eGFP, gene therapy DNA vector GDTT1.8NAS5-eGFP, gene therapy DNA vector GDTT1.8NAS6-eGFP, gene therapy DNA vector GDTT1.8NAS7-eGFP, gene therapy DNA vector GDTT1.8NAS8-eGFP, gene therapy DNA vector GDTT1.8NAS9-eGFP, gene therapy DNA vector GDTT1.8NAS10eGFP, gene therapy DNA vector GDTT1.8NAS11-eGFP.

To quantify the level of accumulation of the green fluorescent protein in primary human skeletal myoblast cell culture HSkM, in primary human dermal fibroblast cell culture HDFa, in primary umbilical vein endothelial cell culture HUVEC, in human osteosarcoma cells MG-63, in human tracheal epithelial cell line CFTE29o-, in human neuroblastoma cell culture SH-SY5Y, in primary human kidney epithelial mixed cell culture HREC, in human primary bone marrow cell culture, in primary human peripheral blood mononuclear cell culture PBMC, in human peripheral blood macrophages SC, in pancreatic adenocarcinoma cells Panc 10.05 each cell line was transfected with each gene therapy DNA vector: gene therapy DNA vector GDTT1.8NAS1-eGFP, gene therapy DNA vector GDTT1.8NAS2-eGFP, gene therapy DNA vector GDTT1.8NAS3-eGFP, gene therapy DNA vector GDTT1.8NAS4-eGFP, gene therapy DNA vector GDTT1.8NAS5-eGFP, gene therapy DNA vector GDTT1.8NAS6-eGFP, gene therapy DNA vector GDTT1.8NAS7-eGFP, gene therapy DNA vector GDTT1.8NAS8-eGFP, gene therapy DNA vector GDTT1.8NAS9-eGFP, gene therapy DNA vector GDTT1.8NAS10eGFP, gene therapy DNA vector GDTT1.8NAS11-eGFP. A similar transfection of these cell lines with plasmid vector pEFGP-N1 (Clontech) was made as a reference. Primary human skeletal myoblast cell culture HSkM, primary human dermal fibroblast cell culture HDFa, primary umbilical vein endothelial cell culture HUVEC, human osteosarcoma cells MG-63, human tracheal epithelial cell line CFTE29o-, human neuroblastoma cell culture SH-SY5Y, primary human kidney epithelial mixed cell culture HREC, human primary bone marrow cell culture, primary human peripheral blood mononuclear cell culture PBMC, human peripheral blood macrophages SC, pancreatic adenocarcinoma cells Panc 10.05 were grown as described in examples 12, 13, 14, 15, 16, 17, 18, 19, 20, 21, 22. To achieve 90% confluence, 24 hours before the transfection procedure, the each line cells were seeded into a 24-well plate in the quantity of 4×104 cells per well. Lipofectamine 3000 (ThermoFisher Scientific, USA) was used as a transfection reagent for each cell line. For transfection of each cell line with each gene therapy DNA vector in each test tube No. 1, 1 µl of each gene therapy DNA vector solution: gene therapy DNA vector GDTT1.8NAS2-eGFP, gene therapy DNA vector GDTT1.8NAS3-eGFP, gene therapy DNA vector GDTT1.8NAS4-eGFP, gene therapy DNA vector GDTT1.8NAS5-eGFP, gene therapy DNA vector GDTT1.8NAS6-eGFP, gene therapy DNA vector GDTT1.8NAS7-eGFP, gene therapy DNA vector GDTT1.8NAS8-eGFP, gene therapy DNA vector GDTT1.8NAS9-eGFP, gene therapy DNA vector GDTT1.8NAS10eGFP, gene therapy DNA vector GDTT1.8NAS11-eGFP (concentration of each is 500 ng/µl) and 1 µl of reagent P3000 were added to 25 µl of medium Opti-MEM (Gibco). The preparation was mixed by gentle shaking. In each test tube 2, 1 µl of solution Lipofectamine 3000 was added to 25 µl of medium Opti-MEM (Gibco). The preparation was mixed by gentle shaking. The contents from each test tube 1 were added to the contents of relevant test tube 2, and the mixture was incubated at room temperature for 5 minutes. The resulting solution was added dropwise to the each cell line in the volume of 40 µl.

The results were recorded by measuring fluorescence of the protein extracted from the each transfected cell line. For this purpose, the cells of each transfected line were rinsed from the well by pipetting and pelleted at 6000 rpm for 10 minutes, rinsed twice, and then the packed cells were re-suspended in 1 ml of sodium phosphate buffer. The cells were lysed in three freeze/thaw cycles at −70° C. Then the homogenate of lysed cells was pelleted at 13,000 g for 15 minutes. Supernatants were transferred into a 96-well culture plate (Grainer Bio-one) in four replicates for each sample, and then relative fluorescence of GFP was measured (absorption 455 nm/emission 538 nm) using Fluoroskan Ascent Microplate Fluorometer (Labsystems). The resulting values were normalised according to the total protein concentration in the sample that was measured by the Bradford protein assay. For this purpose, Coomassie Brilliant Blue R-250 (BioRad) was used as a dye. Each replicate was diluted in the wells of the 96-well plate (4 replicates for each sample) with water by a factor of 100, and then the dye was added. After that, optical density of all samples was measured at 620 nm using Multiskan Ascent (Thermo). The resulting values were compared with the calibration curve constructed for bovine serum albumin (Bio-Rad) with a series of sequential dilutions from 20 to 2.5 µg/ml. Calculations were made using the following formula:

$$\Sigma\text{protein amount (µg)} = \{[x] - \sigma\} \div k \ast M,$$

where [x] is the mean value of OD620 of the four replicates for each sample, σ—average deviation, k is the slope coefficient of the calibration curve for BSA, M is the dilution factor of the sample.

Based on the values of the total concentration of protein extracted from the cells, GFP fluorescence in the samples was normalized using the following formula:

$$OEn = [OE] \div \Sigma\text{protein amount (µg)}$$

Where

[OE] is the average of the four replicates for each sample, in relative fluorescence units.

The table below shows the level of fluorescence (in relative fluorescence units) of the isolated total protein from each cell line: from primary human skeletal myoblast cell culture HSkM, from primary human dermal fibroblast cell culture HDFa, from primary umbilical vein endothelial cell culture HUVEC, from human osteosarcoma cells MG-63, from human tracheal epithelial cell line CFTE29o-, from human neuroblastoma cell culture SH-SY5Y, primary human kidney epithelial mixed cell culture HREC, from human primary bone marrow cell culture, from primary human peripheral blood mononuclear cell culture PBMC, from human peripheral blood macrophages SC, from pancreatic adenocarcinoma cells Panc 10.05 48 hours after transfection of each of them with each gene therapy DNA vector: gene therapy DNA vector GDTT1.8NAS1-eGFP, gene therapy DNA vector GDTT1.8NAS2-eGFP, gene therapy DNA vector GDTT1.8NAS3-eGFP, gene therapy DNA vector GDTT1.8NAS4-eGFP, gene therapy DNA vector GDTT1.8NAS5-eGFP, gene therapy DNA vector GDTT1.8NAS6-eGFP, gene therapy DNA vector GDTT1.8NAS7-eGFP, gene therapy DNA vector GDTT1.8NAS8-eGFP, gene therapy DNA vector GDTT1.8NAS9-eGFP, gene therapy DNA vector GDTT1.8NAS10eGFP, gene therapy DNA vector GDTT1.8NAS11-eGFP for the purpose of comparing the levels of accumulation of the product of the target gene, e.g. green fluorescent protein (GFP), in each cell line: in primary human skeletal myoblast cell culture HSkM, in primary human dermal fibroblast cell culture HDFa, in primary umbilical vein endothelial cell culture HUVEC, in human osteosarcoma cells MG-63, in human tracheal epithelial cell line CFTE29o-, in human neuroblastoma cell culture SH-SY5Y, in primary human kidney epithelial mixed cell culture HREC, in human primary bone marrow cell culture, in primary human peripheral blood mononuclear cell culture PBMC, in human peripheral blood macrophages SC, in pancreatic adenocarcinoma cells Panc 10.05 48 hours after transfection of each of them with each gene therapy DNA vector: gene therapy DNA vector GDTT1.8NAS1-eGFP, gene therapy DNA vector GDTT1.8NAS2-eGFP, gene therapy DNA vector GDTT1.8NAS3-eGFP, gene therapy DNA vector GDTT1.8NAS4-eGFP, gene therapy DNA vector GDTT1.8NAS5-eGFP, gene therapy DNA vector GDTT1.8NAS6-eGFP, gene therapy DNA vector GDTT1.8NAS7-eGFP, gene therapy DNA vector GDTT1.8NAS8-eGFP, gene therapy DNA vector GDTT1.8NAS9-eGFP, gene therapy DNA vector GDTT1.8NAS10eGFP, gene therapy DNA vector GDTT1.8NAS11-eGFP in order to assess tissue specificity of these gene therapy DNA vectors.

TABLE

| Cell Line | DNA Vector | | | | | | | | | | |
|---|---|---|---|---|---|---|---|---|---|---|---|
| | GDTISNAS1-eGFP | GDTISNAS2-eGFP | GDTISNAS3-eGFP | GDTISNAS4-eGFP | GDTISNAS5-eGFP | GDTISNAS6-eGFP | GDTISNAS7-eGFP | GDTISNAS8-eGFP | GDTISNAS9-eGFP | GDTISNAS10-eGFP | GDTISNAS11-eGFP |
| HSkM human primary skeletal myoblast cell culture | 0.986 | 0.023 | 0.285 | 0.112 | 0.201 | 0.087 | 0.101 | 0.2 | 0.123 | 0.034 | 0.111 |
| HDFa human primary dermal fibroblast cells | 0.231 | 0.879 | 0.012 | 0.087 | 0.094 | 0.111 | 0.092 | 0.012 | 0.094 | 0.156 | 0.059 |
| HUVEC human umbilical vein endothelial cells | 0.124 | 0.125 | 0.923 | 0.071 | 0.165 | 0.04 | 0.218 | 0.077 | 0.011 | 0.182 | 0.117 |
| MG-63 human osteosarcoma cells | 0.235 | 0.086 | 0.049 | 0.889 | 0.112 | 0.023 | 0.151 | 0.098 | 0.114 | 0.061 | 0.042 |
| CFTE29o- human tracheal epithelial cells | 0.134 | 0.019 | 0.149 | 0.129 | 0.945 | 0.043 | 0.055 | 0.113 | 0.098 | 0.115 | 0.062 |
| SH-SY5Y human neuroblastoma cell culture | 0.198 | 0.239 | 0.217 | 0.02 | 0.092 | 0.934 | 0.178 | 0.129 | 0.086 | 0.097 | 0.103 |
| HREC primary human kidney epithelial mixed cell culture | 0.096 | 0.147 | 0.098 | 0.198 | 0.122 | 0.118 | 0.973 | 0.093 | 0.101 | 0.085 | 0.117 |
| Primary human bone | 0.144 | 0.234 | 0.087 | 0.116 | 0.198 | 0.076 | 0.082 | 0.911 | 0.065 | 0.102 | 0.096 |

TABLE-continued

DNA Vector

| Cell Line | GDTISNAS1-eGFP | GDTISNAS2-eGFP | GDTISNAS3-eGFP | GDTISNAS4-eGFP | GDTISNAS5-eGFP | GDTISNAS6-eGFP | GDTISNAS7-eGFP | GDTISNAS8-eGFP | GDTISNAS9-eGFP | GDTISNAS10-eGFP | GDTISNAS11-eGFP |
|---|---|---|---|---|---|---|---|---|---|---|---|
| marrow cell culture |  |  |  |  |  |  |  |  |  |  |  |
| PBMC human blood mononuclear cells | 0.029 | 0.087 | 0.034 | 0.076 | 0.054 | 0.065 | 0.066 | 0.055 | 0.901 | 0.064 | 0.084 |
| SC human peripheral blood macrophages | 0.091 | 0.023 | 0.231 | 0.091 | 0.023 | 0.075 | 0.021 | 0.043 | 0.058 | 0.878 | 0.081 |
| Panc 10.05 | 0.034 | 0.011 | 0.097 | 0.132 | 0.022 | 0.0112 | 0.011 | 0.099 | 0.057 | 0.063 | 0.845 |
| HSkM pancreatic adenocarcinoma cell culture |  |  |  |  |  |  |  |  |  |  |  |

The table shows that transfection of HSkM human skeletal muscle myoblast cells with the gene therapy DNA vector GDTT1.8NAS1-eGFP with the possibility of tissue-specific expression of the therapeutic genes cloned into it in muscle tissue cells, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in muscle tissue cells; Transfection of primary human dermal fibroblast cell culture HDFa with the gene therapy DNA vector GDTT1.8NAS2-eGFP with the possibility of tissue-specific expression of the therapeutic genes cloned into it in skin cells, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in skin cells; Transfection of human umbilical vein endothelial cells HUVEC with the gene therapy DNA vector GDTT1.8NAS3-eGFP with the possibility of tissue-specific expression of the therapeutic genes cloned into it in vascular endothelial cells, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in vascular endothelial cells; Transfection of human osteosarcoma cells MG-63 with the gene therapy DNA vector GDTT1.8NAS4-eGFP with the possibility of tissue-specific expression of the therapeutic genes cloned into it in osteoblasts and odontoblasts, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in osteoblasts and odontoblasts; Transfection of human tracheal epithelial cells CFTE29o- with the gene therapy DNA vector GDTT1.8NAS5-eGFP with the possibility of tissue-specific expression of the therapeutic genes cloned into it in bronchi and alveoli epithelial cells, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in bronchi and alveoli epithelial cells; Transfection of primary human neuroblastoma cell culture SH-SY5Y with the gene therapy DNA vector GDTT1.8NAS6-eGFP with the possibility of tissue-specific expression of the therapeutic genes cloned into it in neurons, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in neurons; Transfection of primary human kidney epithelial mixed cell culture HREC with the gene therapy DNA vector GDTT1.8NAS7-eGFP with the possibility of tissue-specific expression of the therapeutic genes cloned into it in renal podocytes, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in renal podocytes; Transfection of primary human bone marrow cell culture with the gene therapy DNA vector GDTT1.8NAS8-eGFP with the possibility of tissue-specific expression of the therapeutic genes cloned into it in hematopoietic cells, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in hematopoietic cells; Transfection of primary human peripheral blood mononuclear cell culture PBMC with the gene therapy DNA vector GDTT1.8NAS9-eGFP with the possibility of tissue-specific expression of the therapeutic genes cloned into it in lymphocytes, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in lymphocytes; Transfection of human peripheral blood macrophages SC with the gene therapy DNA vector GDTT1.8NAS10-eGFP with the possibility of tissue-specific expression of the therapeutic genes cloned into it in macrophages, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in macrophages; Transfection of pancreatic adenocarcinoma cells Panc 10.05 with the gene therapy DNA vector GDTT1.8NAS11-eGFP, with the possibility of tissue-specific expression of the therapeutic genes cloned into it in beta cells of pancreas, leads to a reliable increase in the accumulation of green fluorescent protein in comparison with the accumulation of green fluorescent protein upon transfection of these cells with other gene therapy DNA vectors without possibility of tissue-specific expression of therapeutic genes cloned into it in beta cells of pancreas;

Example 26 results confirm the ability of gene therapy DNA vectors: gene therapy DNA vector GDTT1.8NAS1-eGFP, gene therapy DNA vector GDTT1.8NAS2-eGFP, gene therapy DNA vector GDTT1.8NAS3-eGFP, gene therapy DNA vector GDTT1.8NAS4-eGFP, gene therapy DNA vector GDTT1.8NAS5-eGFP, gene therapy DNA vector GDTT1.8NAS6-eGFP, gene therapy DNA vector GDTT1.8NAS7-eGFP, gene therapy DNA vector GDTT1.8NAS8-eGFP, gene therapy DNA vector GDTT1.8NAS9-eGFP, gene therapy DNA vector GDTT1.8NAS10eGFP, gene therapy DNA vector GDTT1.8NAS11-eGFP to penetrate into eukaryotic cells, their functional activity, as well as tissue specificity of these gene therapy DNA vectors through the possibility of reliable increase in the level of expression of the therapeutic gene cloned into these vectors in a specific cell line, tissue or human organ.

The presented results confirm the practicability of selection of gene therapy DNA vector for the construction of gene therapy DNA vector containing the therapeutic gene for targeted gene therapy.

Example 27

Obtaining of *Escherichia coli* strain JM-110-NAS for production of gene therapy DNA vector GDTT1.8NAS1 or GDTT1.8NAS2 or GDTT1.8NAS3 or GDTT1.8NAS4 or GDTT1.8NAS5 or GDTT1.8NAS6$_{HJH}$ GDTT1.8NAS7 or GDTT1.8NAS8 or GDTT1.8NAS9 or GDTT1.8NAS10 or GDTT1.8NAS11 and/or gene therapy DNA vectors carrying therapeutic genes based on it.

*Escherichia coli* strain JM-110-NAS for the production of gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11 and/or gene therapy vectors carrying therapeutic genes based on it as produced by homologous recombination by introduction to its chromosome, specifically to the region of recA gene, of the linear fragment containing regulatory element RNA-in of transposon Tn10 allowing for antibiotic-free positive selection (110 bp), levansucrase gene sacB, the product of which ensures selection in a sucrose-containing medium (64 bp), chloramphenicol resistance gene catR required for selection of strain clones in which homologous recombination occurred (1422 bp), and two homologous sequences (homology arms) ensuring homologous recombination in the region of gene recA concurrent with gene inactivation (329 bp and 233 bp for the left arm and for the right arm, respectively).

To obtain the left and the right homology arms, fragments of gene recA were amplified by PCR using the genomic DNA of *Escherichia coli* JM110 (Agilent Technologies, cat. No. 200239) as a matrix. To obtain the left homology arm, LHA-F and LHA-R primers (List of Sequences, (84) and (85)) were used, while for obtaining the right homology arm, RHA-F and RHA-R primers (List of Sequences, (86) and (87)) were used. The RNA-in fragment was tailed with IN-F, IN-1, IN-2, and IN-R synthetic oligonucleotides (List of Sequences, (88), (89), (90), (91)). The sacB gene was produced by PCR amplification using the genomic DNA of *B. subtilis* 168HT as a matrix, and SacB-F and SacB-R as primers (List of Sequences, (92) and (93)). To obtain the catR gene, PCR amplification was performed using *Escherichia coli* BL21 pLysS as a matrix, and CatR-F and CatR-R (List of Sequences, (94) and (95)) as primers. PCR products LHA (the left homology arm), SacB, and RHA (the right homology arm) were amplified at 94° C. for 3 minutes; 30 cycles: at 94° C. for 20 seconds, at 60° C. for 20 seconds, and at 72° C. for 60 seconds, with final elongation at 72° C. for 5 minutes. PCR product RNA-IN was obtained at 94° C. for 3 minutes; 30 cycles: at 94° C. for 10 seconds, at 60° C. for 10 seconds, and at 72° C. for 10 seconds, using oligonucleotides IN-F, IN-1, IN-2 and IN-R (List of Sequences, (88), (89), (90), and (91)) for the assembly of the fragment. For this, 10 µM of primers IN-F and IN-R, and 5 µM of primers IN-1 and IN-2 were used. PCR amplification was performed using the commercially available kit Phusion® High-Fidelity DNA Polymerase (Thermo Fisher Scientific) as per the manufacturer's instructions.

The linear fragment for homologous recombination was obtained by consolidating five PCR products. All of the five products had overlapping areas allowing for subsequent assembly into a single fragment. All fragments were mixed in aliquots of 10 ng in a volume of 50 µl. The PCR product was derived at 94 C for 3 minutes; 10 cycles: at 94° C. for 30 seconds, at 60° C. for 30 seconds, and at 72° C. for 2 minutes, without primers added. Then LHA-F and RHA-R primers (List of Sequences, (84), (85)) were added, and 25 more PCR cycles were performed: at 94° C. for 30 seconds, at 60° C. for 30 seconds, and at 72° C. for 2 minutes, with final elongation at 72° C. for 5 minutes. This resulted in a 2811 bp long PCR fragment having the following structure: LHA-RNA-IN-SacB-CatR-RHA. This fragment was recovered preparatively from agarose gel using the DNA Elution Kit (BioSilica, Russia) according to the manufacturer's instructions. The structure of the DNA fragment for homologous recombination in the region of recA gene of *Escherichia coli* for obtaining *Escherichia coli* strain JM 110 is shown in FIG. 12.

To obtain *Escherichia coli* strain JM110-NAS, electrocompetent cells were prepared. For this purpose, a single colony of *Escherichia coli* strain JM 110 (Agilent Technologies) was used to inoculate 10 ml of LB broth, and the cells were cultured overnight in an orbital shaker at 150 rpm and 37° C. On the following day, ¹/₂₀ was re-plated into 100 ml of LB broth and cultured in an orbital shaker at 150 rpm and 37° C. to reach OD600=0.5. Upon reaching the required optical density, the cells were cooled down to 0° C. and centrifuged for 10 minutes at 4000 g. Then the medium was removed and the cells were rinsed with 100 ml of ice-cold bidistilled water twice to remove the remaining medium and then rinsed with 20 ml of 10% glycerine. After that, the cells were re-suspended in 1 ml of 10% glycerine and used for transformation.

Transformation with the produced linear fragment was performed by electroporation in 1 mm cuvettes at 2 kV, 200 Ohm, 25 µF using the Gene Pulser Xcell (Bio-Rad, USA). The duration of the pulse was 4.9 ms to 5.1 ms. After that, the cells were cultivated in a SOC medium for 2.5 hours in an incubator shaker at 30° C. Then the cells were poured into LB agar plates (Petri dishes) containing 10 µg/ml of chloramphenicol. The cells were cultivated for 48 hours at 30° C. The picked-out clones were tested for survival in a selective medium containing yeastrel, peptone, 6% sucrose, and 10 µg/ml of chloramphenicol. The genotype of the resulting strain is recA rpsL (Strr) thr leu endA thi-1 lacY galK gaiT ara tonA tsx dam dcm supE44 Δ(lac-proAB) [F' traD36 proAB lacIq ZΔM15]CmR sacB+

Example 28

Obtaining of *Escherichia coli* strain JM-110-NAS-GDTT1.8NAS1 carrying gene therapy DNA vector GDTT1.8NAS1 and/or gene therapy DNA vectors containing therapeutic genes based on it for production thereof.

To prepare electrocompetent cells of *Escherichia coli* strain JM110-NAS, a single colony was used to infect 10 ml of LB broth, and the cells were cultured overnight in an orbital shaker at 150 rpm and 37° C. On the following day, ¹/₂₀ was re-plated into 100 ml of LB broth and cultured in an orbital shaker at 150 rpm and 37° C. to reach OD600=0.5. Upon reaching the required optical density, the cells were cooled down to 0° C. and centrifuged for 10 minutes at 4000 g. Then the medium was removed and the cells were rinsed with 100 ml of ice-cold bidistilled water twice to remove the remaining medium and then rinsed with 20 ml of 10% glycerine. After that, the cells were re-suspended in 1 ml of 10% glycerine and used for transformation by electroporation of gene therapy DNA vector GDTT1.8NAS1. Electroporation was performed in 1 mm cuvettes at 2 kV, 200 Ohm, 25 µF using the Gene Pulser Xcell (Bio-Rad, USA). The duration of the pulse was 4.9 to 5.1 ms, and 1-10 ng of the vector was used. After that, the cells were cultivated in a SOC medium for 2.5 hours in an incubator shaker at 30° C. Then the cells were poured into agar plates (Petri dishes) with a selective medium containing yeastrel, peptone, 6% sucrose, and 10 µg/ml of chloramphenicol. Thus, *Escherichia coli* strain JM110-NAS/GDTT1.8NAS1 carrying gene therapy DNA vector GDTT1.8NAS1 was obtained. 48 hours later, a single colony was used to inoculate 10 ml of liquid selective medium containing yeastrel, peptone, 6% sucrose, and 10 µg/ml of chloramphenicol, and the medium was cultivated overnight in an orbital shaker at 150 rpm and 37° C. On the following day, the cells were pelleted, and DNA vector was extracted by alkaline lysis using GeneJET Plasmid Miniprep Kit (Thermo Fisher Scientific) according to the manufacturer's instructions.

*Escherichia coli* strain JM110-NAS/GDTT1.8NAS1 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13223, date of deposit 21 Aug. 2018; accession No. NCIMB 43108, date of deposit 19 Jul. 2018).

Example 29

Obtaining of *Escherichia coli* strain JM-110-NAS-GDTT1.8NAS2 carrying gene therapy DNA vector GDTT1.8NAS2 and/or gene therapy DNA vectors containing therapeutic genes based on it for production thereof.

*Escherichia coli* strain JM110-NAS/GDTT1.8NAS2 carrying the gene therapy DNA vector GDTT1.8NAS2 was obtained according to example 28 differing by the fact that transformation of the electrocompetent cells of *Escherichia coli* strain JM110-NAS by electroporation was performed with gene therapy DNA vector GDTT1.8NAS2

*Escherichia coli* strain JM110-NAS/GDTT1.8NAS2 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13224, date of deposit 21 Aug. 2018; accession No. NCIMB 43109, date of deposit 19 Jul. 2018).

Example 30

Obtaining of *Escherichia coli* strain JM-110-NAS-GDTT1.8NAS3 carrying gene therapy DNA vector GDTT1.8NAS3 and/or gene therapy DNA vectors containing therapeutic genes based on it for production thereof.

*Escherichia coli* strain JM110-NAS/GDTT1.8NAS3 carrying the gene therapy DNA vector GDTT1.8NAS3 was obtained according to example 28 differing by the fact that transformation of the electrocompetent cells of *Escherichia coli* strain JM110-NAS by electroporation was performed with gene therapy DNA vector GDTT1.8NAS3.

*Escherichia coli* strain JM110-NAS/GDTT1.8NAS3 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13225, date of deposit 21 Aug. 2018; accession No. NCIMB 43110, date of deposit 19 Jul. 2018).

Example 31

Obtaining of *Escherichia coli* strain JM-110-NAS-GDTT1.8NAS4 carrying gene therapy DNA vector GDTT1.8NAS4 and/or gene therapy DNA vectors containing therapeutic genes based on it for production thereof.

*Escherichia coli* strain JM110-NAS/GDTT1.8NAS4 carrying the gene therapy DNA vector GDTT1.8NAS4 was obtained according to example 28 differing by the fact that transformation of the electrocompetent cells of *Escherichia coli* strain JM110-NAS by electroporation was performed with gene therapy DNA vector GDTT1.8NAS4.

*Escherichia coli* strain JM110-NAS/GDTT1.8NAS4 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13226, date of deposit 21 Aug. 2018; accession No. NCIMB 43111, date of deposit 19 Jul. 2018).

Example 32

Obtaining of *Escherichia coli* strain JM-110-NAS-GDTT1.8NAS5 carrying gene therapy DNA vector GDTT1.8NAS5 and/or gene therapy DNA vectors containing therapeutic genes based on it for production thereof.

*Escherichia coli* strain JM110-NAS/GDTT1.8NAS5 carrying the gene therapy DNA vector GDTT1.8NAS5 was obtained according to example 28 differing by the fact that transformation of the electrocompetent cells of *Escherichia coli* strain JM110-NAS by electroporation was performed with gene therapy DNA vector GDTT1.8NAS5.

*Escherichia coli* strain JM110-NAS/GDTT1.8NAS5 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13227, date of deposit 21 Aug. 2018; accession No. NCIMB 43112, date of deposit 19 Jul. 2018).

Example 33

Obtaining of *Escherichia coli* strain JM-110-NAS-GDTT1.8NAS6 carrying gene therapy DNA vector GDTT1.8NAS6 and/or gene therapy DNA vectors containing therapeutic genes based on it for production thereof.

*Escherichia coli* strain JM110-NAS/GDTT1.8NAS6 carrying the gene therapy DNA vector GDTT1.8NAS6 was obtained according to example 28 differing by the fact that transformation of the electrocompetent cells of *Escherichia coli* strain JM110-NAS by electroporation was performed with gene therapy DNA vector GDTT1.8NAS6.

*Escherichia coli* strain JM110-NAS/GDTT1.8NAS6 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13228, date of deposit 21 Aug. 2018; accession No. NCIMB 43113, date of deposit 19 Jul. 2018).

Example 34

Obtaining of *Escherichia coli* strain JM-110-NAS-GDTT1.8NAS7 carrying gene therapy DNA vector GDTT1.8NAS7 and/or gene therapy DNA vectors containing therapeutic genes based on it for production thereof.

*Escherichia coli* strain JM110-NAS/GDTT1.8NAS7 carrying the gene therapy DNA vector GDTT1.8NAS7 was obtained according to example 28 differing by the fact that transformation of the electrocompetent cells of *Escherichia coli* strain JM110-NAS by electroporation was performed with gene therapy DNA vector GDTT1.8NAS7.

*Escherichia coli* strain JM110-NAS/GDTT1.8NAS7 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13229, date of deposit 21 Aug. 2018; accession No. NCIMB 43114, date of deposit 19 Jul. 2018).

Example 35

Obtaining of *Escherichia coli* strain JM-110-NAS-GDTT1.8NAS8 carrying gene therapy DNA vector GDTT1.8NAS8 and/or gene therapy DNA vectors containing therapeutic genes based on it for production thereof.

*Escherichia coli* strain JM110-NAS/GDTT1.8NAS8 carrying the gene therapy DNA vector GDTT1.8NAS8 was obtained according to example 28 differing by the fact that transformation of the electrocompetent cells of *Escherichia coli* strain JM110-NAS by electroporation was performed with gene therapy DNA vector GDTT1.8NAS8.

*Escherichia coli* strain JM110-NAS/GDT1.8NAS8 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13230, date of deposit 21 Aug. 2018; accession No. NCIMB 43115, date of deposit 19 Jul. 2018).

Example 36

Obtaining of *Escherichia coli* strain JM-110-NAS-GDTT1.8NAS9 carrying gene therapy DNA vector GDTT1.8NAS9 and/or gene therapy DNA vectors containing therapeutic genes based on it for production thereof.

*Escherichia coli* strain JM110-NAS/GDTT1.8NAS9 carrying the gene therapy DNA vector GDTT1.8NAS9 was obtained according to example 28 differing by the fact that transformation of the electrocompetent cells of *Escherichia coli* strain JM110-NAS by electroporation was performed with gene therapy DNA vector GDTT1.8NAS9.

*Escherichia coli* strain JM110-NAS/GDTT1.8NAS9 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13231, date of deposit 21 Aug. 2018; accession No. NCIMB 43116, date of deposit 19 Jul. 2018).

Example 37

Obtaining of *Escherichia coli* strain JM-110-NAS-GDTT1.8NAS10 carrying gene therapy DNA vector GDTT1.8NAS10 and/or gene therapy DNA vectors containing therapeutic genes based on it for production thereof.

*Escherichia coli* strain JM110-NAS/GDTT1.8NAS10 carrying the gene therapy DNA vector GDTT1.8NAS10 was obtained according to example 28 differing by the fact that transformation of the electrocompetent cells of *Escherichia coli* strain JM110-NAS by electroporation was performed with gene therapy DNA vector GDTT1.8NAS10.

*Escherichia coli* strain JM110-NAS/GDTT1.8NAS10 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13232, date of deposit 21 Aug. 2018; accession No. NCIMB 43117, date of deposit 19 Jul. 2018).

Example 38

Obtaining of *Escherichia coli* strain JM-110-NAS-GDTT1.8NAS11 carrying gene therapy DNA vector GDTT1.8NAS11 and/or gene therapy DNA vectors containing therapeutic genes based on it for production thereof.

*Escherichia coli* strain JM110-NAS/GDTT1.8NAS11 carrying the gene therapy DNA vector GDTT1.8NAS11 was obtained according to example 28 differing by the fact that transformation of the electrocompetent cells of *Escherichia coli* strain JM110-NAS by electroporation was performed with gene therapy DNA vector GDTT1.8NAS11.

*Escherichia coli* strain JM110-NAS/GDTT1.8NAS11 was deposited in the collection of the National Biological Resource Centre—Russian National Collection of Industrial Microorganisms (NBRC RNCIM) RF and INTERNATIONAL DEPOSITARY AUTHORITY NCIMB Patent Deposit Service, UK (registration number VKPM-B-13233, date of deposit 21 Aug. 2018; accession No. NCIMB 43118, date of deposit 19 Jul. 2018).

Example 39

A method of production on an industrial scale of gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11 and/or gene therapy DNA vectors carrying therapeutic genes based on it.

To confirm the producibility and constructability on an industrial scale of gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11 and/or gene therapy DNA vectors carrying therapeutic genes based on it, a large-scale fermentation of *Escherichia coli* strain JM-110-NAS-GDTT1.8NAS1 or *Escherichia coli* strain JM-110-NAS-GDTT1. or *Escherichia coli* strain JM-110-NAS-GDTT1.8NAS3 or *Escherichia coli* strain JM-110-NAS-GDTT1.8NAS4 or *Escherichia coli* strain JM-110-NAS-GDTT1.8NAS5 or *Escherichia coli* strain JM-110-NAS-GDTT1.8NAS6 or *Escherichia coli* strain JM-110-NAS-GDTT1.8NAS7 or *Escherichia coli* strain JM-110-NAS-GDTT1.8NAS8 or *Escherichia coli* strain JM-110-NAS-GDTT1.8NAS9 or *Escherichia coli* strain JM-110-NAS-GDTT1.8NAS10 or *Escherichia coli* strain JM-110-NAS-GDTT1.8NAS11, each carries the gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11.

Each *Escherichia coli* strain JM-110-NAS-GDTT1.8NAS1 or *Escherichia coli* strain JM-110-NAS-GDTT1.8NAS2 or *Escherichia coli* strain JM-110-NAS-GDTT1.8NAS3 or *Escherichia coli* strain JM-110-NAS-GDTT1.8NAS4 or *Escherichia coli* strain JM-110-NAS-GDTT1.8NAS5 or *Escherichia coli* strain JM-110-NAS-GDTT1.8NAS6 or *Escherichia coli* strain JM-110-NAS-GDTT1.8NAS7 or *Escherichia coli* strain JM-110-NAS-GDTT1.8NAS8 or *Escherichia coli* strain JM-110-NAS-GDTT1.8NAS9 or *Escherichia coli* strain JM-110-NAS-GDTT1.8NAS10 or *Escherichia coli* strain JM-110-NAS- GDTT1.8NAS11 was obtained according to Example 28 or 29 or 30 or 31 or 32 or 33 or 34 or 35 or 36 or 37 or 38.

Fermentation of *Escherichia coli* strain JM110-NAS/GDTT1.8NAS1 carrying gene therapy DNA vector GDTT1.8NAS1 was performed in a 10 l fermenter with subsequent extraction of gene therapy DNA vector GDTT1.8NAS1.

For the fermentation of *Escherichia coli* strain JM110-NAS/GDTT1.8NAS1, a medium was prepared containing per 10 l: 100 g of tryptone, 50 g of yeastrel (Becton Dickinson), then the medium was diluted with water to 8800 ml and autoclaved at 121° C. for 20 minutes, and then 1,200 ml of 50% (w/v) sucrose was added. After that, the seed culture of *Escherichia coli* strain JM110-NAS/GDTT1.8NAS1 was inoculated into a culture flask in the volume of 100 ml. The culture was incubated in an incubator shaker for 16 hours at 30° C. The seed culture was transferred to the Techfors S bioreactor (Infors HT, Switzerland) and grown to a stationary phase. The process was controlled by measuring optical density of the culture at 600 nm. The cells were pelleted for 30 minutes at 5,000-10,000 g. Supernatant was removed, and the cell pellet was re-suspended in 10% (by volume) phosphate buffered saline. The cells were centrifuged again for 30 minutes at 5,000-10,000 g. Supernatant was removed, a solution of 20 mM TrisCl, 1 mM EDTA, 200 g/l sucrose, pH 8.0 was added to the cell pellet in the volume of 1000 ml, and the mixture was stirred thoroughly to a homogenised suspension. Then egg lysozyme solution was added to the final concentration of 100 µg/ml. The mixture was incubated for 20 minutes on ice while stirring gently. Then 2500 ml of 0.2M NaOH, 10 g/l sodium dodecyl sulphate (SDS) was added, the mixture was incubated for 10 minutes on ice while stirring gently, then 3500 ml of 3M sodium acetate, 2M acetic acid, pH 5-5.5 was added, and the mixture was incubated for 10 minutes on ice while stirring gently. The resulting sample was centrifuged for 20-30 minutes at 15,000 g or a greater value. The solution was decanted delicately, and residual precipitate was removed by passing through a coarse filter (filter paper). Then RNase A (Sigma) was added to the final concentration of 20 µg/ml, and the solution was incubated overnight for 16 hours at room temperature. The solution was then centrifuged for 20-30 minutes at 15,000 g and passed through a 0.45 µm membrane filter (Millipore). Then ultrafiltration was performed with a membrane of 100 kDa (Millipore) and the mixture was diluted to the initial volume with a buffer solution of 25 mM TrisCl, pH 7.0. This manipulation was performed three to four times. The solution was applied to the column with 250 ml of DEAE Sepharose HP (GE, USA), equilibrated with 25 mM TrisCl, pH 7.0. After the application of the sample, the column was washed with three volumes of the same solution, and then gene therapy DNA vector GDTT1-8NAS1 was eluted using a linear gradient of 25 mM Tris-HCl, pH 7.0, to obtain a solution of 25 mM Tris-HCl, pH 7.0, 1M NaCl, five times the volume of the column. The elution process was controlled by measuring optical density of the run-off solution at 260 nm. Chromatographic fractions containing gene therapy DNA vector GDTT1.8NAS1 were joined together and subjected to gel filtration by Superdex 200 sorbent (GE, USA). The column was equilibrated with phosphate buffered saline. The elution process was controlled by measuring optical density of the run-off solution at 260 nm, and the fractions were analysed by agarose gel electrophoresis. The fractions containing gene therapy DNA vector GDTT1.8NAS1 were joined together and stored at −20° C. To assess the process reproducibility, the indicated processing operations were repeated four times. The yield of final product was sufficient for large-scale industrial production of gene therapy DNA vector GDTT1.8NAS1.

All processing operations for *Escherichia coli* strain JM-110-NAS-GDTT1.8NAS2 or *Escherichia coli* JM-110-NAS-GDTT1.8NAS3 or *Escherichia coli* JM-110-NAS-GDTT1.8NAS4 or *Escherichia coli* JM-110-NAS-GDTT1.8NAS5 or *Escherichia coli* JM-110-NAS-GDTT1.8NAS6 or *Escherichia coli* JM-110-NAS-GDTT1.8NAS7 or *Escherichia coli* JM-110-NAS-GDTT1.8NAS8 or *Escherichia coli* JM-110-NAS-GDTT1.8NAS9 or *Escherichia coli* JM-110-NAS-GDTT1.8NAS10 or *Escherichia coli* JM-110-NAS-GDTT1.8NAS11 were performed in a similar way. The process reproducibility and quantitative characteristics of final product yield confirm the producibility and constructability of gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11 on an industrial scale and/or gene therapy DNA vectors carrying therapeutic genes based on it.

Produced gene therapy DNA vector containing the therapeutic genes can be used to deliver it to the cells of human beings and animals that experience reduced or insufficient expression of that gene, thus ensuring the desired therapeutic effect, as well as the possibility of editing the sequence of the human genome. The tissue specificity of the therapeutic gene expression is determined by the presence of special regulatory elements in the gene therapy DNA vector.

Therefore, the purpose of this invention, specifically the construction of a gene therapy DNA vector for genetic modification of human and animal cells, which would reasonably combine:

I) possibility of safe use in the gene therapy of human beings and animals due to the absence of antibiotic resistance genes in the gene therapy DNA vector, II) length that ensures efficient gene delivery to the target cell;

III) presence of regulatory elements that ensure efficient expression of the therapeutic genes while not being represented by nucleotide sequences of viral genomes;

IV) possibility of choosing the gene therapy DNA vector for targeted gene therapy from a group of gene therapy DNA vectors carrying different promoter and regulatory regions to construct a gene therapy DNA vector containing a target gene based on criteria of its tissue-specific expression and maximum efficiency in the target cell line, target tissue or organ of the human body.

V) constructability and producibility on an industrial scale, as well as the purpose of construction of strains carrying these gene therapy DNA vectors for the production of these gene therapy DNA vectors on an industrial scale has been achieved, which is supported by the following examples: for Item I—Example 1, 2, 3, 4, 5; 6, 7, 8, 9, 10, 11, 12, 13, 14, 15, 16, 17, 18, 19, 20, 21, 22, 23, 24, 25, 26; for Item II—Examples 1, 2, 3, 4, 5; 6, 7, 8, 9, 10, 11, 12, 13, 14, 15, 16, 17, 18, 19, 20, 21, 22, 23, 24, 25, 26; for Item III—Example 1, 2, 3, 4, 5; 6, 7, 8, 9, 10, 11, 12, 13, 14, 15, 16, 17, 18, 19, 20, 21, 22, 23, 24, 25, 26; for Item V—Example 12, 13, 14, 15, 16, 17, 18, 19, 20, 21, 22, 23, 24, 25, 26; for Item V—Example 27, 28, 29, 30, 31, 32, 33, 34, 35, 36, 37, 38, 39.

INDUSTRIAL APPLICABILITY

All the examples listed above confirm industrial applicability of the proposed gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11, method of its production, *Escherichia coli* strain JM-110-NAS, method of its production, *Escherichia coli* strain JM-110-NAS-GDTT1.8NAS1 or *Escherichia coli* JM-110-NAS-GDTT1.8NAS2 or *Escherichia coli* strain JM-110-NAS-GDTT1.8NAS3 or *Escherichia coli* strain JM-110-NAS-GDTT1.8NAS4 or *Escherichia coli* strain JM-110-NAS-GDTT1.8NAS5 or *Escherichia coli* strain JM-110-NAS-GDTT1.8NAS6 or *Escherichia coli* strain JM-110-NAS-GDTT1.8NAS7 or *Escherichia coli* strain JM-110-NAS-GDTT1.8NAS8 or *Escherichia coli* strain JM-110-NAS-GDTT1.8NAS9 or *Escherichia coli* strain JM-110-NAS-GDTT1.8NAS10 or *Escherichia coli* strain JM-110-NAS-GDTT1.8NAS11 carrying gene therapy DNA vector GDTT1.8NAS1 or GDTT1.8NAS2 or GDTT1.8NAS3 or GDTT1.8NAS4 or GDTT1.8NAS5 or GDTT1.8NAS6 or GDTT1.8NAS7 or GDTT1.8NAS8 or GDTT1.8NAS9 or GDTT1.8NAS10 or GDTT1.8NAS11, method of its production, method of gene therapy DNA vector production on an industrial scale.

LIST OF ABBREVIATIONS

GDTT1.8NAS_—Gene therapy vector devoid of sequences of viral genomes and antibiotic resistance markers (GDT—manufacturer abbreviation, T—vector therapeutic, 1.8—reference length, NA—no antibiotic)
DNA—Deoxyribonucleic acid
cDNA—Complementary deoxyribonucleic acid
RNA—Ribonucleic acid
mRNA—Messenger ribonucleic acid
bp—base pair
PCR—Polymerase chain reaction
ml—millilitre, µl—microliter
l—litre
µg—microgram
mg—milligram
g—gram
µM—micromol
mM—millimol
min—minute
s—second
rpm—rotations per minute
nm—nanometre
cm—centimetre
mW—milliwatt
RFU—Relative fluorescence unit
PBS—Phosphate buffered saline

What is claimed is:

1. A gene therapy DNA vector selected from the group consisting of GDTT1.8NAS1, GDTT1.8NAS2, GDTT1.8NAS3, GDTT1.8NAS4, GDTT1.8NAS5, GDTT1.8NAS6, GDTT1.8NAS7, GDTT1.8NAS8, GDTT1.8NAS9, GDTT1.8NAS10 and GDTT1.8NAS11 for targeted gene therapy aimed at increasing an expression level of a therapeutic gene in target human tissue cells, wherein the gene therapy DNA vector GDTT1.8NAS1 has a nucleotide sequence SEQ ID No. 1, the gene therapy DNA vector GDTT1.8NAS2 has a nucleotide sequence SEQ ID No. 2, the gene therapy DNA vector GDTT1.8NAS3 has a nucleotide sequence SEQ ID No. 3, the gene therapy DNA vector GDTT1.8NAS4 has a nucleotide sequence SEQ ID No. 4, the gene therapy DNA vector GDTT1.8NAS5 has a nucleotide sequence SEQ ID No. 5, the gene therapy DNA vector GDTT1.8NAS6 has a nucleotide sequence SEQ ID No. 6, the gene therapy DNA vector GDTT1.8NAS7 has a nucleotide sequence SEQ ID No. 7, the gene therapy DNA vector GDTT1.8NAS8 has a nucleotide sequence SEQ ID No. 8, the gene therapy DNA vector GDTT1.8NAS9 has a nucleotide sequence SEQ ID No. 9, the gene therapy DNA vector GDTT1.8NAS10 has a nucleotide sequence SEQ ID No. 10, the gene therapy DNA vector GDTT1.8NAS11 has a nucleotide sequence SEQ ID No. 11, and has an ability to efficiently penetrate into target human and animal tissue cells and express the therapeutic gene cloned to it.

* * * * *

```
                        SEQUENCE LISTING

<160> NUMBER OF SEQ ID NOS: 106

<210> SEQ ID NO 1
<211> LENGTH: 1736
<212> TYPE: DNA
<213> ORGANISM: Homo Sapiens

<400> SEQUENCE: 1
ataacgcagg aaagaacatg tgagcaaaag gccagcaaaa ggccagggac cgtaaaaagg      60
ccgcgttgct ggcgtttttc cataggctcc gcccccctga cgagcatcac aaaaatcgac     120
gctcaagtca gaggtggcga acccgacag gactataaag ataccaggcg tttccccctg      180
gaagctccct cgtgcgctct cctgttccga ccctgccgct taccggatac ctgtccgcct     240
ttctcccttc gggaagcgtg gcgctttctc atagctcacg ctgtaggtat ctcagttcgg     300
tgtaggtcgt tcgctccaag ctgggctgtg tgcacgaacc cccgttcag cccgaccgct      360 gcgccttatc cggtaactat cgtcttgagt ccaacccggt aagacacgac ttatcgccac     420
tggcagcagc cactggtaac aggattagca gagcgaggta tgtaggcggt gctacagagt     480
tcttgaagtg gtggcctaac tacggctaca ctagaagaac agtatttggt atctgcgctc     540
tgctgaagcc agttaccttc ggaaaaagag ttggtagctc ttgatccggc aaacaaacca     600
ccgctggtag cggtggtttt tttgtttgca agcagcagat tacgcgcaga aaaaaaggat     660
ctcaagaaga tcctttgatc ttttctacct cgaggtggcc aagcttagaa acatgacagg     720
tcctcttggg agggctgacc gcaggagcg ttgggtttca ggctgctggc gtcggcttct      780
gtggtgccct ttctgtcggc tatgagagtc cagacagtgc ccaacctcct ccccttcttt     840
ccacacgcac aaccacccca ccccctgtgg cctgagctgt cctgcctcgc cacaatggca     900
cctgccctaa aatagcttcc catgtgaggg ctagagaaag gaaagattaa gaccctccct     960
ggatgagaga gagaaagtga aggagggcag gggaggggga cagcgagcca ttgagcgatc    1020
tttgtcaagc atcccagaag gtataaggat ccgatatcgt cgacaagctt ggtacctccg    1080
```

-continued

| | |
|---|---|
| gagcggccgc tctagagcta gcgacgtcga attccctgtg acccctcccc agtgcctctc | 1140 |
| ctggccctgg aagttgccac tccagtgccc accagccttg tcctaataaa attaagttgc | 1200 |
| atcattttgt ctgactaggt gtccttctat aatattatgg ggtggagggg ggtggtatgg | 1260 |
| agcaaggggc aagttgggaa gacaacctgt agggcctgcg gggtctattg gaaccaagc | 1320 |
| tggagtgcag tggcacaatc ttggctcact gcaatctccg cctcctgggt tcaagcgatt | 1380 |
| ctcctgcctc agcctcccga gttgttggga ttccaggcat gcatgaccag gctcagctaa | 1440 |
| ttttttgtttt tttggtagag acggggtttc accatattgg ccaggctggt ctccaactcc | 1500 |
| taatctcagg tgatctaccc accttggcct cccaaattgc tgggattaca ggcgtgaacc | 1560 |
| actgctccct tccctgtcct tacgcgtaga attggtaaag agagtcgtgt aaaatatcga | 1620 |
| gttcgcacat cttgttgtct gattattgat ttttggcgaa accatttgat catatgacaa | 1680 |
| gatgtgtatc taccttaact taatgatttt gataaaaatc attaactagt ccatgg | 1736 |

<210> SEQ ID NO 2
<211> LENGTH: 1654
<212> TYPE: DNA
<213> ORGANISM: Homo Sapiens

<400> SEQUENCE: 2

| | |
|---|---|
| ataacgcagg aaagaacatg tgagcaaaag gccagcaaaa ggccagggac cgtaaaaagg | 60 |
| ccgcgttgct ggcgtttttc cataggctcc gccccctga cgagcatcac aaaaatcgac | 120 |
| gctcaagtca gaggtggcga aacccgacag gactataaag ataccaggcg tttccccctg | 180 |
| gaagctccct cgtgcgctct cctgttccga ccctgccgct taccggatac ctgtccgcct | 240 |
| ttctcccttc gggaagcgtg gcgctttctc atagctcacg ctgtaggtat ctcagttcgg | 300 |
| tgtaggtcgt tcgctccaag ctgggctgtg tgcacgaacc ccccgttcag cccgaccgct | 360 |
| gcgccttatc cggtaactat cgtcttgagt ccaacccggt aagacacgac ttatcgccac | 420 |
| tggcagcagc cactggtaac aggattagca gagcgaggta tgtaggcggt gctacagagt | 480 |
| tcttgaagtg gtggcctaac tacggctaca ctagaagaac agtatttggt atctgcgctc | 540 |
| tgctgaagcc agttaccttc ggaaaaagag ttggtagctc ttgatccggc aaacaaacca | 600 |
| ccgctggtag cggtggtttt tttgtttgca agcagcagat tacgcgcaga aaaaaggat | 660 |
| ctcaagaaga tcctttgatc ttttctacct cgagcatctt atttctgaaa agagtttgt | 720 |
| tgatgctttt tcaattaaaa gcagatgatt aattcagccc tggccttgtt ctgtctttga | 780 |
| ataacagata cattagttta cttgaaaaga aatattttca tttgtatttc catgtcactt | 840 |
| gtgattttcc ctgccttgca ccctcagccc tgccagttgg caagaagaca gtcagctttg | 900 |
| ctgctaagag gagtataaag agggcttggt ccaagcaaga aggcagtggt ctactccatc | 960 |
| ggcaggatcc gatatcgtcg acaagcttgg tacctccgga gcggccgctc tagagctagc | 1020 |
| gacgtcgaat tccctgtgac ccctcccag tgcctctcct ggccctggaa gttgccactc | 1080 |
| cagtgcccac cagccttgtc ctaataaaat taagttgcat cattttgtct gactaggtgt | 1140 |
| ccttctataa tattatgggg tggagggggg tggtatggag caaggggcaa gttgggaaga | 1200 |
| caacctgtag ggcctgcggg gtctattggg aaccaagctg gagtgcagtg gcacaatctt | 1260 |
| ggctcactgc aatctccgcc tcctgggttc aagcgattct cctgcctcag cctcccgagt | 1320 |
| tgttgggatt ccaggcatgc atgaccaggc tcagctaatt ttgttttttt tggtagagac | 1380 |
| ggggtttcac catattggcc aggctggtct ccaactccta atctcaggtg atctacccac | 1440 |

```
cttggcctcc caaattgctg ggattacagg cgtgaaccac tgctcccttc cctgtcctta    1500
cgcgtagaat tggtaaagag agtcgtgtaa aatatcgagt tcgcacatct tgttgtctga    1560
ttattgattt ttggcgaaac catttgatca tatgacaaga tgtgtatcta ccttaactta    1620
atgattttga taaaaatcat taactagtcc atgg                                1654

<210> SEQ ID NO 3
<211> LENGTH: 1783
<212> TYPE: DNA
<213> ORGANISM: Homo Sapiens

<400> SEQUENCE: 3
ataacgcagg aaagaacatg tgagcaaaag gccagcaaaa ggccagggac cgtaaaaagg     60
ccgcgttgct ggcgtttttc cataggctcc gcccccctga cgagcatcac aaaaatcgac    120
gctcaagtca gaggtggcga aacccgacag gactataaag ataccaggcg tttccccctg    180
gaagctccct cgtgcgctct cctgttccga ccctgccgct taccggatac ctgtccgcct    240
ttctcccttc gggaagcgtg cgctttctc atagctcacg ctgtaggtat ctcagttcgg    300
tgtaggtcgt tcgctccaag ctgggctgtg tgcacgaacc cccgttcag cccgaccgct    360 gcgccttatc cggtaactat cgtcttgagt ccaacccggt aagacacgac ttatcgccac    420
tggcagcagc cactggtaac aggattagca gagcgaggta tgtaggcggt gctacagagt    480
tcttgaagtg gtggcctaac tacggctaca ctagaagaac agtatttggt atctgcgctc    540
tgctgaagcc agttaccttc ggaaaaagag ttggtagctc ttgatccggc aaacaaacca    600
ccgctggtag cggtggtttt tttgtttgca agcagcagat tacgcgcaga aaaaaggat    660 ctcaagaaga tcctttgatc ttttctacct cgaggtctcc caggcatgac tccaacaatg    720
catcccatgg gatttgggt tccccagatc tggggcttgt aggcctgact ctcccctgtg    780
cacacgtctc atacacgcat gcgtgcaccc attgcctgcc ccgccccttg cacagggagt    840
cagcagggag gactgggtta tgccctgctt atcagcagct cccagcttc ctctgcctgg    900 attcttagag gcctggggtc ctagaacgag ctggtgcacg tggcttccca agatctctc    960 agataatgag aggaaatgca gtcatcagtt tgcagaaggc tagggattct gggccatagc   1020
tcagacctgc gcccaccatc tccctccagg cagcccttgg ctggtccctg cgagcccgtg   1080
gagactgcca gtcggatccg atatcgtcga caagcttggt acctccggag cggccgctct   1140
agagctagcg acgtcgaatt ccctgtgacc cctccccagt gcctctcctg gcctggaag    1200 ttgccactcc agtgcccacc agccttgtcc taataaaatt aagttgcatc attttgtctg   1260
actaggtgtc cttctataat attatggggt ggagggggt ggtatggagc aaggggcaag    1320
ttgggaagac aacctgtagg gcctgcgggg tctattggga accaagctgg agtgcagtgg   1380
cacaatcttg gctcactgca atctccgcct cctgggttca agcgattctc ctgcctcagc   1440
ctcccgagtt gttgggattc caggcatgca tgaccaggct cagctaattt tgtttttttt   1500
ggtagagacg gggtttcacc atattggcca ggctggtctc caactcctaa tctcaggtga   1560
tctacccacc ttggcctccc aaattgctgg gattacaggc gtgaaccact gctcccttcc   1620
ctgtccttac gcgtagaatt ggtaaagaga gtcgtgtaaa atatcgagtt cgcacatctt   1680
gttgtctgat tattgatttt tggcgaaacc atttgatcat atgacaagat gtgtatctac   1740
cttaacttaa tgattttgat aaaaatcatt aactagtcca tgg                    1783

<210> SEQ ID NO 4
<211> LENGTH: 1953
```

```
<212> TYPE: DNA
<213> ORGANISM: Homo Sapiens

<400> SEQUENCE: 4
ataacgcagg aaagaacatg tgagcaaaag gccagcaaaa ggccagggac cgtaaaaagg      60
ccgcgttgct ggcgtttttc cataggctcc gccccctga cgagcatcac aaaaatcgac     120
gctcaagtca gaggtggcga acccgacag gactataaag ataccaggcg tttccccctg     180
gaagctccct cgtgcgctct cctgttccga ccctgccgct taccggatac ctgtccgcct     240
ttctcccttc gggaagcgtg gcgctttctc atagctcacg ctgtaggtat ctcagttcgg     300
tgtaggtcgt tcgctccaag ctgggctgtg tgcacgaacc cccgttcag cccgaccgct     360
gcgccttatc cggtaactat cgtcttgagt ccaacccggt aagacacgac ttatcgccac     420
tggcagcagc cactggtaac aggattagca gagcgaggta tgtaggcggt gctacagagt     480
tcttgaagtg gtggcctaac tacggctaca ctagaagaac agtatttggt atctgcgctc     540
tgctgaagcc agttaccttc ggaaaaagag ttggtagctc ttgatccggc aaacaaacca     600
ccgctggtag cggtggtttt tttgtttgca agcagcagat tacgcgcaga aaaaaggat     660
ctcaagaaga tcctttgatc ttttctacct cgagcaccca cagcaggctg cctttggtga     720
ctcaccgggt gaacggggggc attgcgaggc atcccctccc tgggtttggc tcctgcccac     780
ggggctgaca gtagaaatca caggctgtga cacagctgga gcccagctct gcttgaacct     840
attttaggtc tctgatcccc gcttcctctt tagactcccc tagagctcag ccagtgctca     900
acctgaggct gggggtctct gaggaagagt gagttggagc tgaggggtct ggggctgtcc     960
cctgagagag gggccagagg cagtgtcaag agccgggcag tctgattgtg gctcaccctc    1020
catcactccc aggggcccct ggcccagcag ccgcagctcc caaccacaat atcctttggg    1080
gtttggccta cggagctggg gcggatgacc cccaaatagc cctggcagat tcccctaga    1140
cccgcccgca ccatggtcag gcatgcccct cctcatcgct gggcacagcc cagagggtat    1200
aaacagtgct ggaggctggc ggggcaggcc agctgagtcc tgagcagcag cccagcgcag    1260
ccaggatccg atatcgtcga caagcttggt acctccggag cggccgctct agagctagcg    1320
acgtcgaatt ccctgtgacc cctccccagt gcctctcctg gccctggaag ttgccactcc    1380
agtgcccacc agccttgtcc taataaaatt aagttgcatc attttgtctg actaggtgtc    1440
cttctataat attatggggt ggagggggt ggtatgagc aagggcaag ttgggaagac    1500
aacctgtagg gcctgcgggg tctattggga accaagctgg agtgcagtgg cacaatcttg    1560
gctcactgca atctccgcct cctgggttca agcgattctc ctgcctcagc ctcccgagtt    1620
gttgggattc caggcatgca tgaccaggct cagctaattt ttgttttttt ggtagagacg    1680
gggtttcacc atattggcca ggctggtctc caactcctaa tctcaggtga tctacccacc    1740
ttggcctccc aaattgctgg gattacaggc gtgaaccact gctcccttcc ctgtccttac    1800
gcgtagaatt ggtaaagaga gtcgtgtaaa atatcgagtt cgcacatctt gttgtctgat    1860
tattgatttt tggcgaaacc atttgatcat atgacaagat gtgtatctac cttaacttaa    1920
tgattttgat aaaaatcatt aactagtcca tgg                                 1953

<210> SEQ ID NO 5
<211> LENGTH: 2019
<212> TYPE: DNA
<213> ORGANISM: Homo Sapiens

<400> SEQUENCE: 5
```

```
ataacgcagg aaagaacatg tgagcaaaag gccagcaaaa ggccagggac cgtaaaaagg    60
ccgcgttgct ggcgttttc cataggctcc gccccctga cgagcatcac aaaaatcgac    120
gctcaagtca gaggtggcga acccgacag gactataaag ataccaggcg tttccccctg    180
gaagctccct cgtgcgctct cctgttccga ccctgccgct taccggatac ctgtccgcct    240
ttctcccttc gggaagcgtg gcgctttctc atagctcacg ctgtaggtat ctcagttcgg    300
tgtaggtcgt tcgctccaag ctgggctgtg tgcacgaacc cccgttcag cccgaccgct    360
gcgccttatc cggtaactat cgtcttgagt ccaacccggt aagacacgac ttatcgccac    420
tggcagcagc cactggtaac aggattagca gagcgaggta tgtaggcggt gctacagagt    480
tcttgaagtg gtggcctaac tacggctaca ctagaagaac agtatttggt atctgcgctc    540
tgctgaagcc agttaccttc ggaaaaagag ttggtagctc ttgatccggc aaacaaacca    600
ccgctggtag cggtggtttt tttgtttgca agcagcagat tacgcgcaga aaaaaggat    660
ctcaagaaga ccctttgatc ttttctacct cgaggtatag gctgtctgg gagccactcc    720
agggccacag aaatcttgtc tctgactcag gtatttttgt tttctgtttt gtgtaaatgc    780
tcttctgact aatgcaaacc atgtgtccat agaaccagaa gattttccca ggggaaaagg    840
taaggaggtg gtgagagtgt cctgggtctg cccttccagg gcttgccctg ggttaagagc    900
caggcaggaa gctctcaaga gcattgctca agagtagagg gggcctggga ggcccaggga    960
ggggatggga ggggaacacc caggctgccc ccaaccagat gccctccacc ctcctcaacc    1020
tccctcccac ggcctggaga ggtgggacca ggtatggagg cttgagagcc cctggttgga    1080
ggaagccaca agtccaggaa catggagtc tgggcagggg gcaaaggagg caggaacagg    1140
ccatcagcca ggacaggtgg taaggcaggc aggagtgttc ctgctgggaa aggtgggat    1200
caagcacctg gagggctctt cagagcaaag acaaacactg aggtcgctgc cactcctaca    1260
gagcccccac gccccgccca gctataaggg gccatgcccc aagcagggta cccaggctgc    1320
agaggtgccg gatccgatat cgtcgacaag cttggtacct ccggagcggc cgctctagag    1380
ctagcgacgt cgaattccct gtgaccctc cccagtgcct ctcctggccc tggaagttgc    1440
cactccagtg cccaccagcc ttgtcctaat aaaattaagt tgcatcattt tgtctgacta    1500
ggtgtccttc tataatatta tgggtggag gggtggta tggagcaagg gcaagttgg    1560
gaagacaacc tgtagggcct gcggggtcta ttgggaacca agctgagtg cagtggcaca    1620
atcttggctc actgcaatct ccgcctcctg ggttcaagcg attctcctgc ctcagcctcc    1680
cgagttgttg ggattccagg catgcatgac caggctcagc taattttgt ttttttggta    1740
gagacggggt ttcaccatat tggccaggct ggtctccaac tcctaatctc aggtgatcta    1800
cccaccttgg cctcccaaat tgctgggatt acaggcgtga accactgctc ccttccctgt    1860
ccttacgcgt agaattggta aagagagtcg tgtaaaatat cgagttcgca catcttgttg    1920
tctgattatt gattttggc gaaaccattt gatcatatga caagatgtgt atctacctta    1980
acttaatgat tttgataaaa atcattaact agtccatgg                          2019
```

<210> SEQ ID NO 6
<211> LENGTH: 1940
<212> TYPE: DNA
<213> ORGANISM: Homo Sapiens

<400> SEQUENCE: 6

```
ataacgcagg aaagaacatg tgagcaaaag gccagcaaaa ggccagggac cgtaaaaagg    60
ccgcgttgct ggcgttttc cataggctcc gccccctga cgagcatcac aaaaatcgac    120
```

```
gctcaagtca gaggtggcga aacccgacag gactataaag ataccaggcg tttcccctg      180 gaagctccct cgtgcgctct cctgttccga ccctgccgct taccggatac ctgtccgcct    240
ttctcccttc gggaagcgtg gcgctttctc atagctcacg ctgtaggtat ctcagttcgg    300
tgtaggtcgt tcgctccaag ctgggctgtg tgcacgaacc ccccgttcag cccgaccgct    360
gcgccttatc cggtaactat cgtcttgagt ccaacccggt aagacacgac ttatcgccac    420
tggcagcagc cactggtaac aggattagca gagcgaggta tgtaggcggt gctacagagt    480
tcttgaagtg gtggcctaac tacggctaca ctagaagaac agtatttggt atctgcgctc    540
tgctgaagcc agttaccttc ggaaaaagag ttggtagctc ttgatccggc aaacaaacca    600
ccgctggtag cggtggtttt tttgtttgca agcagcagat tacgcgcaga aaaaaggat    660 ctcaagaaga tcctttgatc ttttctacct cgagagtatc tgcagagggc cctgcgtatg    720
agtgcaagtg gttttagga ccaggatgag gcggggtggg ggtgcctacc tgacgaccga     780
ccccgaccca ctggacaagc acccaacccc cattccccaa attgcgcatc cctatcaga    840 gaggggagg ggaaacagga tgcggcgagg gcgtgcgca ctgccagctt cagcaccgcg      900
gacagtgcct tcgcccccgc ctggcggcgc gcgccaccgc cgcctcagca ctgaaggcgc    960
gctgacgtca ctcgccggtc ccccgcaaac tcccctttccc ggccaccttg gtcgcgtccg   1020
cgccgccgcc ggcccagccg gaccgcacca cgcgaggcgc gagatagggg ggcacgggcg    1080
cgaccatctg cgctgcggcg ccggcgactc agcgctgcct cagtctgcgg tgggcagcgg    1140
aggagtcgtg tcgtgcctga gagcgcagct gtgctcctgg gcaccgcgca gtccgccccc    1200
gcggctcctg gccagaccac ccctaggacc ccctgcccca agtcgcagcc ggatccgata    1260
tcgtcgacaa gcttggtacc tccggagcgg ccgctctaga gctagcgacg tcgaattccc    1320
tgtgacccct ccccagtgcc tctcctggcc ctggaagttg ccactccagt gcccaccagc    1380
cttgtcctaa taaaattaag ttgcatcatt ttgtctgact aggtgtcctt ctataatatt    1440
atggggtgga gggggtggt atggagcaag ggcaagttg gaagacaac ctgtagggcc       1500 tgcgggtct attgggaacc aagctggagt gcagtggcac atcttggct cactgcaatc     1560 tccgcctcct gggttcaagc gattctcctg cctcagcctc ccgagttgtt gggattccag    1620
gcatgcatga ccaggctcag ctaattttg ttttttggt agagacgggg tttcaccata      1680
ttggccaggc tggtctccaa ctcctaatct caggtgatct acccaccttg gcctcccaaa    1740
ttgctgggat tacaggcgtg aaccactgct cccttccctg tccttacgcg tagaattggt    1800
aaagagagtc gtgtaaaata tcgagttcgc acatcttgtt gtctgattat tgattttgg    1860 cgaaaccatt tgatcatatg acaagatgtg tatctacctt aacttaatga ttttgataaa    1920
aatcattaac tagtccatgg                                                1940

<210> SEQ ID NO 7
<211> LENGTH: 2620
<212> TYPE: DNA
<213> ORGANISM: Homo Sapiens

<400> SEQUENCE: 7
ataacgcagg aaagaacatg tgagcaaaag gccagcaaaa ggccaggac cgtaaaaagg      60 ccgcgttgct ggcgtttttc cataggctcc gccccctga cgagcatcac aaaaatcgac    120
gctcaagtca gaggtggcga aacccgacag gactataaag ataccaggcg tttcccctg    180 gaagctccct cgtgcgctct cctgttccga ccctgccgct taccggatac ctgtccgcct    240
```

```
ttctcccttc gggaagcgtg gcgctttctc atagctcacg ctgtaggtat ctcagttcgg      300
tgtaggtcgt tcgctccaag ctgggctgtg tgcacgaacc ccccgttcag cccgaccgct      360
gcgccttatc cggtaactat cgtcttgagt ccaacccggt aagacacgac ttatcgccac      420
tggcagcagc cactggtaac aggattagca gagcgaggta tgtaggcggt gctacagagt      480
tcttgaagtg gtggcctaac tacggctaca ctagaagaac agtatttggt atctgcgctc      540
tgctgaagcc agttaccttc ggaaaaagag ttggtagctc ttgatccggc aaacaaacca      600
ccgctggtag cggtggtttt tttgtttgca agcagcagat tacgcgcaga aaaaaggat       660 ctcaagaaga tcctttgatc ttttctacct cgaggtctgt aatcccagca ttttgggagg      720
ctgaggcaga tggatcacct gaggtcagga gttcgagacc agcgtggcca acatgatgaa      780 acccgtctc tagtaaaaat acaaaaatta gccaggcatg gtgctatata cctgtagcac      840
cagctacttg ggagacagag gtgggagaat tacttgaacc tgggaggttc aagccatggg      900
aggtggaagt tgcagtgagc cgagatgcca ctgcactcca gcctgagcaa cagagcaaga      960
ctatctcaag aaaagaaaga agaaagaaa gagacttgcc aaggtcatgt atcagggcaa      1020
ggaagagctg ggggcccagc tggctgctcc cctgctgagc tgggagacca ccttgatctg      1080
acttctccca tcttcccagc ctaagccagg ccctggggtc acgaggctg gggaggcacc       1140 gaggaacgcg cctggcatgt gctgacaggg gatttatgc tccagctggg ccagctggga      1200
ggagcctgct gggcagaggc cagagctggg ggctctggaa ggtacctggg ggaggttgca      1260
ctgtgagaat gagctcaagc tgggtcagag agcagggctg actctgccag tgcctgcatc      1320
agcctcatcg ctctcctagg ctcctggcct gctggactct gggctgcagg tccttcttga      1380
aaggctgtga gtagtgagac aaggagcagg agtgaggggt ggcaggagag aagatagaga      1440
ttgagagaga gagagagaga gagacagaga gagaggaaga gacagagaca aaggagaga      1500 gaacggctta gacaaggaga gaaagatgga aagataaaga gactgggcgc agtggctcac      1560
gcctgtaatc ccaacacttg ggaggccaa ggtgggagga tggcttgaag gaaagagtct       1620
gagatcaacc tggccaacat agtgagaccc cgtctctaaa aaaaaaaaa agaaaaaaaa       1680 aagaaaaaag aaaaaaaagt tttttttaaag agacagagaa agagactcag agattgagac      1740
tgagagcaag acagagagag atactcacag ggaagagggg aagaggaaaa cgagaaaggg      1800
aggagagtaa cggaaagaga taaaaagaaa aagcaggtgg cagagacaca cagagaggga      1860
cccagagaaa gccagacaga cgcaggtggc tggcagcggg cgctgtgggg gtcacagtag      1920
ggggacctgt ggatccgata tcgtcgacaa gcttggtacc tccggagcgg ccgctctaga      1980
gctagcgacg tcgaattccc tgtgaccct ccccagtgcc tctcctggcc ctggaagttg       2040
ccactccagt gcccaccagc cttgtcctaa taaaattaag ttgcatcatt ttgtctgact      2100
aggtgtcctt ctataatatt atggggtgga gggggtggt atggagcaag gggcaagttg       2160
ggaagacaac ctgtagggcc tgcggggtct attgggaacc aagctggagt gcagtggcac      2220
aatcttggct cactgcaatc tccgcctcct gggttcaagc gattctcctg cctcagcctc      2280
ccgagttgtt gggattccag gcatgcatga ccaggctcag ctaatttttg tttttttggt      2340
agagacgggg tttcaccata ttggccaggc tggtctccaa ctcctaatct caggtgatct      2400
acccaccttg gcctcccaaa ttgctgggat tacaggcgtg aaccactgct cccttccctg      2460
tccttacgcg tagaattggt aaagagagtc gtgtaaaata tcgagttcgc acatcttgtt      2520
gtctgattat tgattttggg cgaaaccatt tgatcatatg acaagatgtg tatctacctt      2580
aacttaatga ttttgataaa aatcattaac tagtccatgg                            2620
```

<210> SEQ ID NO 8
<211> LENGTH: 2240
<212> TYPE: DNA
<213> ORGANISM: Homo Sapiens

<400> SEQUENCE: 8

| | | | | | |
|---|---|---|---|---|---|
| ataacgcagg | aaagaacatg | tgagcaaaag | gccagcaaaa | ggccagggac cgtaaaaagg | 60 |
| ccgcgttgct | ggcgttttc | cataggctcc | gcccccctga | cgagcatcac aaaaatcgac | 120 |
| gctcaagtca | gaggtggcga | aacccgacag | gactataaag | ataccaggcg tttccccctg | 180 |
| gaagctccct | cgtgcgctct | cctgttccga | ccctgccgct | taccggatac ctgtccgcct | 240 |
| ttctcccttc | gggaagcgtg | gcgctttctc | atagctcacg | ctgtaggtat ctcagttcgg | 300 |
| tgtaggtcgt | tcgctccaag | ctgggctgtg | tgcacgaacc | ccccgttcag cccgaccgct | 360 |
| gcgccttatc | cggtaactat | cgtcttgagt | ccaacccggt | aagacacgac ttatcgccac | 420 |
| tggcagcagc | cactggtaac | aggattagca | gagcgaggta | tgtaggcggt gctacagagt | 480 |
| tcttgaagtg | gtggcctaac | tacggctaca | ctagaagaac | agtatttggt atctgcgctc | 540 |
| tgctgaagcc | agttaccttc | ggaaaaagag | ttggtagctc | ttgatccggc aaacaaacca | 600 |
| ccgctggtag | cggtggtttt | tttgtttgca | agcagcagat | tacgcgcaga aaaaaggat | 660 |
| ctcaagaaga | tcctttgatc | ttttctacct | cgaggccaag | aacatcttaa gtcacagaaa | 720 |
| cattagtttt | tggaagcagg | gtttgctgta | actatagtag | aaatgacatt ctgattccac | 780 |
| tcctagcttc | acaaggatat | ctgtgaaaga | tttggggcaa | aactgttaag ctgtctgaaa | 840 |
| gtgcttttgc | ataagaaatg | ggttttactg | ctaaaactgt | catattgctg agttttgaat | 900 |
| gccctaatgg | taaatgatac | tgggttgcca | aaaataacca | gattagtagt tttttcattc | 960 |
| atttggccgt | ctcagtaagt | caaatattga | tactttctac | taagtcatct tgccaacacc | 1020 |
| cattttgtta | tacttatgct | gaatctgttt | gtcatctctt | aagtaagaaa attattgatt | 1080 |
| attttgtggg | gatttaattt | aaaaaaatg | gtaatggata | ctgtaaagga gcattatttg | 1140 |
| gatggtttaa | aaacatcttc | cttgatggga | aaatcttta | aaaggctttc taacttggtg | 1200 |
| taattacttg | aattaaggaa | gtgcaatgcc | attctactga | cttagaacaa ctttttttgac | 1260 |
| ttcctgcaaa | gaggaccctt | acagtatttt | tggagaagtt | agtaaaaccg aatctgacat | 1320 |
| catcacctag | cagttcatgc | agctagcaag | tggtttgttc | ttagggtaac agaggaggaa | 1380 |
| attgttcctc | gtctgataag | acaacagtgg | agagtatgca | tttatttatt tacttttaca | 1440 |
| tttttgattc | gttttacag | agaaaaactt | ctacagagat | aacaattatt ttgcttttca | 1500 |
| gaaggacgca | tgctgtttct | tagggacacg | gctgacttcc | agatatgacc ggatccgata | 1560 |
| tcgtcgacaa | gcttggtacc | tccggagcgg | ccgctctaga | gctagcgacg tcgaattccc | 1620 |
| tgtgacccct | ccccagtgcc | tctcctggcc | ctggaagttg | ccactccagt gcccaccagc | 1680 |
| cttgtcctaa | taaaattaag | ttgcatcatt | ttgtctgact | aggtgtcctt ctataatatt | 1740 |
| atggggtgga | ggggggtggt | atggagcaag | gggcaagttg | ggaagacaac ctgtagggcc | 1800 |
| tgcggggtct | attgggaacc | aagctggagt | gcagtggcac | aatcttggct cactgcaatc | 1860 |
| tccgcctcct | gggttcaagc | gattctcctg | cctcagcctc | ccgagttgtt gggattccag | 1920 |
| gcatgcatga | ccaggctcag | ctaattttg | tttttttggt | agagacgggg tttcaccata | 1980 |
| ttggccaggc | tggtctccaa | ctcctaatct | caggtgatct | acccaccttg gcctcccaaa | 2040 |
| ttgctgggat | tacaggcgtg | aaccactgct | cccttccctg | tccttacgcg tagaattggt | 2100 |

```
aaagagagtc gtgtaaaata tcgagttcgc acatcttgtt gtctgattat tgattttttgg    2160 cgaaaccatt tgatcatatg acaagatgtg tatctacctt aacttaatga ttttgataaa    2220
aatcattaac tagtccatgg                                                2240

<210> SEQ ID NO 9
<211> LENGTH: 2604
<212> TYPE: DNA
<213> ORGANISM: Homo Sapiens

<400> SEQUENCE: 9
ataacgcagg aaagaacatg tgagcaaaag gccagcaaaa ggccagggac cgtaaaaagg      60
ccgcgttgct ggcgtttttc cataggctcc gcccccctga cgagcatcac aaaaatcgac     120
gctcaagtca gaggtggcga aacccgacag gactataaag ataccaggcg tttccccctg     180
gaagctccct cgtgcgctct cctgttccga ccctgccgct taccggatac ctgtccgcct     240
ttctcccttc gggaagcgtg gcgctttctc atagctcacg ctgtaggtat ctcagttcgg     300
tgtaggtcgt tcgctccaag ctgggctgtg tgcacgaacc ccccgttcag cccgaccgct     360
gcgccttatc cggtaactat cgtcttgagt ccaacccggt aagacacgac ttatcgccac     420
tggcagcagc cactggtaac aggattagca gagcgaggta tgtaggcggt gctacagagt     480
tcttgaagtg gtggcctaac tacggctaca ctagaagaac agtatttggt atctgcgctc     540
tgctgaagcc agttaccttc ggaaaaagag ttggtagctc ttgatccggc aaacaaacca     600
ccgctggtag cggtggtttt tttgtttgca agcagcagat tacgcgcaga aaaaaaggat     660
ctcaagaaga tcctttgatc ttttctacct cgagaaacgg agggttgtga ggagagtgag     720
aggtggacag agggcaccga cgatttagca tctcttcctc tcctgggggt cgaggatgag     780
agacaaaaaa gaagctgcca ggaaacataa aattcagagg gctcagctgc agggctgagg     840
tctgcaagca tgctgtgtac acttgtgcat gttgtgccct gcacaagggc atctctgaag     900
gggctgcatt ggacccaggg gcaggggcgc aaaggtgagt ttatatcagt tcctgagcac     960
tgtggctcca tccagcactc tgaggacagg caggatacag ctggaggacc tgagggctcc    1020
cccacaccag cttctgttcc ctgcccaaga ccccctggac ctgcagacaa caattcaacg    1080
cactcagagt cccacagtta agaactccct gaagaagccc ccagtggctg cgtggtggat    1140
tttcgcaaag ctgtctccac ctacatccac cctgtttggc agcccctaca tactctttca    1200
cagcatgagg aagggaggcc tctcaccaag acctggactg aatcttctcc cagtggctgc    1260
cacacctgac ctgctcttgc tccagaacct ctgtggctcc catactccac agggtcaact    1320
tccaacatgg ctgcctgcac tccagccaag aggctctgct ctgggcccct ccagatgcct    1380
gacctgggtc tgtggctgcc ctgtccttct tcagtgctcc tcttcccgct gggtgaggaa    1440
tagttcagga cagaggagct aagttcaggt tcattcatag acaggtgcc tatttcgctc    1500 acggcccagg aatagagact tgccgggctc ggcccttcgg ggagctggca gacggcagag    1560
gggaggctgg ctgcccagg ggatgaccac cgtgggggta agcacagaca gaggggagca    1620
caggcttccc ccagaagact gagaggcccc ccagaggcat ccacagagga ccccagctgt    1680
gctgcccaag ctgggcgacc gccaaaccctt agcggcccag ctgacaaaag cctgccctcc    1740
cccagggtcc ccggagagct ggtgcctccc ctgggtccca atttgcatgg caggaagggg    1800
cctggtgagg aagaggcggg gaggggacag gctgcagccg gtgcagttac acgttttcct    1860
ccaaggagcc tcggacgttg tcacgggttt ggggtcgggg acagagcggt gaccggatcc    1920
gatatcgtcg acaagcttgg tacctccgga gcggccgctc tagagctagc gacgtcgaat    1980
```

```
tccctgtgac ccctccccag tgcctctcct ggccctggaa gttgccactc cagtgcccac    2040
cagccttgtc ctaataaaat taagttgcat cattttgtct gactaggtgt ccttctataa    2100
tattatgggg tggagggggg tggtatggag caaggggcaa gttgggaaga caacctgtag    2160
ggcctgcggg gtctattggg aaccaagctg gagtgcagtg gcacaatctt ggctcactgc    2220
aatctccgcc tcctgggttc aagcgattct cctgcctcag cctcccgagt tgttgggatt    2280
ccaggcatgc atgaccaggc tcagctaatt tttgttttt tggtagagac ggggtttcac     2340
catattggcc aggctggtct ccaactccta atctcaggtg atctacccac cttggcctcc    2400
caaattgctg ggattacagg cgtgaaccac tgctcccttc cctgtcctta cgcgtagaat    2460
tggtaaagag agtcgtgtaa aatatcgagt tcgcacatct tgttgtctga ttattgattt    2520
ttggcgaaac catttgatca tatgacaaga tgtgtatcta ccttaactta atgatttga    2580 taaaaatcat taactagtcc atgg                                            2604

<210> SEQ ID NO 10
<211> LENGTH: 2048
<212> TYPE: DNA
<213> ORGANISM: Homo Sapiens

<400> SEQUENCE: 10
ataacgcagg aaagaacatg tgagcaaaag gccagcaaaa ggccagggac cgtaaaaagg      60
ccgcgttgct ggcgtttttc cataggctcc gcccccctga cgagcatcac aaaaatcgac     120
gctcaagtca gaggtggcga aacccgacag gactataaag ataccaggcg tttccccctg     180
gaagctccct cgtgcgctct cctgttccga ccctgccgct taccggatac ctgtccgcct     240
ttctcccttc gggaagcgtg cgctttctc atagctcacg ctgtaggtat ctcagttcgg      300
tgtaggtcgt tcgctccaag ctgggctgtg tgcacgaacc ccccgttcag cccgaccgct     360
gcgccttatc cggtaactat cgtcttgagt ccaacccggt aagacacgac ttatcgccac     420
tggcagcagc cactggtaac aggattagca gagcgaggta tgtaggcggt gctacagagt     480
tcttgaagtg gtggcctaac tacggctaca ctagaagaac agtatttggt atctgcgctc     540
tgctgaagcc agttaccttc ggaaaaagag ttggtagctc ttgatccggc aaacaaacca     600
ccgctggtag cggtggtttt tttgtttgca agcagcagat tacgcgcaga aaaaaaggat     660
ctcaagaaga tcctttgatc ttttctacct cgagtcattt cttacctccc cttccctctc     720
ccacctgcta ctgggtgcat ctctgctccc cccttcccca gcagatggtt acctttgggc     780
tgttgctttc ttgtcaccat ctgagttctc agacgctgga aagccatgtt ctcggctctg     840
tgaatgacaa tgctgactgg agtgctgccc ctctgtaaag gctgggtgt ggatggtcac      900 aagccccca catgcctcag ccaagaggaa gtagtacagg ggtcagccca gaggtccagg     960
ggaaaggagt ggaaaccgat ttccccacca agggaggggc ctgtacctca gctgttccca    1020
tagctacttg ccacaactgc caagcaagtt tcgctgagtt tgacacatgg atccctgtgg    1080
atcaactgcc ctaggactcc gtttgcaccc atgtgacact gttgactttg ccctgatgaa    1140
gcagggccaa cagtccccta acttaattac aaaaactaat gactaagaga gaggtggcta    1200
gagctgaggc ccctgagtca ggctgtgggt gggatcatct ccagtacagg aagtgagact    1260
ttcatttcct cctttccaag agagggctga gggagcaggg ttgagcaact ggtgcagaca    1320
gcctagctgg actttgggtg aggcggttca gcagatctgg atccgatatc gtcgacaagc    1380
ttggtacctc cggagcggcc gctctagagc tagcgacgtc gaattccctg tgaccctcc    1440
```

-continued

| | |
|---|---|
| ccagtgcctc tcctggccct ggaagttgcc actccagtgc ccaccagcct tgtcctaata | 1500 |
| aaattaagtt gcatcatttt gtctgactag gtgtccttct ataatattat ggggtggagg | 1560 |
| ggggtggtat ggagcaaggg gcaagttggg aagacaacct gtagggcctg cggggtctat | 1620 |
| tgggaaccaa gctggagtgc agtggcacaa tcttggctca ctgcaatctc cgcctcctgg | 1680 |
| gttcaagcga ttctcctgcc tcagcctccc gagttgttgg gattccaggc atgcatgacc | 1740 |
| aggctcagct aatttttgtt tttttggtag agacggggtt tcaccatatt ggccaggctg | 1800 |
| gtctccaact cctaatctca ggtgatctac ccaccttggc ctcccaaatt gctgggatta | 1860 |
| caggcgtgaa ccactgctcc cttccctgtc cttacgcgta gaattggtaa agagagtcgt | 1920 |
| gtaaaatatc gagttcgcac atcttgttgt ctgattattg attttggcg aaaccatttg | 1980 |
| atcatatgac aagatgtgta tctaccttaa cttaatgatt ttgataaaaa tcattaacta | 2040 |
| gtccatgg | 2048 |

<210> SEQ ID NO 11
<211> LENGTH: 1978
<212> TYPE: DNA
<213> ORGANISM: Homo Sapiens

<400> SEQUENCE: 11

| | |
|---|---|
| ataacgcagg aaagaacatg tgagcaaaag gccagcaaaa ggccagggac cgtaaaaagg | 60 |
| ccgcgttgct ggcgtttttc cataggctcc gcccccctga cgagcatcac aaaaatcgac | 120 |
| gctcaagtca gaggtggcga aacccgacag gactataaag ataccaggcg tttccccctg | 180 |
| gaagctccct cgtgcgctct cctgttccga ccctgccgct taccggatac ctgtccgcct | 240 |
| ttctcccttc gggaagcgtg gcgctttctc atagctcacg ctgtaggtat ctcagttcgg | 300 |
| tgtaggtcgt tcgctccaag ctgggctgtg tgcacgaacc cccgttcag cccgaccgct | 360 |
| gcgccttatc cggtaactat cgtcttgagt ccaacccggt aagacacgac ttatcgccac | 420 |
| tggcagcagc cactggtaac aggattagca gagcgaggta tgtaggcggt gctacagagt | 480 |
| tcttgaagtg gtggcctaac tacggctaca ctagaagaac agtatttggt atctgcgctc | 540 |
| tgctgaagcc agttaccttc ggaaaaagag ttggtagctc ttgatccggc aaacaaacca | 600 |
| ccgctggtag cggtggtttt tttgtttgca agcagcagat tacgcgcaga aaaaaggat | 660 |
| ctcaagaaga tcctttgatc ttttctacct cgaggacagc agcgcaaaga gccccgccct | 720 |
| gcagcctcca gctctcctgg tctaatgtgg aaagtggccc aggtgagggc tttgctctcc | 780 |
| tggagacatt tgccccccagc tgtgagcagg acaggtctg gccaccgggc ccctggttaa | 840 |
| gactctaatg acccgctggt cctgaggaag aggtgctgac gaccaaggag atcttcccac | 900 |
| agacccagca ccagggaaat ggtccggaaa ttgcagcctc agcccccagc catctgccga | 960 |
| ccccctcacc ccaggcccta atgggccagg cggcaggggt tgacaggtag gggagatggg | 1020 |
| ctctgagact ataaagccag cggggggccca gcagccctca gccctccagg acaggctgca | 1080 |
| tcagaagagg ccatcaagca ggtctgttcc aagggccttt gcgtcaggtg ggctcagggt | 1140 |
| tccagggtgg ctggacccca ggccccagct ctgcagcagg aggacgtgg ctgggctcgt | 1200 |
| gaagcatgtg ggggtgagcc caggggcccc aaggcagggc acctggcctt cagcctgcct | 1260 |
| cagccctgcc tgtctcccaa tcactgtcgg atccgatatc gtcgacaagc ttggtacctc | 1320 |
| cggagcggcc gctctagagc tagcgacgtc gaattccctg tgacccctcc ccagtgcctc | 1380 |
| tcctggccct ggaagttgcc actccagtgc ccaccagcct tgtcctaata aaattaagtt | 1440 |
| gcatcatttt gtctgactag gtgtccttct ataatattat ggggtggagg ggggtggtat | 1500 |

-continued

```
ggagcaaggg gcaagttggg aagacaacct gtagggcctg cggggtctat tgggaaccaa  1560
gctggagtgc agtggcacaa tcttggctca ctgcaatctc cgcctcctgg gttcaagcga  1620
ttctcctgcc tcagcctccc gagttgttgg gattccaggc atgcatgacc aggctcagct  1680 aattttgtt ttttggtag agacggggtt tcaccatatt ggccaggctg gtctccaact   1740
cctaatctca ggtgatctac ccaccttggc ctcccaaatt gctgggatta caggcgtgaa  1800
ccactgctcc cttccctgtc cttacgcgta gaattggtaa agagagtcgt gtaaaatatc  1860
gagttcgcac atcttgttgt ctgattattg attttggcg aaaccatttg atcatatgac   1920
aagatgtgta tctaccttaa cttaatgatt ttgataaaaa tcattaacta gtccatgg    1978
```

<210> SEQ ID NO 12
<211> LENGTH: 42
<212> TYPE: DNA
<213> ORGANISM: Artificial Sequence
<220> FEATURE:
<223> OTHER INFORMATION: Oligonucleotide UCori-Bam

<400> SEQUENCE: 12
ggatccagat ctactcgagg tagaaaagat caaaggatct tc                42

<210> SEQ ID NO 13
<211> LENGTH: 31
<212> TYPE: DNA
<213> ORGANISM: Artificial Sequence
<220> FEATURE:
<223> OTHER INFORMATION: Oligonucleotide UCori-Nco

<400> SEQUENCE: 13
agtccatgga taacgcagga aagaacatgt g                           31

<210> SEQ ID NO 14
<211> LENGTH: 31
<212> TYPE: DNA
<213> ORGANISM: Artificial Sequence
<220> FEATURE:
<223> OTHER INFORMATION: Oligonucleotide hGH-F

<400> SEQUENCE: 14
aggatccgaa ttccctgtga ccccctcccca g                          31

<210> SEQ ID NO 15
<211> LENGTH: 40
<212> TYPE: DNA
<213> ORGANISM: Artificial Sequence
<220> FEATURE:
<223> OTHER INFORMATION: Oligonucleotide hGH-R

<400> SEQUENCE: 15
ctctttacca attctacgcg taaggacagg gaagggagca                  40

<210> SEQ ID NO 16
<211> LENGTH: 40
<212> TYPE: DNA
<213> ORGANISM: Artificial Sequence
<220> FEATURE:
<223> OTHER INFORMATION: Oligonucleotide RO-F

<400> SEQUENCE: 16
cttccctgtc cttacgcgta gaattggtaa agagagtcgt                  40

<210> SEQ ID NO 17

```
<211> LENGTH: 41
<212> TYPE: DNA
<213> ORGANISM: Artificial Sequence
<220> FEATURE:
<223> OTHER INFORMATION: Oligonucleotide RO-R

<400> SEQUENCE: 17
ccgtagaaaa ctagttaatg atttttatca aaatcattaa g                    41

<210> SEQ ID NO 18
<211> LENGTH: 49
<212> TYPE: DNA
<213> ORGANISM: Artificial Sequence
<220> FEATURE:
<223> OTHER INFORMATION: Oligonucleotide RO-1

<400> SEQUENCE: 18
gaattggtaa agagagtcgt gtaaaatatc gagttcgcac atcttgttg            49

<210> SEQ ID NO 19
<211> LENGTH: 47
<212> TYPE: DNA
<213> ORGANISM: Artificial Sequence
<220> FEATURE:
<223> OTHER INFORMATION: Oligonucleotide RO-2

<400> SEQUENCE: 19 gattttggc gaaccattt gatcatatga caagatgtgt atctacc                47

<210> SEQ ID NO 20
<211> LENGTH: 47
<212> TYPE: DNA
<213> ORGANISM: Artificial Sequence
<220> FEATURE:
<223> OTHER INFORMATION: Oligonucleotide RO-3

<400> SEQUENCE: 20 atgatttta tcaaaatcat taagttaagg tagatacaca tcttgtc               47

<210> SEQ ID NO 21
<211> LENGTH: 34
<212> TYPE: DNA
<213> ORGANISM: Artificial Sequence
<220> FEATURE:
<223> OTHER INFORMATION: Oligonucleotide Kan-F

<400> SEQUENCE: 21
aaatcattaa ctagtttct acggggtctg acgc                             34

<210> SEQ ID NO 22
<211> LENGTH: 33
<212> TYPE: DNA
<213> ORGANISM: Artificial Sequence
<220> FEATURE:
<223> OTHER INFORMATION: Oligonucleotide Kan-R

<400> SEQUENCE: 22
cagccatgga ctagtggtgg cacttttcgg gga                             33

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide MCS1

<400> SEQUENCE: 23
```
gatccgatat cgtcgacaag cttggtacct                                          30

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide MCS2

<400> SEQUENCE: 24
caagcttgtc gacgatatcg                                                     20

<210> SEQ ID NO 25
<211> LENGTH: 32
<212> TYPE: DNA
<213> ORGANISM: Artificial Sequence
<220> FEATURE:
<223> OTHER INFORMATION: Oligonucleotide MCS3

<400> SEQUENCE: 25
ccggagcggc cgctctagag ctagcgacgt cg                                       32

<210> SEQ ID NO 26
<211> LENGTH: 42
<212> TYPE: DNA
<213> ORGANISM: Artificial Sequence
<220> FEATURE:
<223> OTHER INFORMATION: Oligonucleotide MCS4

<400> SEQUENCE: 26
aattcgacgt cgctagctct agagcggccg ctccggaggt ac                            42

<210> SEQ ID NO 27
<211> LENGTH: 30
<212> TYPE: DNA
<213> ORGANISM: Artificial Sequence
<220> FEATURE:
<223> OTHER INFORMATION: Oligonucleotide Myo-F

<400> SEQUENCE: 27
tacctcgagg tggccaagct tagaaacatg                                          30

<210> SEQ ID NO 28
<211> LENGTH: 28
<212> TYPE: DNA
<213> ORGANISM: Artificial Sequence
<220> FEATURE:
<223> OTHER INFORMATION: Oligonucleotide Myo-R

<400> SEQUENCE: 28
tggatcctta taccttctgg gatgcttg                                            28

<210> SEQ ID NO 29
<211> LENGTH: 33
<212> TYPE: DNA
<213> ORGANISM: Artificial Sequence
<220> FEATURE:
<223> OTHER INFORMATION: Oligonucleotide Els-F

<400> SEQUENCE: 29
acctcgagca tcttatttct gaaaagagt ttg                                       33

<210> SEQ ID NO 30
<211> LENGTH: 25
<212> TYPE: DNA

```
<213> ORGANISM: Artificial Sequence
<220> FEATURE:
<223> OTHER INFORMATION: Oligonucleotide Els-R

<400> SEQUENCE: 30
ggatcctgcc gatggagtag accac                                            25

<210> SEQ ID NO 31
<211> LENGTH: 29
<212> TYPE: DNA
<213> ORGANISM: Artificial Sequence
<220> FEATURE:
<223> OTHER INFORMATION: Oligonucleotide ICAM-F

<400> SEQUENCE: 31
tacctcgagg tctcccaggc atgactcca                                        29

<210> SEQ ID NO 32
<211> LENGTH: 28
<212> TYPE: DNA
<213> ORGANISM: Artificial Sequence
<220> FEATURE:
<223> OTHER INFORMATION: Oligonucleotide ICAM-R

<400> SEQUENCE: 32
cggatccgac tggcagtctc cacgggct                                         28

<210> SEQ ID NO 33
<211> LENGTH: 27
<212> TYPE: DNA
<213> ORGANISM: Artificial Sequence
<220> FEATURE:
<223> OTHER INFORMATION: Oligonucleotide OS2-F

<400> SEQUENCE: 33
acctcgagca cccacagcag gctgcct                                          27

<210> SEQ ID NO 34
<211> LENGTH: 24
<212> TYPE: DNA
<213> ORGANISM: Artificial Sequence
<220> FEATURE:
<223> OTHER INFORMATION: Oligonucleotide OS2-R

<400> SEQUENCE: 34
ggatcctggc tgcgctgggc tgct                                             24

<210> SEQ ID NO 35
<211> LENGTH: 27
<212> TYPE: DNA
<213> ORGANISM: Artificial Sequence
<220> FEATURE:
<223> OTHER INFORMATION: Oligonucleotide Spb-F

<400> SEQUENCE: 35
acctcgaggt atagggctgt ctgggag                                          27

<210> SEQ ID NO 36
<211> LENGTH: 24
<212> TYPE: DNA
<213> ORGANISM: Artificial Sequence
<220> FEATURE:
<223> OTHER INFORMATION: Oligonucleotide Spb-R

<400> SEQUENCE: 36
ggatccggca cctctgcagc ctgg                                             24
```

<210> SEQ ID NO 37
<211> LENGTH: 27
<212> TYPE: DNA
<213> ORGANISM: Artificial Sequence
<220> FEATURE:
<223> OTHER INFORMATION: Oligonucleotide Syn-F

<400> SEQUENCE: 37
tactcgagag tatctgcaga gggccct                    27

<210> SEQ ID NO 38
<211> LENGTH: 24
<212> TYPE: DNA
<213> ORGANISM: Artificial Sequence
<220> FEATURE:
<223> OTHER INFORMATION: Oligonucleotide Syn-R

<400> SEQUENCE: 38
ggatccggct gcgacttggg gcag                       24

<210> SEQ ID NO 39
<211> LENGTH: 29
<212> TYPE: DNA
<213> ORGANISM: Artificial Sequence
<220> FEATURE:
<223> OTHER INFORMATION: Oligonucleotide NPHS-F

<400> SEQUENCE: 39
acctcgaggt ctgtaatccc agcattttg                  29

<210> SEQ ID NO 40
<211> LENGTH: 25
<212> TYPE: DNA
<213> ORGANISM: Artificial Sequence
<220> FEATURE:
<223> OTHER INFORMATION: Oligonucleotide NPHS-R

<400> SEQUENCE: 40
ggatccacag gtcccccta ctgtga                      25

<210> SEQ ID NO 41
<211> LENGTH: 29
<212> TYPE: DNA
<213> ORGANISM: Artificial Sequence
<220> FEATURE:
<223> OTHER INFORMATION: Oligonucleotide cd45-F

<400> SEQUENCE: 41
atctcgaggc caagaacatc ttaagtcac                  29

<210> SEQ ID NO 42
<211> LENGTH: 26
<212> TYPE: DNA
<213> ORGANISM: Artificial Sequence
<220> FEATURE:
<223> OTHER INFORMATION: Oligonucleotide cd45-R

<400> SEQUENCE: 42
ggatccggtc atatctggaa gtcagc                     26

<210> SEQ ID NO 43
<211> LENGTH: 28
<212> TYPE: DNA
<213> ORGANISM: Artificial Sequence
<220> FEATURE:

```
<223> OTHER INFORMATION: Oligonucleotide b29-F

<400> SEQUENCE: 43
acctcgagaa acggagggtt gtgaggag                                          28

<210> SEQ ID NO 44
<211> LENGTH: 26
<212> TYPE: DNA
<213> ORGANISM: Artificial Sequence
<220> FEATURE:
<223> OTHER INFORMATION: Oligonucleotide b29-R

<400> SEQUENCE: 44
ggatccggtc accgctctgt ccccga                                            26

<210> SEQ ID NO 45
<211> LENGTH: 28
<212> TYPE: DNA
<213> ORGANISM: Artificial Sequence
<220> FEATURE:
<223> OTHER INFORMATION: Oligonucleotide cd68-F

<400> SEQUENCE: 45
tactcgagtc atttcttacc tccccttc                                          28

<210> SEQ ID NO 46
<211> LENGTH: 26
<212> TYPE: DNA
<213> ORGANISM: Artificial Sequence
<220> FEATURE:
<223> OTHER INFORMATION: Oligonucleotide cd68-R

<400> SEQUENCE: 46
atagatctgc tgaaccgcct caccca                                            26

<210> SEQ ID NO 47
<211> LENGTH: 26
<212> TYPE: DNA
<213> ORGANISM: Artificial Sequence
<220> FEATURE:
<223> OTHER INFORMATION: Oligonucleotide Ins-F

<400> SEQUENCE: 47
acctcgagga cagcagcgca aagagc                                            26

<210> SEQ ID NO 48
<211> LENGTH: 26
<212> TYPE: DNA
<213> ORGANISM: Artificial Sequence
<220> FEATURE:
<223> OTHER INFORMATION: Oligonucleotide Ins-R

<400> SEQUENCE: 48
ggatccgaca gtgatctggg agacag                                            26

<210> SEQ ID NO 49
<211> LENGTH: 39
<212> TYPE: DNA
<213> ORGANISM: Artificial Sequence
<220> FEATURE:
<223> OTHER INFORMATION: Oligonucleotide VEGF165_F

<400> SEQUENCE: 49
aggatccacc ggtcgccacc atgaactttc tgctgtctt                              39
```

```
<210> SEQ ID NO 50
<211> LENGTH: 26
<212> TYPE: DNA
<213> ORGANISM: Artificial Sequence
<220> FEATURE:
<223> OTHER INFORMATION: Oligonucleotide VEGF165_R

<400> SEQUENCE: 50
ggaattctca ccgcctcggc ttgtca                                       26

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide VEGF165_SF

<400> SEQUENCE: 51
atgaactttc tgctgtcttg                                              20

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide VEGF165_SR

<400> SEQUENCE: 52
tcaccgcctc ggcttgtcac                                              20

<210> SEQ ID NO 53
<211> LENGTH: 42
<212> TYPE: DNA
<213> ORGANISM: Artificial Sequence
<220> FEATURE:
<223> OTHER INFORMATION: Oligonucleotide CAT_F

<400> SEQUENCE: 53
ccgatatcgg taccgaggag atctgccgcc gcgatcgcca tg                     42

<210> SEQ ID NO 54
<211> LENGTH: 33
<212> TYPE: DNA
<213> ORGANISM: Artificial Sequence
<220> FEATURE:
<223> OTHER INFORMATION: Oligonucleotide CAT_R

<400> SEQUENCE: 54
gctctagatc acagatttgc cttctccctt gcc                               33

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide CAT_SF

<400> SEQUENCE: 55
cctatcctga cactcaccgc                                              20

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide CAT_SR
```

-continued

<400> SEQUENCE: 56
atagaatgcc cgcacctgag                                              20

<210> SEQ ID NO 57
<211> LENGTH: 29
<212> TYPE: DNA
<213> ORGANISM: Artificial Sequence
<220> FEATURE:
<223> OTHER INFORMATION: Oligonucleotide HIF1a_F

<400> SEQUENCE: 57
cggatccgga cgtccgccat ggagggcgc                                    29

<210> SEQ ID NO 58
<211> LENGTH: 31
<212> TYPE: DNA
<213> ORGANISM: Artificial Sequence
<220> FEATURE:
<223> OTHER INFORMATION: Oligonucleotide HIF1a_R

<400> SEQUENCE: 58
gctctagact agttaacttg atccaaagct c                                 31

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide HIF1a_SF

<400> SEQUENCE: 59
tcaaagtcgg acagcctcac                                              20

<210> SEQ ID NO 60
<211> LENGTH: 20
<212> TYPE: DNA
<213> ORGANISM: Artificial Sequence
<220> FEATURE:
<223> OTHER INFORMATION: Oligonucleotide HIF1a_SR

<400> SEQUENCE: 60
atccattgat tgccccagca                                              20

<210> SEQ ID NO 61
<211> LENGTH: 34
<212> TYPE: DNA
<213> ORGANISM: Artificial Sequence
<220> FEATURE:
<223> OTHER INFORMATION: Oligonucleotide BMP2_F

<400> SEQUENCE: 61
caggatccct cctaaaggtc caccatggtg gccg                              34

<210> SEQ ID NO 62
<211> LENGTH: 32
<212> TYPE: DNA
<213> ORGANISM: Artificial Sequence
<220> FEATURE:
<223> OTHER INFORMATION: Oligonucleotide BMP2_R

<400> SEQUENCE: 62
gggaattcct agcgacaccc acaaccctcc ac                                32

<210> SEQ ID NO 63
<211> LENGTH: 20

```
<212> TYPE: DNA
<213> ORGANISM: Artificial Sequence
<220> FEATURE:
<223> OTHER INFORMATION: Oligonucleotide BMP2_SF

<400> SEQUENCE: 63
atgcaagcag gtgggaaagt                                              20

<210> SEQ ID NO 64
<211> LENGTH: 20
<212> TYPE: DNA
<213> ORGANISM: Artificial Sequence
<220> FEATURE:
<223> OTHER INFORMATION: Oligonucleotide BMP2_SR

<400> SEQUENCE: 64
gggagccaca atccagtcat                                              20

<210> SEQ ID NO 65
<211> LENGTH: 28
<212> TYPE: DNA
<213> ORGANISM: Artificial Sequence
<220> FEATURE:
<223> OTHER INFORMATION: Oligonucleotide CFTR_F

<400> SEQUENCE: 65
atcgtcgacc gccatgcaga ggtcgcct                                     28

<210> SEQ ID NO 66
<211> LENGTH: 30
<212> TYPE: DNA
<213> ORGANISM: Artificial Sequence
<220> FEATURE:
<223> OTHER INFORMATION: Oligonucleotide CFTR_R

<400> SEQUENCE: 66
agagcggccg cttaaagcct tgtatcttgc                                   30

<210> SEQ ID NO 67
<211> LENGTH: 18
<212> TYPE: DNA
<213> ORGANISM: Artificial Sequence
<220> FEATURE:
<223> OTHER INFORMATION: Oligonucleotide CFTR_SF

<400> SEQUENCE: 67
aggaggaacg ctctatcg                                                18

<210> SEQ ID NO 68
<211> LENGTH: 18
<212> TYPE: DNA
<213> ORGANISM: Artificial Sequence
<220> FEATURE:
<223> OTHER INFORMATION: Oligonucleotide CFTR_SR

<400> SEQUENCE: 68
gcagacgcct gtaacaac                                                18

<210> SEQ ID NO 69
<211> LENGTH: 28
<212> TYPE: DNA
<213> ORGANISM: Artificial Sequence
<220> FEATURE:
<223> OTHER INFORMATION: Oligonucleotide BDNF_F

<400> SEQUENCE: 69
```
atcgtcgacc gccatgcaga ggtcgcct                                    28

<210> SEQ ID NO 70
<211> LENGTH: 30
<212> TYPE: DNA
<213> ORGANISM: Artificial Sequence
<220> FEATURE:
<223> OTHER INFORMATION: Oligonucleotide BDNF_R

<400> SEQUENCE: 70
gggaattctc atcttcccct tttaatggtc                                  30

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide BDNF_SF

<400> SEQUENCE: 71
tttggttgca tgaaggctgc                                             20

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide BDNF_SR

<400> SEQUENCE: 72
gccgaacttt ctggtcctca                                             20

<210> SEQ ID NO 73
<211> LENGTH: 35
<212> TYPE: DNA
<213> ORGANISM: Artificial Sequence
<220> FEATURE:
<223> OTHER INFORMATION: Oligonucleotide ATGL_F

<400> SEQUENCE: 73
gtggatccct gtgggacatg tttccccgcg agaag                            35

<210> SEQ ID NO 74
<211> LENGTH: 31
<212> TYPE: DNA
<213> ORGANISM: Artificial Sequence
<220> FEATURE:
<223> OTHER INFORMATION: Oligonucleotide ATGL_R

<400> SEQUENCE: 74
ggaattctca cagccccagg gccccgatca c                                31

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide ATGL_SF

<400> SEQUENCE: 75
ggtcacagta gggggacctg                                             20

<210> SEQ ID NO 76
<211> LENGTH: 20
<212> TYPE: DNA
<213> ORGANISM: Artificial Sequence

```
<220> FEATURE:
<223> OTHER INFORMATION: Oligonucleotide ATGL_SR

<400> SEQUENCE: 76
gacattctcg ccgtctgaca                                                    20

<210> SEQ ID NO 77
<211> LENGTH: 33
<212> TYPE: DNA
<213> ORGANISM: Artificial Sequence
<220> FEATURE:
<223> OTHER INFORMATION: Oligonucleotide Cas9_F

<400> SEQUENCE: 77
cggatcccca ccatggacta taaggaccac gac                                     33

<210> SEQ ID NO 78
<211> LENGTH: 31
<212> TYPE: DNA
<213> ORGANISM: Artificial Sequence
<220> FEATURE:
<223> OTHER INFORMATION: Oligonucleotide Cas9_R

<400> SEQUENCE: 78
gggaattctt acttttctt ttttgcctgg c                                        31

<210> SEQ ID NO 79
<211> LENGTH: 20
<212> TYPE: DNA
<213> ORGANISM: Artificial Sequence
<220> FEATURE:
<223> OTHER INFORMATION: Oligonucleotide Cas9_SF

<400> SEQUENCE: 79
catcgagcag atcagcgagt                                                    20

<210> SEQ ID NO 80
<211> LENGTH: 20
<212> TYPE: DNA
<213> ORGANISM: Artificial Sequence
<220> FEATURE:
<223> OTHER INFORMATION: Oligonucleotide Cas9_SR

<400> SEQUENCE: 80
cgatccgtgt ctcgtacagg                                                    20

<210> SEQ ID NO 81
<211> LENGTH: 39
<212> TYPE: DNA
<213> ORGANISM: Artificial Sequence
<220> FEATURE:
<223> OTHER INFORMATION: Oligonucleotide BTK_F

<400> SEQUENCE: 81
cggatccctg tgggacatgg ccgcagtgat tctggagag                               39

<210> SEQ ID NO 82
<211> LENGTH: 34
<212> TYPE: DNA
<213> ORGANISM: Artificial Sequence
<220> FEATURE:
<223> OTHER INFORMATION: Oligonucleotide BTK_R

<400> SEQUENCE: 82
gagcggccgc ttaggattct tcatccatga catc                                    34
```

<210> SEQ ID NO 83
<211> LENGTH: 20
<212> TYPE: DNA
<213> ORGANISM: Artificial Sequence
<220> FEATURE:
<223> OTHER INFORMATION: Oligonucleotide BTK_SF

<400> SEQUENCE: 83
tgtgttccac acctcagagc                                               20

<210> SEQ ID NO 84
<211> LENGTH: 20
<212> TYPE: DNA
<213> ORGANISM: Artificial Sequence
<220> FEATURE:
<223> OTHER INFORMATION: Oligonucleotide BTK_SR

<400> SEQUENCE: 84
ccaaacagtt tcgagctgcc                                               20

<210> SEQ ID NO 85
<211> LENGTH: 40
<212> TYPE: DNA
<213> ORGANISM: Artificial Sequence
<220> FEATURE:
<223> OTHER INFORMATION: Oligonucleotide GBA_F

<400> SEQUENCE: 85
ccgatatcct gtgggacatg gagttttcaa gtccttccag                         40

<210> SEQ ID NO 86
<211> LENGTH: 32
<212> TYPE: DNA
<213> ORGANISM: Artificial Sequence
<220> FEATURE:
<223> OTHER INFORMATION: Oligonucleotide GBA_R

<400> SEQUENCE: 86
aggaattcta ctggcgacgc cacaggtagg tg                                 32

<210> SEQ ID NO 87
<211> LENGTH: 20
<212> TYPE: DNA
<213> ORGANISM: Artificial Sequence
<220> FEATURE:
<223> OTHER INFORMATION: Oligonucleotide GBA_SF

<400> SEQUENCE: 87
ccagttgcac aacttcagcc                                               20

<210> SEQ ID NO 88
<211> LENGTH: 20
<212> TYPE: DNA
<213> ORGANISM: Artificial Sequence
<220> FEATURE:
<223> OTHER INFORMATION: Oligonucleotide GBA_SR

<400> SEQUENCE: 88
gtggtgagta ctgttggcga                                               20

<210> SEQ ID NO 89
<211> LENGTH: 38
<212> TYPE: DNA
<213> ORGANISM: Artificial Sequence
<220> FEATURE:
<223> OTHER INFORMATION: Oligonucleotide PDX1_F -continued

```
<400> SEQUENCE: 89
cggatcccct gtgggacatg aacggcgagg agcagtac                             38

<210> SEQ ID NO 90
<211> LENGTH: 31
<212> TYPE: DNA
<213> ORGANISM: Artificial Sequence
<220> FEATURE:
<223> OTHER INFORMATION: Oligonucleotide PDX1_R

<400> SEQUENCE: 90
ggaattccta tcgtggttcc tgcggccgcc g                                    31

<210> SEQ ID NO 91
<211> LENGTH: 20
<212> TYPE: DNA
<213> ORGANISM: Artificial Sequence
<220> FEATURE:
<223> OTHER INFORMATION: Oligonucleotide PDX1_SF

<400> SEQUENCE: 91
cacgcagctt tacaaggacc                                                 20

<210> SEQ ID NO 92
<211> LENGTH: 20
<212> TYPE: DNA
<213> ORGANISM: Artificial Sequence
<220> FEATURE:
<223> OTHER INFORMATION: Oligonucleotide PDX1_SR

<400> SEQUENCE: 92
ctttccacgc gtgagctttg                                                 20

<210> SEQ ID NO 93
<211> LENGTH: 18
<212> TYPE: DNA
<213> ORGANISM: Artificial Sequence
<220> FEATURE:
<223> OTHER INFORMATION: Oligonucleotide MVGFP_F

<400> SEQUENCE: 93
gggatccacc ggtcgcca                                                   18

<210> SEQ ID NO 94
<211> LENGTH: 29
<212> TYPE: DNA
<213> ORGANISM: Artificial Sequence
<220> FEATURE:
<223> OTHER INFORMATION: Oligonucleotide MVGFP_R

<400> SEQUENCE: 94
atagaattct tacttgtaca gctcgtcca                                       29

<210> SEQ ID NO 95
<211> LENGTH: 19
<212> TYPE: DNA
<213> ORGANISM: Artificial Sequence
<220> FEATURE:
<223> OTHER INFORMATION: Oligonucleotide LHA-F

<400> SEQUENCE: 95
gctgacgctg caggtgatc                                                  19

<210> SEQ ID NO 96
```

```
<211> LENGTH: 38
<212> TYPE: DNA
<213> ORGANISM: Artificial Sequence
<220> FEATURE:
<223> OTHER INFORMATION: Oligonucleotide LHA-R

<400> SEQUENCE: 96
gacaagatgt gtgtctaccg cttcaggtta cccgccag                              38

<210> SEQ ID NO 97
<211> LENGTH: 39
<212> TYPE: DNA
<213> ORGANISM: Artificial Sequence
<220> FEATURE:
<223> OTHER INFORMATION: Oligonucleotide RHA-F

<400> SEQUENCE: 97
tggcagggcg gggcgtaact acgcctctgt tcgtctcga                             39

<210> SEQ ID NO 98
<211> LENGTH: 20
<212> TYPE: DNA
<213> ORGANISM: Artificial Sequence
<220> FEATURE:
<223> OTHER INFORMATION: Oligonucleotide RHA-R

<400> SEQUENCE: 98
ctcagcagca actcacgtac                                                  20

<210> SEQ ID NO 99
<211> LENGTH: 38
<212> TYPE: DNA
<213> ORGANISM: Artificial Sequence
<220> FEATURE:
<223> OTHER INFORMATION: Oligonucleotide IN-F

<400> SEQUENCE: 99
ctggcgggta acctgaagcg gtagacacac atcttgtc                              38

<210> SEQ ID NO 100
<211> LENGTH: 42
<212> TYPE: DNA
<213> ORGANISM: Artificial Sequence
<220> FEATURE:
<223> OTHER INFORMATION: Oligonucleotide IN-1

<400> SEQUENCE: 100
atttttggcg aaaccattct atcatatgac aagatgtgtg tc                         42

<210> SEQ ID NO 101
<211> LENGTH: 42
<212> TYPE: DNA
<213> ORGANISM: Artificial Sequence
<220> FEATURE:
<223> OTHER INFORMATION: Oligonucleotide IN-2

<400> SEQUENCE: 101
atatgataga atggtttcgc caaaaatcaa taatcagaca ac                         42

<210> SEQ ID NO 102
<211> LENGTH: 37
<212> TYPE: DNA
<213> ORGANISM: Artificial Sequence
<220> FEATURE:
<223> OTHER INFORMATION: Oligonucleotide IN-R

<400> SEQUENCE: 102
```

```
caaactttt gatgttcatc ttgttgtctg attattg                             37
```

<210> SEQ ID NO 103
<211> LENGTH: 37
<212> TYPE: DNA
<213> ORGANISM: Artificial Sequence
<220> FEATURE:
<223> OTHER INFORMATION: Oligonucleotide SACB-F

<400> SEQUENCE: 103

```
caataatcag acaacaagat gaacatcaaa aagtttg                            37
```

<210> SEQ ID NO 104
<211> LENGTH: 38
<212> TYPE: DNA
<213> ORGANISM: Artificial Sequence
<220> FEATURE:
<223> OTHER INFORMATION: Oligonucleotide SACB-R

<400> SEQUENCE: 104

```
cttacgtgcc gatcattatt tgttaactgt taattgtc                           38
```

<210> SEQ ID NO 105
<211> LENGTH: 39
<212> TYPE: DNA
<213> ORGANISM: Artificial Sequence
<220> FEATURE:
<223> OTHER INFORMATION: Oligonucleotide CATR-F

<400> SEQUENCE: 105

```
caattaacag ttaacaaata atgatcggca cgtaagagg                          39
```

<210> SEQ ID NO 106
<211> LENGTH: 39
<212> TYPE: DNA
<213> ORGANISM: Artificial Sequence
<220> FEATURE:
<223> OTHER INFORMATION: Oligonucleotide CATR-R

<400> SEQUENCE: 106

```
cgagacgaac agaggcgtag ttacgccccg ccctgccac                          39
```